US009988679B2

(12) United States Patent
Gundlach et al.

(10) Patent No.: US 9,988,679 B2
(45) Date of Patent: Jun. 5, 2018

(54) MSP NANOPORES AND RELATED METHODS

(71) Applicants: University of Washington, Seattle, WA (US); The UAB Research Foundation, Birmingham, AL (US)

(72) Inventors: Jens H. Gundlach, Seattle, WA (US); Michael Niederweis, Homewood, AL (US); Thomas Z. Butler, Seattle, WA (US); Mikhail Pavlenok, Birmingham, AL (US); Mark A. Troll, Seattle, WA (US); Suja Sukumaran, Dublin, CA (US)

(73) Assignees: University of Washington, Seattle, WA (US); The UAB Research Foundation, Birmingham, AL (US)

( * ) Notice: Subject to any disclaimer, the term of this patent is extended or adjusted under 35 U.S.C. 154(b) by 0 days. days.

(21) Appl. No.: 15/488,311

(22) Filed: Apr. 14, 2017

(65) Prior Publication Data

US 2017/0218443 A1 Aug. 3, 2017

Related U.S. Application Data

(60) Division of application No. 14/318,072, filed on Jun. 27, 2014, now Pat. No. 9,624,275, which is a continuation of application No. 14/215,871, filed on Mar. 17, 2014, now Pat. No. 9,170,230, which is a continuation of application No. 13/069,187, filed on Mar. 22, 2011, now Pat. No. 8,673,550, which is a continuation of application No. PCT/US2009/057915, filed on Sep. 22, 2009.

(60) Provisional application No. 61/098,938, filed on Sep. 22, 2008.

(51) Int. Cl.
| A61K 39/04 | (2006.01) |
| A61K 39/02 | (2006.01) |
| C12Q 1/00 | (2006.01) |
| C12Q 1/68 | (2018.01) |
| G01N 27/447 | (2006.01) |
| G01N 33/487 | (2006.01) |
| A61K 39/00 | (2006.01) |
| G01N 24/00 | (2006.01) |

(52) U.S. Cl.
CPC ............ *C12Q 1/6869* (2013.01); *A61K 39/04* (2013.01); *G01N 27/44791* (2013.01); *G01N 33/48721* (2013.01); *A61K 39/00* (2013.01); *G01N 24/00* (2013.01)

(58) Field of Classification Search
CPC ........ A61K 39/00; A61K 39/02; A61K 39/04; G01N 24/00; G01N 27/00
USPC ...... 424/234.1, 248.1; 435/4; 536/23.1, 23.7
See application file for complete search history.

(56) References Cited

U.S. PATENT DOCUMENTS

| 5,795,782 | A | 8/1998 | Church et al. |
| 6,015,714 | A | 1/2000 | Baldarelli et al. |
| 6,267,872 | B1 | 7/2001 | Akeson et al. |
| 6,362,002 | B1 | 3/2002 | Denison et al. |
| 6,406,880 | B1 | 6/2002 | Thornton |
| 6,428,959 | B1 | 8/2002 | Deamer |
| 6,617,113 | B2 | 9/2003 | Deamer |
| 6,673,615 | B2 | 1/2004 | Denison et al. |
| 6,746,594 | B2 | 6/2004 | Akeson et al. |
| 6,936,433 | B2 | 8/2005 | Akeson et al. |
| 7,189,503 | B2 | 3/2007 | Akeson et al. |
| 7,238,485 | B2 | 7/2007 | Akeson et al. |
| 7,444,053 | B2 | 10/2008 | Schmidt et al. |
| 7,713,544 | B2 | 5/2010 | Chaikof et al. |
| 8,673,550 | B2 | 3/2014 | Gundlach et al. |
| 2006/0063171 | A1 | 3/2006 | Akeson et al. |
| 2007/0190542 | A1 | 8/2007 | Ling et al. |
| 2007/0269843 | A1 | 11/2007 | Thornton |
| 2009/0298072 | A1 | 12/2009 | Ju |

FOREIGN PATENT DOCUMENTS

| JP | 7-248329 A | 9/1995 |
| WO | 01/16327 A2 | 3/2001 |
| WO | 01/16328 A2 | 3/2001 |
| WO | 2004/032511 A1 | 4/2004 |
| WO | 2006/028508 A2 | 3/2006 |
| WO | 2009/044170 A1 | 4/2009 |
| WO | 2015/166275 A1 | 11/2015 |

OTHER PUBLICATIONS

Jennifer Harris Aug. 16, 2007 Email, Exhibit 1049, submitted Mar. 11, 2015, in support of Petitioner's Reply to Patent Owners' Response in U.S. Patent Trial and Appeal Board Case No. IPR2014-00513, *Oxford Nanopore Technologies, Ltd.* v. *The University of Washington and the UAB Research Foundation*, 1 page.
Jetha, N.N., et al., "Forming an α-Hemolysin Nanopore for Single-Molecule Analysis," Chap. 9 of "Micro and Nano Technologies in Bioanalysis, Methods in Molecular Biology," vol. 544, pp. 113-127, 2009, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 15 pages.
Joint List of Disputed Claim Terms and Proposed Constructions, submitted in U.S. International Trade Commission, Investigation No. 337-TA-991, In The Matter Of Certain Nanopores and Products Containing Same, submitted Jun. 10, 2016, 8 pages.

(Continued)

*Primary Examiner* — Rodney P Swartz
(74) *Attorney, Agent, or Firm* — Christensen O'Connor Johnson Kindness PLLC

(57) ABSTRACT

Provided herein are *Mycobacterium smegmatis* porin nanopores, systems that comprise these nanopores, and methods of using and making these nanopores. Such nanopores may be wild-type MspA porins, mutant MspA porins, wild-type MspA paralog porins, wild-type MspA homolog porins, mutant MspA paralog porins, mutant MspA homolog porins, or single-chain Msp porins. Also provided are bacterial strains capable of inducible Msp porin expression.

15 Claims, 35 Drawing Sheets

(56) References Cited

OTHER PUBLICATIONS

Kalita, M., et al., "Enhancing the Water Solubility of Nanoparticles (CdSe, Au, Au/Fe) by Ligand Exchange and Subsequent Binding to a Cysteine Mutant of the Mycobacterial Porin MspA," Abstract 217, The 41st Midwest Regional Meeting, Oct. 25-27, 2006, <http://acs.confex.com/acs/mwrm06/techprogram/P38606.HTM> [retrieved Aug. 21, 2012], 1 page.

Karow, J., "AGBT: Oxford Nanopore to Begin Selling Two Low-Cost DNA Strand Sequencing Instruments This Year," www.genomeweb.com, Feb. 21, 2012, pp. 1-4, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 4 pages.

Kasianowicz, J.J., et al., "Characterization of Individual Polynucleotide Molecules Using a Membrane Channel," Proceedings of the National Academy of Sciences of the United States of America (PNAS) 93(24):13770-13773, Nov. 1996.

Laszlo, A.H., et al., "Nanopore Sequencing of the Phi X 174 Genome," University of Washington, 2014, cited in U.S.D.C., Southern District of California, Case No. 3:16-cv-00477-LAB-MDD, as exhibit 16, and cited in ITC, Investigation No. 337-3123, as exhibit 32, 39 pages.

Letter Accompanying Subsequently Filed Items, submitted Feb. 14, 2013, in corresponding European Patent Application No. 09815404.0, filed Sep. 22, 2009, exhibit cited in U.S. Patent Trial and Appeal Board Case No. IPR2014-00512 and Case No. IPR2014-00513,15 pages.

"Licensing Deal Marks Coming of Age for UAB-UW Nanopore Sequencing Technology," Press Release, UAB News, <http://www.uab.news/innovation/item/3847-licensing-deal-marks-coming-of-age-for-uab-uw-nanopore-sequencing-technology.html> [retrieved Mar. 13, 2014], exhibit cited in U.S. Patent Trial and Appeal Board Case No. IPR2014-00512 and Case No. IPR2014-00513, 4 pages.

Litchtinger, T., et al., "Evidence for a Small Anion-Selective Channel in the Cell Wall of *Mycobacterium bovis* BCG Besides a Wide Cation-Selective Pore," FEBS Letters 454(3):349-355, Jul. 1999.

Lu, B., et al., "Thermal Motion of DNA in an MspA Pore," Harvard University, Jun. 2015, cited in U.S.D.C., Southern District of California, Case No. 3:16-cv-00477-LAB-MDD, as exhibit 29, and cited in ITC, Investigation No. 337-3123, as exhibit 96, 16 pages.

Maglia, G., et al., "Enhanced Translocation of Single DNA Molecules Through α-Hemolysin Nanopores by Manipulation of Internal Change," Proceedings of the National Academy of Science USA 105(50):19720-19725, 2008.

Mahfoud M. et al., "Topology of the Porin MspA in the Outer Membrane of *Mycobacterium smegmatis*," Journal of Biological Chemistry 281(9):5908-5915, Mar. 2006.

Manrao, E.A., et al., "Nucleotide Discrimination with DNA Immobilized in the MspA Nanopore," Oct. 2011, exhibit 24 cited in ITC, Investigation No. 337-3123, 10 pages.

Maria Vignone Mar. 4, 2015 Email on Behalf of the U.S. Patent Trial and Appeal Board in U.S. Patent Trial and Appeal Board Case No. IPR2014-00513, *Oxford Nanopore Technologies, Ltd.* v. *The University of Washington and the UAB Research Foundation*, 5 pages.

Meller, A., and D. Branton, "Single Molecule Measurements of DNA Transport Through a Nanopore," Electrophoresis 23(16):2583-2591, Aug. 2002.

Meller, A., et al., "Rapid Nanopore Discrimination Between Single Polynucleotide Molecules," Proceedings of the National Academy of Science USA (PNAS) 97(3):1079-1084, Feb. 2000, exhibit cited in U.S. Patent Trial and Appeal Board Case No. IPR2014-00512 and Case No. IPR2014-00513.

Meller, A., et al., "Voltage-Driven DNA Translocations Through a Nanopore," Physical Review Letters 86(15):3435-3438, Apr. 2001, exhibit cited in U.S. Patent Trial and Appeal Board Case No. IPR2014-00512 and Case No. IPR2014-00513.

Minier, F., and E. Sigel, "Techniques: Use of Concatenated Subunits for the Study of Ligand-Gated Ion Channels," Trends in Pharmacological Sciences 25(9):499-503, Sep. 2004.

MIT Technology Review, "The Smartest Company in the World. And It's Not Google." Mar./Apr. 2014, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 6 pages.

Movileanu, L., "Interrogating Single Proteins Through Nanopores: Challenges and Opportunities," Trends in Biotechnology 27(6):333-341, Jun. 2009.

Myers, T., PNAS Editorial Staff Member, E-mail dated Aug. 22, 2008, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 6 pages.

Nakane, J.J., et al., "Nanopore Sensors for Nucleic Acid Analysis," Journal of Physics: Condensed Matter 15(32):R1365-R1393, Aug. 2003, exhibit submitted Jun. 29, 2015, in support of Patent Owners' Supplemental Response for U.S. Patent Trial and Appeal board, Case No. IPR2014-00513, *Oxford Nanopore Technologies Ltd.* v. *University of Washington and UAB Research Foundation*, 29 pages.

National Human Genome Research Institute response to Baker Botts LLP Freedom of Information Act request, Dec. 13, 2013, exhibit cited in U.S. Patent Trial and Appeal Board Case No. IPR2014-00512 and Case No. IPR2014-00513, 1 page.

National Institutes of Health Public Health Service Grant Instructions, exhibit cited in U.S. Patent Trial and Appeal Board Case No. IPR2015-00057, 66 pages.

Niederweis, M., "Mycobacterial Porins—New Channel Proteins in Unique Outer Membranes," Molecular Microbiology 49(5):1167-1177, Sep. 2003.

Niederweis, M., et al., "Cloning of the mspA Gene Encoding a Porin From *Mycobacterium smegmatis*," Molecular Microbiology 33(5):933-945, Sep. 1999.

Notice of Deposition of Jennifer Harris, Exhibit 1 to the Deposition of Jennifer Harris in U.S. Patent Trial and Appeal Board Case No. IPR2014-00513, *Oxford Nanopore Technologies, Ltd.* v. *The University of Washington and the UAB Research Foundation*, Jan. 26, 2015, 3 pages.

Notification of the First Office Action and Search Report dated Jun. 25, 2013, issued in corresponding Chinese Application No. 200980142855.5, filed Sep. 22, 2009, 26 pages.

"Order: Conduct of the Proceeding: 37 C.F.R. § 42.5," U.S. Patent Trial and Appeal Board Paper No. 25, issued Feb. 19, 2015, in U.S. Patent Trial and Appeal Board Case No. IPR2014-00513, *Oxford Nanopore Technologies, Ltd.* v. *The University of Washington and the Uab Research Foundation*, 5 pages.

"Page and HPLC Purification," <http://www.idtdna.com/pages/products/dna-rna/hplc-page> [retrieved Feb. 9, 2015], Exhibit 5 to the Deposition of Steven A Benner, in U.S. Patent Trial and Appeal Board Case No. IPR2014-00513, *Oxford Nanopore Technologies, Ltd.* v. *The University of Washington and the UAB Research Foundation*, Feb. 12, 2015, 2 pages.

Pamphlet of University of Washington Summer Research Poster Session, Seattle, Washington, Aug. 16, 2007, exhibit in U.S. Patent Trial and Appeal Board Case No. IPR2014-00513, *Oxford Nanopore Technologies Ltd.* v. *University of Washington and UAB Research Foundation*, filed on Dec. 11, 2014, 56 pages.

Patent Owners' Demonstratives for Oral Argument in U.S. Patent Trial and Appeal Board, Case No. IPR2014-00513, *Oxford Nanopore Technologies Ltd.* v. *The University of Washington and the UAB Research Foundation*, submitted Dec. 3, 2015, 89 pages.

Patent Owners' Motion to Amend in U.S. Patent Trial and Appeal Board Case No. IPR2014-00513, *Oxford Nanopore Technologies Ltd.* v. *University of Washington and UAB Research Foundation*, filed on Dec. 11, 2014, 7 pages.

Patent Owners' Preliminary Response in U.S. Patent Trial and Appeal Board Case No. IPR2015-00027, *Oxford Nanopore Technologies Ltd.* v. *University of Washington and UAB Research Foundation*, filed on Jan. 29, 2015, 34 pages.

(56) References Cited

OTHER PUBLICATIONS

Patent Owners' Response in U.S. Patent Trial and Appeal Board Case No. IPR2014-00513, *Oxford Nanopore Technologies Ltd. v. University of Washington and UAB Research Foundation*, filed on Dec. 11, 2014, 33 pages.

Patent Owners' Supplemental Response in U.S. Patent Trial and Appeal Board Case No. IPR2014-00513, *Oxford Nanopore Technologies Ltd. v. University of Washington and UAB Research Foundation*, submitted Jun. 29, 2015, 60 pages.

Pennisi, E., "Genome Sequencing: Search for Pore-fection," Science 336(6081):534-537, May 2012, exhibit submitted Jun. 29, 2015, in support of Patent Owners' Supplemental Response for U.S. Patent Trial and Appeal Board, Case No. IPR2014-00513, *Oxford Nanopore Technologies Ltd. v. University of Washington and UAB Research Foundation*, 4 pages.

Petitioner's Demonstratives for Oral Argument in U.S. Patent Trial and Appeal Board, Case No. IPR2014-00513, *Oxford Nanopore Technologies Ltd. v. The University of Washington and the UAB Research Foundation*, submitted Dec. 3, 2015, 53 pages.

Petitioner's Reply to Patent Owners' Response, in U.S. Patent Trial and Appeal Board Case No. IPR2014-00513, *Oxford Nanopore Technologies, Ltd. v. The University of Washington and the UAB Research Foundation*, served Mar. 11, 2015, 20 pages.

Petitioner's Reply to Patent Owners' Supplemental Response in U.S. Patent Trial and Appeal Board Case No. IPR2014-00513, *Oxford Nanopore Technologies Ltd. v. University of Washington and UAB Research Foundation*, submitted Aug. 28, 2015, 32 pages.

Project Information Page for Project No. 1R21HG004145 01: http://projectreporter.nih.gov/project_info_details.cfm?aid=7192749&icde=22969799 [retrieved Jan. 20, 2015], exhibit cited in Patent Owners' Preliminary Response in U.S. Patent Trial and Appeal Board Case No. IPR2015-00057, 1 page.

ProQuest response to e-mail inquiry re Thomas Butler's dissertation, Nov. 4, 2013, exhibit cited in U.S. Patent Trial and Appeal Board Case No. IPR2014-00512 and Case No. IPR2014-00513, 1 page.

"Purification of Oligonucleotides," Quick Look Version of the Full Technical Report "Chemical Synthesis of Oligonucleotides," © 2009 and 2011 Integrated DNA Technologies, Exhibit 1051, submitted Mar. 11, 2015, in support of Petitioner's Reply to Patent Owners' Response in U.S. Patent Trial and Appeal Board Case No. IPR2014-00513, *Oxford Nanopore Technologies, Ltd. v. The University of Washington and the UAB Research Foundation*, 3 pages.

Record of Oral Hearing held in U.S. Patent Trial and Appeal Board, Case No. IPR2014-00513, *Oxford Nanopore Technologies Ltd. v. The University of Washington and The UAB Research Foundation*, mailed Jan. 4, 2016, 90 pages.

Respondents Oxford Nanopore Technologies Ltd. and Oxford Nanopore Technologies, Inc.'s Notice of Prior Art, submitted in U.S. International Trade Commission, Investigation No. 337-TA-991, In The Matter Of Certain Nanopores and Products Containing Same, submitted May 27, 2016, 15 pages.

Response of Oxford Nanopore Technologies Ltd. and Oxford Nanopore Technologies, Inc. to the Complaint of Illumina, Inc., University of Washington and UAB Research Foundation and Notice of Investigation, submitted in U.S. International Trade Commission, Investigation No. 337-TA-991, In The Matter Of Certain Nanopores and Products Containing Same, submitted Apr. 25, 2016, 99 pages.

Rhee, M., and M.A. Burns, "Nanopore Sequencing Technology: Nanopore Preparations," Trends in Biotechnology 25(4):174-181, Apr. 2007, exhibit submitted Jun. 29, 2015, in support of Patent Owners' Supplemental Response for U.S. Patent Trial and Appeal Board, Case No. IPR2014-00513, *Oxford Nanopore Technologies Ltd. v. University of Washington and UAB Research Foundation*, 8 pages.

Rhee M., and M.A. Burns, "Nanopore Sequencing Technology: Research Trends and Applications," Trends in Biotechnology 24(12):580-586, Dec. 2006.

Rieβ, F.G., et al., "Study of the Properties of a Channel-Forming Protein of the Cell Wall of the Gram-Positive Bacterium *Mycobacterium phlei*," Journal of Membrane Biology 182(2):147-157, Jul. 2001.

"2007 Amgen Faculty," <https://web.archive.org/web/20080907044611//http:/www.washington.edu/research/urp/am . . . > [retrieved Jan. 29, 2015], Exhibit 5 to the Deposition of Jennifer Harris in U.S. Patent Trial and Appeal Board Case No. IPR2014-00513, *Oxford Nanopore Technologies, Ltd. v. The University of Washington and the UAB Research Foundation*, Feb. 3, 2015, 7 pages.

"2007 Amgen Scholars," <https://web.archive.org/web/20080201130247//http:/www.washington.edu/research/urp/am . . . > [retrieved Jan. 20, 2015], Exhibit 6 to the Deposition of Jennifer Harris in U.S. Patent Trial and Appeal Board Case No. IPR2014-00513, *Oxford Nanopore Technologies, Ltd. v. The University of Washington and the UAB Research Foundation*, Feb. 3, 2015, 6 pages.

"About the Amgen Scholars Program: Jun. 18-Aug. 17, 2007," <https://web.archive.org/web/20070705202640/http:/www.washington.edu/research/urp/stu . . . > [retrieved Jan. 29, 2015], Exhibit 4 to the Deposition of Jennifer Harris in U.S. Patent Trial and Appeal Board Case No. IPR2014-00513, *Oxford Nanopore Technologies, Ltd. v. The University of Washington and the UAB Research Foundation*, Feb. 3, 2015, 1 page.

Abstract Listing, Exhibit 8 to the Deposition of Jennifer Harris in U.S. Patent Trial and Appeal Board Case No. IPR2014-00513, *Oxford Nanopore Technologies, Ltd. v. The University of Washington and the UAB Research Foundation*, Feb. 3, 2015, 5 pages.

Akeson, M., et al., "Microsecond Time-Scale Discrimination Among Polycytidylic Acid, Polyadenylic Acid, and Polyuridylic Acid as Homopolymers or as Segments Within Single RNA Molecules," Biophysical Journal 77(6):3227-3233, Dec. 1999.

"Analyte," online definition at Dictionary.com, Jun. 17, 2014, <http:/dictionary.reference.com/browse/analyse?s=t>, exhibit cited in U.S. Patent Trial and Appeal Board Case No. IPR2014-00513, 2 pages.

Analytical ESI-MS Report by Integrated DNA Technologies, Exhibit 1053 in U.S. Patent Trial and Appeal Board Case No. IPR2014-00513, *Oxford Nanopore Technologies, Ltd. v. The University of Washington and the UAB Research Foundation*, Apr. 1, 2015, 1 page.

Ball, K.A., "Ion Channel Gating and DNA Translocation in Single MspA Protein Pores," University of Washington Physics REU (Research Experiences for Undergraduates) Summer Research Program, manuscript and presentation slides, drafted and presented Summer 2006, 25 pages.

Baumann, S.W., et al., "Forced Subunit Assembly in α1β2γ 2 GABAA Receptors," Journal of Biological Chemistry 277(48):46020-46025, Nov. 2002.

Bayley, H., "Nanopore Sequencing: From Imagination to Reality," Clinical Chemistry 61(1):25-31, 2015, exhibit submitted Jun. 29, 2015, in support of Patent Owners' Supplemental Response for U.S. Patent Trial and Appeal Board, Case No. IPR2014-00513, *Oxford Nanopore Technologies Ltd. v. University of Washington and UAB Research Foundation*, 11 pages.

Bayley, H., and L. Jayasinghe, "Functional Engineered Channels and Pores (Review)," Molecular Membrane Biology 21(4):209-220, Jul.-Aug. 2004.

Bayley, H., and P.S. Cremer, "Stochastic Sensors Inspired by Biology," Nature 413(6852):226-230, Sep. 2001.

Benner, S., et al., "Sequence-Specific Detection of Individual DNA Polymerase Complexes in Real Time Using a Nanopore," Nature Nanotechnology 2(11):718-724, Nov. 2007.

Benner, S.A., Ph.D., Declaration, Jun. 26, 2015, exhibit submitted Jun. 29, 2015, in support of Patent Owners' Supplemental Response for U.S. Patent Trial and Appeal Board, Case No. IPR2014-00513, *Oxford Nanopore Technologies Ltd. v. University of Washington and UAB Research Foundation*, 21 pages.

Berkane E.,et al., "Nanopores: Maltoporin Channel as a Sensor for Maltodextrin and Lambda-Phage," J Nanobiotech 3:3, 2005, Exhibit 1064 Submitted Aug. 28, 2015, in *Oxford Nanopore Tech-*

(56) References Cited

OTHER PUBLICATIONS nologies Ltd. v. *University of Washington and UAB Research Foundation*, Before the U.S. Patent Trial and Appeal Board, Case No. IPR2014-00513, 6 pages.

Bossman, S.H., et al., "Nanotechnology on Surfaces Using Mutants of MspA From *Mycobacterium smegmatis*," Abstract 66, the 41st Midwest Regional Meeting, Oct. 25-27, 2006, <http://acs.confex.com/acs/mwrm06/techprogram/P38604.HTM> [retrieved Aug. 21, 2012], 1 page.

Branton, D., E-mail dated Jul. 28, 2008, exhibit submitted Jun. 29, 2015, in support of Patent Owners' Supplemental Response for U.S. Patent Trial and Appeal Board, Case No. IPR2014-00513, *Oxford Nanopore Technologies Ltd. v. University of Washington and UAB Research Foundation*, 30 pages.

Branton, D., E-mail dated Jul. 30, 2008, exhibit submitted Jun. 29, 2015, in support of Patent Owners' Supplemental Response for U.S. Patent Trial and Appeal Board, Case No. IPR2014-00513, *Oxford Nanopore Technologies Ltd. v. University of Washington and UAB Research Foundation*, 4 pages.

Branton, D., et al., "The Potential and Challenges of Nanopore Sequencing," Nature Biotechnology 26(10):1146-1153, Oct. 2008.

Branton, D., Transcript of Deposition, Apr. 15, 2015, exhibit submitted Jun. 29, 2015, in support of Patent Owners' Supplemental Response for U.S. Patent Trial and Appeal Board, Case No. IPR2014-00513, *Oxford Nanopore Technologies Ltd. v. University of Washington and UAB Research Foundation*, 165 pages.

Branton, D., Transcript of Deposition, Jun. 19, 2015, exhibit submitted Jun. 29, 2015, in support of Patent Owners' Supplemental Response for U.S. Patent Trial and Appeal Board, Case No. IPR2014-00513, *Oxford Nanopore Technologies Ltd. v. University of Washington and UAB Research Foundation*, 237 pages.

Butler, T., "Nanopore Analysis of Nucleic Acids," doctoral dissertation, University of Washington, Seattle, Washington, 2007, 120 pages.

Butler, T.Z., "Nanopore Analysis of Nucleic Acids," Dissertation Defense Presentation, University of Washington, Seattle, Washington, May 29, 2007.

Butler, T.Z., et al., "Determination of RNA Orientation During Translocation Through a Biological Nanopore," Biophysical Journal 90(1):190-199, Jan. 2006, exhibit cited in U.S. Patent Trial and Appeal Board Case No. IPR2014-00512 and Case No. IPR2014-00513.

Butler, T.Z., et al., "Single-Molecule DNA Detection With an Engineered MspA Protein Nanopore," Proceedings of the National Academy of Sciences of the United States of America (PNAS) 105(52):20647-20652, Dec. 2008.

Chen, P., et al., "Probing Single DNA Molecule Transport Using Fabricated Nanopores," Nano Letters 4(11):2293-2298, Nov. 2004, exhibit submitted Jun. 29, 2015, in support of Patent Owners' Supplemental Response for U.S. Patent Trial and Appeal Board, Case No. IPR2014-00513, *Oxford Nanopore Technologies Ltd. v. University of Washington and UAB Research Foundation*, 6 pages.

Clarke, J., et al., "Continuous Base Identification for Single-Molecule Nanopore DNA Sequencing," Nature Nanotechnology 4:265-270, 2009.

Cockroft, S.L., et al., "A Single-Molecule Nanopore Device Detects DNA Polymerase Activity With Single-Nucleotide Resolution," Journal of the American Chemical Society 130(3):818-820, Jan. 2008.

Communication Pursuant to Article 94(3) EPC, European Patent Application No. 09815404.0, dated Jun. 20, 2014, exhibit cited in U.S. Patent Trial and Appeal Board Case No. IPR2015-00057, 6 pages.

Communication Pursuant to Rule 114(2) EPC, European Patent Application No. 09815404.0, dated Nov. 27, 2012, exhibit cited in U.S. Patent Trial and Appeal Board Case No. IPR2015-00057, 20 pages.

Complainants' Statement on the Public Interest, submitted in U.S. International Trade Commission, Investigation No. 337-3123, In The Matter Of Certain Nanopores and Products Containing Same, submitted Feb. 23, 2016, 5 pages.

Complaint for Patent Infringement, submitted in U.S.D.C., Southern District of California, Case No. 3:16-cv-00477-LAB-MDD, *Illumina, Inc., et al. v. Oxford Nanopore Technologies, et al.*, submitted Feb. 23, 2016, 14 pages.

Complaint of Illumina, Inc., et al., Under Section 337 of the Tariff Act of 1930, as Amended, submitted in U.S. International Trade Commission, Investigation No. 337-3123, In The Matter Of Certain Nanopores and Products Containing Same, submitted Feb. 23, 2016, 39 pages.

Correspondence With U.S. Patent and Trademark Office, U.S. Appl. No. 13/069,187, filed Mar. 22, 2011, exhibit cited in U.S. Patent Trial and Appeal Board Case No. IPR2015-00057, 119 pages.

Dani, R.K., et al., "MspA Porin—Gold Nanoparticle Assemblies: Enhanced Binding Through a Controlled Cysteine Mutation," Nano Letters 8(4):1229-1236, Apr. 2008.

Deamer, D.W., and D. Branton, "Characterization of Nucleic Acids by Nanopore Analysis," Accounts of Chemical Research 35(10):817-825, Oct. 2002.

Deamer, D.W., and M. Akeson, "Nanopores and Nucleic Acids: Prospects for Ultrarapid Sequencing," Trends in Biotechnology (TIBTECH) 18(4):147-151, Apr. 2000, exhibit cited in U.S. Patent Trial and Appeal Board Case No. IPR2014-00512 and Case No. IPR2014-00513.

Decision Granting Petitioners Motion for Joinder and Instituting Inter Partes Review, 37 C.F.R. §§ 42.108, 42.122, in U.S. Patent Trial and Appeal Board Case No. IPR2014-00513[1], *Oxford Nanopore Technologies Ltd. v. University of Washington and the UAB Research Foundation*, Apr. 27, 2015, 31 pages.

Decision in U.S. Patent Trial and Appeal Board Case No. IPR2014-00512, *Oxford Nanopore Technologies Ltd. v. University of Washington and UAB Research Foundation*, Sep. 15, 2014, 22 pages.

Decision in U.S. Patent Trial and Appeal Board Case No. IPR2014-00513, *Oxford Nanopore Technologies Ltd. v. University of Washington and UAB Research Foundation*, Sep. 15, 2014, 30 pages.

Declaration of Daniel Branton, Exhibit 1044 in U.S. Patent Trial and Appeal Board Case No. IPR2014-00513, *Oxford Nanopore Technologies, Ltd. v. The University of Washington and the UAB Research Foundation*, Mar. 11, 2015, 16 pages.

Declaration of Daniel Branton, exhibit cited in U.S. Patent Trial and Appeal Board Case No. IPR2014-00512 and Case No. IPR2014-00513, Mar. 18, 2014, 236 pages.

Declaration of Daniel Branton, exhibit cited in U.S. Patent Trial and Appeal Board Case No. IPR2015-00057, Oct. 11, 2014, 91 pages.

Declaration of James Willcocks, exhibit cited in U.S. Patent Trial and Appeal Board Case No. IPR2015-00057, Oct. 13, 2014, 4 pages.

Declaration of Jennifer Harris, exhibit in U.S. Patent Trial and Appeal Board Case No. IPR2014-00513, *Oxford Nanopore Technologies Ltd. v. University of Washington and UAB Research Foundation*, filed on Dec. 11, 2014, 6 pages.

Declaration of Lindsey Miles, executed May 27, 2014, 3 pages.

Declaration of Roland Benz, exhibit cited in U.S. Patent Trial and Appeal Board Case No. IPR2014-00512 and Case No. IPR2014-00513, Mar. 17, 2014, 124 pages.

Declaration of Roland Benz, exhibit cited in U.S. Patent Trial and Appeal Board Case No. IPR2015-00057, Oct. 13, 2014, 71 pages.

Declaration of Steven A. Benner, Ph.D., exhibit in U.S. Patent Trial and Appeal Board Case No. IPR2014-00513, *Oxford Nanopore Technologies Ltd. v. University of Washington and UAB Research Foundation*, filed on Dec. 11, 2014, 33 pages.

Deposition of Steven A. Benner, Exhibit 1042 to U.S. Patent Trial and Appeal Board Case No. IPR2014-00513, *Oxford Nanopore Technologies, Ltd. v. The University of Washington and the UAB Research Foundation*, Feb. 12, 2015, 36 pages.

Deposition of Steven Benner, Ph.D., taken Jul. 31, 2015, Exhibit 1058 Submitted Aug. 28, 2015, in *Oxford Nanopore Technologies, Ltd. v. University of Washington and UAB Research Foundation*, Before the U.S. Patent Trial and Appeal Board, Case No. IPR2015-00057 [joined with IPR2014-00513], 69 pages.

Deposition Upon Oral Examination of Daniel Branton in U.S. Patent Trial and Appeal Board Case No. IPR2014-00513, *Oxford*

(56) References Cited

OTHER PUBLICATIONS

*Nanopore Technologies, Ltd.* v. *The University of Washington and the UAB Research Foundation*, Apr. 15, 2015, 165 pages.
Deposition Upon Oral Examination of Jennifer Harris, Exhibit 1045 to U.S. Patent Trial and Appeal Board Case No. IPR2014-00513, *Oxford Nanopore Technologies, Ltd.* v. *The University of Washington and the UAB Research Foundation*, Feb. 3, 2015, 75 pages.
Derrington, I.M., et al., "Nanopore DNA Sequencing With MspA," PNAS 107(37):16060-16065, Sep. 2010, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 6 pages.
DNA Sequencing—The Hole Story: Nanopores May Lead the Way to a New Generation of Sequencing, The Economist, Oct. 16, 2008, pp. 1-2, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 2 pages.
Dörner, U., et al., "Identification of a Cation-Specific Channel (TipA) in the Cell Wall of the Gram-Positive Mycolata Tsukamurella inchonensis: The Gene of the Channel-Forming Protein Is Identical to mspA of *Mycobacterium smegmatis* and mppA of *Mycobacterium phlei*," Biochimica et Biophysica Acta 1667(1):47-55, Nov. 2004, exhibit cited in U.S. Patent Trial and Appeal Board Case No. IPR2014-00512 and Case No. IPR2014-00513.
Engelhardt, H., et al., "A Tetrameric Porin Limits the Cell Wall Permeability of *Mycobacterium smegmatis*," Journal of Biological Chemistry 277(40):37567-37572, Oct. 2002.
Entry into the European Phase Before the European Patent Office, dated Jan. 28, 2011, issued in corresponding European Patent Application No. 09815404.0, filed Sep. 22, 2009, exhibit cited in U.S. Patent Trial and Appeal Board Case No. IPR2014-00512 and Case No. IPR2014-00513, 3 pages.
European Patent Office Communication Pursuant to Rule 114(2) EPC with Third Party Observations, dated Dec. 3, 2012, issued in corresponding European Application No. 09815404.0, filed Sep. 22, 2009, 21 pages.
European Search Report dated Jul. 20, 2012, issued in corresponding European Application No. 09815404.0, filed Sep. 22, 2009, 6 pages.
Faller, M., et al., "The Structure of a Mycobacterial Outer-Membrane Channel," Science 303(5661):1189-1192, Feb. 2004.
Final Written Decision in U.S. Patent Trial and Appeal Board, Case No. IPR2014-00513, *Oxford Nanopore Technologies Ltd.* v. *The University of Washington and the UAB Research Foundation*, submitted Feb. 26, 2016, 58 pages.
"First Year Amgen Scholars and Leading Scientists Attend Symposium to Explore Drug Discovery & Development," News Release, Aug. 7, 2007, <http://www.amgen.com/media/media_pr_detail.jsp?releaseID=1037887> [retrieved Jan. 29, 2015], Exhibit 10 to the Deposition of Jennifer Harris in U.S. Patent Trial and Appeal Board Case No. IPR2014-00513, *Oxford Nanopore Technologies*, Ltd. v. *The University of Washington and the UAB Research Foundation*, Feb. 3, 2015, 2 pages.
Folgering, J.H.A., et al., "Engineering Covalent Oligomers of the Mechanosensitive Channel of Large Conductance From *Escherichia coli* With Native Conductance and Gating Characteristics," Protein Science 14(12):2947-2954, Dec. 2005.
Funding Opportunity Announcement for RFA-HG-05-004: http://grants.nih.gov/grants/guide/rfa-files/RFA-HG-05-004.html [retrieved Jan. 20, 2015], exhibit cited in Patent Owners' Preliminary Response in U.S. Patent Trial and Appeal Board Case No. IPR2015-00057, 23 pages.
Griffiths, J., "The Realm of the Nanopore," Analytical Chemistry 80(1):23-27, Jan. 2008, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 5 pages.
Gundlach, J., "Engineering MspA for Nanopore Sequencing," Grant Application Abstract, project period Sep. 26, 2006, through Aug. 31, 2008, 1 page.
Gundlach, J., cover letter to PNAS dated Jul. 31, 2008, including submission of manuscript entitled "Single-molecule DNA detection with an engineered MspA protein nanopore" and supplemental information; and letter from Dr. Daniel Branton to PNAS dated Jul. 30, 2008, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 31 pages.
Gundlach, J., E-mail dated Feb. 19, 2012, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 1 page.
Gundlach, J.H., "Engineering MspA for Nanopore Sequencing," National Human Genome Research Institute Grant No. 1R21HG004145-01, awarded Sep. 25, 2006, exhibit cited in U.S. Patent Trial and Appeal Board Case No. IPR2014-00512 and Case No. IPR2014-00513, 38 pages.
Gundlach, J.H., "Engineering MspA for Nanopore Sequencing," National Human Genome Research Institute Grant Supplement No. 5R21HG004145-02, awarded Aug. 20, 2007, exhibit cited in U.S. Patent Trial and Appeal Board Case No. IPR2014-00512 and Case No. IPR2014-00513, 13 pages.
Gundlach, J.H., et al., "MSP Nanopores and Related Methods," U.S. Pat. No. 8,673,550, issued Mar. 18, 2014, "Petition for Inter Partes Review of U.S. Pat. No. 8,673,550 Under 35 U.S.C. §§ 311-319 and 37 C.F.R. §§ 42.100 et seq." to the U.S. Patent Trial and Appeal Board, Case No. IPR2014-00512, served Mar. 18, 2014, 67 pages.
Gundlach, J.H., et al., "MSP Nanopores and Related Methods," U.S. Pat. No. 8,673,550, issued Mar. 18, 2014, "Patent Owners' Preliminary Response," *Oxford Nanopore Technologies, Ltd.* v. *The University of Washington and the UAB Research Foundation*, Before the U.S. Patent Trial and Appeal Board, Case No. IPR2014-00512, served Jun. 27, 2014, 20 pages.
Gundlach, J.H., et al., "MSP Nanopores and Related Methods," U.S. Pat. No. 8,673,550, issued Mar. 18, 2014, "Petition for Inter Partes Review of U.S. Pat. No. 8,673,550 Under 35 U.S.C. §§ 311-319 and 37 C.F.R. §§ 42.100 et seq." to the U.S. Patent Trial and Appeal Board, Case No. IPR2014-00513, served Mar. 18, 2014, 69 pages.
Gunderlach, J.H., et al., "MSP Nanopores and Related Methods," U.S. Pat. No. 8,673,550, issued Mar. 18, 2014, "Patent Owners' Preliminary Response," *Oxford Nanopore Technologies, Ltd.* v. *The University of Washington and the UAB Research Foundation*, Before the U.S. Patent Trial and Appeal Board, Case No. IPR2014-00513, served Jun. 27, 2014, 35 pages.
Gundlach, J.H., et al., "MSP Nanopores and Related Methods," U.S. Pat. No. 8,673,550, issued Mar. 18, 2014, "Petition for Inter Partes Review of U.S. Pat. No. 8,673,550 Under 35 U.S.C. §§ 311-319 and 37 C.F.R. §§ 42.100 et seq." to the U.S. Patent Trial and Appeal Board, Case No. IPR2015-00057, served Oct. 13, 2014, 64 pages.
Gundlach, J.H., et al., "MSP Nanopores and Related Methods," U.S. Pat. No. 8,673,550, issued Mar. 18, 2014, "Motion for Joinder and/or Consolidation With Related Instituted Inter Partes Review" to the U.S. Patent Trial and Appeal Board, Case No. IPR2015-00057, served Oct. 13, 2014, 11 pages.
Gyarfas, B., et al., "Mapping the Position of DNA Polymerase-Bound DNA Templates in a Nanopore at 5 Å Resolution," ACS Nano 3(6):1457-1466, Jun. 2009.
Hanss, B., et al., "Identification and Characterization of a Cell Membrane Nucleic Acid Channel," PNAS USA 95:1921-1926, 1998, Exhibit 1062 Submitted Aug. 28, 2015, in *Oxford Nanopore Technologies Ltd.* v. *University of Washington and UAB Research Foundation*, Before the U.S. Patent Trial and Appeal Board, Case No. IPR2014-00513, 6 pages.
Heger, M., "Pre-Print Study Demonstrates Nanopore Sequencing of Bacteriophage Genome With MspA Pore," www.genomeweb.com,

(56) References Cited

OTHER PUBLICATIONS

Jun. 24, 2014, pp. 1-4, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 4 pages.
Heger, M., "Proof-of-Principle Study Shows MspA Is Superior to Alpha-Hemolysin for Protein Nanopore Sequencing," www.genomeweb.com, Aug. 24, 2010, pp. 1-4, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and Uab Research Foundation*, 4 pages.
Heins, L., et al., "The Preprotein Conducting Channel at the Inner Envelope Membrane of Plastids," EMBO Journal 21(11):2616-2625, Jun. 2002.
Heinz, C., and M. Niederweis, "Selective Extraction and Purification of a Mycobacterial Outer Membrane Protein," Analytical Biochemistry 285(1):113-120, Oct. 2000.
Heinz, C., et al., "Mycobacterial Porins—New Channel Proteins in Unique Membranes," Conference of the German Society of Biochemistry 2005, <http://www.vetmed.uni-giessen.de:80/pharmtox/veranstaltungen/rauisch_05/abstracts.pdf> as of Dec. 17, 2005, exhibit cited in U.S. Patent Trial and Appeal Board Case No. IPR2014-00512 and Case No. IPR2014-00513, 1-page abstract.
Heinz, C., et al., "The Core of the Tetrameric Mycobacterial Porin MspA Is an Extremely Stable β-Sheet Domain," Journal of Biological Chemistry 278(10):8678-8685, Mar. 2003.
Hoffman, C., et al., "Disclosure of the Mycobacterial Outer Membrane: Cryo-Electron Tomography and Vitreous Sections Reveal the Lipid Bilayer Structure," PNAS 105(10):3963-3967, Mar. 2008.
Hoffmann, C., "Construction and Functional Analysis of Constriction Zone Mutants of *Mycobacterium smegmatis* Porin A (MspA)," thesis, University of Erlangen-Nuremberg, Germany, Oct. 2005, 115 pages.
Hornblower, B., et al., "Single-Molecule Analysis of DNA-Protein Complexes Using Nanopores," Nature Methods 4(4):315-317, Apr. 2007, exhibit cited in U.S. Patent Trial and Appeal Board, Case No. IPR2014-00512 and Case No. IPR2014-00513.
Howorka, S., and H. Bayley, "Probing Distance and Electrical Potential Within a Protein Pore With Tethered DNA," Biophysical Journal 83(6):3202-3210, Dec. 2002.
Howorka, S., et al., "Sequence-Specific Detection of Individual DNA Strands Using Engineered Nanopores," Nature Biotechnology 19(7):636-639, Jul. 2001, exhibit cited in U.S. Patent Trial and Appeal Board Case No. IPR2014-00512 and Case No. IPR2014-00513.
Huff, J., et al., "Functions of the Periplasmic Loop of the Porin MspA From *Mycobacterium smegmatis*," Journal of Biological Chemistry 284(15):10223-10231, Apr. 2009.
International Patent Application No. PCT/US2009/057915, filed Sep. 22, 2009, exhibit cited in U.S. Patent Trial and Appeal Board Case No. IPR2015-00057, 143 pages.
International Publication No. WO 2015/110777 A1, published Jul. 30, 2015, cited in U.S.D.C., Southern District of California, Case No. 3:16-cv-00477-LAB-MDD, as exhibit 21, and cited in International Trade Commission, Investigation No. 337-3123, as exhibit 91, 92 pages.
International Publication No. WO 2015/110813 A1, published Jul. 30, 2015, cited in U.S.D.C., Southern District of California, Case No. 3:16-cv-00477-LAB-MDD, as exhibit 20, and cited in ITC, Investigation No. 337-3123, as exhibit 90, 113 pages.
International Search Report and Written Opinion dated Aug. 18, 2010, issued in corresponding International Application No. PCT/US2009/057915, filed Sep. 22, 2009, 12 pages.
Jain, M., et al., "Improved Data Analysis for the MinION Nanopore Sequencer," Nature Methods 12(4):351-356, Apr. 2015, exhibit submitted Jun. 29, 2015, in support of Patent Owners' Supplemental Response for U.S. Patent Trial and Appeal Board, Case No.

IPR2014-00513, *Oxford Nanopore Technologies Ltd.* v. *University of Washington and UAB Research Foundation*, 9 pages.
Jayasinghe, L., and H. Bayley, "The Leukocidin Pore: Evidence for an Octamer With Four LukF Subunits and Four LukS Subunits Alternating Around a Central Axis," Protein Science 14(10):2550-2561, Oct. 2005.
Jennifer Harris Aug. 14, 2007 Email, Exhibit 1046, submitted Mar. 11, 2015, in support of Petitioner's Reply Patent Owners' Response in U.S. Patent Trial and Appeal Board Case No. IPR2014-00513, *Oxford Nanopore Technologies, Ltd.* v. *The University of Washington and the UAB Research Foundation*, 2 pages.
Jennifer Harris Aug. 8, 2007 Email, Exhibit 1047, submitted Mar. 11, 2015, in support of Petitioner's Reply to Patent Owners' Response in U.S. Patent Trial and Appeal Board Case No. IPR2014-00513, *Oxford Nanopore Technologies, Ltd.* v. *The University of Washington and the UAB Research Foundation*, 2 pages.
Jennifer Harris Aug. 14, 2007 Email, Exhibit 1048, submitted Mar. 11, 2015, in support of Petitioner's Reply to Patent Owners' Response in U.S. Patent Trial and Appeal Board Case No. IPR2014-00513, *Oxford Nanopore Technologies, Ltd.* v. *The University of Washington and the UAB Research Foundation*, 1 page.
Sanghera, G., E-mail dated Feb. 4, 2011, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 1 page.
Stahl, C., et al., "MspA Provides the Main Hydrophilic Pathway Through the Cell Wall of *Mycobacterium smegmatis*," Molecular Microbiology 40(2):451-464, Apr. 2001.
Stefureac, R., et al., "Transport of α-Helical Peptides through α-Hemolysin and Aerolysin Pores," Biochemistry 45:9172-9179, 2006, Exhibit 1063 Submitted Aug. 28, 2015, in *Oxford Nanopore Technologies Ltd.* v. *University of Washington and UAB Research Foundation*, Before the U.S. Patent Trial and Appeal Board, Case No. IPR2014-00513, 8 pages.
Stephan, J., et al., "The Growth Rate of Mycobacterium smegmatis Depends on Sufficient Porin-Mediated Influx of Nutrients," Molecular Microbiology 58(3):714-730, Nov. 2005.
Stoddart, D., et al., "Single-Nucleotide Discrimination in Immobilized DNA Oligonucleotides With a Biological Nanopore," Proceedings of the National Academy of Sciences of the United States of America (PNAS) 106(19):7702-7707, May 2009.
Supplemental Declaration of Daniel Branton, Exhibit 1052 in U.S. Patent Trial and Appeal Board Case No. IPR2014-00513, *Oxford Nanopore Technologies, Ltd.* v. *The University of Washington and The UAB Research Foundation*, Apr. 1, 2015, 9 pages.
Szabò, I., et al., "DNA Translocation Across Planar Bilayers Containing Bacillus subtilis Ion Channels," J Biol Chem 272(40):25275-25282, 1997, Exhibit 1061 submitted Aug. 28, 2015, in *Oxford Nanopore Technologies Ltd.* v. *University of Washington and UAB Research Foundation*, Before the U.S. Patent Trial and Appeal Board, Case No. IPR2014-00513, 9 pages.
Szabò, I., et al., "Double-Stranded DNA Can Be Translocated Across a Planar Membrane Containing Purified Mitochondrial Porin," FASEB, 12:495-502, 1998, Exhibit 1060 Submitted Aug. 28, 2015, in *Oxford Nanopore Technologies Ltd.* v. *University of Washington and UAB Research Foundation*, Before the U.S. Patent Trial and Appeal Board, Case No. IPR2014-00513, 8 pages.
Tamm, L.K., et al., "Folding and Assembly of β-barrel Membrane Proteins," Biochimica et Biophysica Acta 1 666(1-2):250-263, Nov. 2004.
"Through Constriction to a Wide Open Frontier," University of Washington Physics Newsletter 15:6, Nov. 2007, 1 page.
Timp, W., et al., "Think Small: Nanopores for Sensing and Synthesis," IEEE Access 2:1396-1408, 2014, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 13 pages.
Trias, J., and R. Benz, "Characterization of the Channel Formed by the Mycobacterial Porin in Lipid Bilayer Membranes," Journal of

(56) References Cited

OTHER PUBLICATIONS

Biological Chemistry 268(9):6234-6240, Mar. 1993, exhibit cited in U.S. Patent Trial and Appeal Board Case No. IPR2014-00512 and Case No. IPR2014-00513.

Trias, J., and R. Benz, "Permeability of the Cell Wall of *Mycobacterium smegmatis*," Molecular Microbiology 14(2):283-290, Oct. 1994, exhibit cited in U.S. Patent Trial and Appeal Board Case No. IPR2014-00512 and Case No. IPR2014-00513.

Trias, J., et al., "Porins in the Cell Wall of Mycobacteria," Science 258(5087):1479-1481, Nov. 1992.

U.S. Provisional Patent Application No. 61/098,938, filed Sep. 22, 2008, exhibit cited in U.S. Patent Trial and Appeal Board Case No. IPR2015-00057, 33 pages.

University of Washington Receives $1 Million Grant From Amgen Foundation for Undergraduate Science Research Program, Oct. 16, 2006 press release [retrieved Jan. 29, 2015], Exhibit 3 to the Deposition of Jennifer Harris in U.S. Patent Trial and Appeal Board Case No. IPR2014-00513, *Oxford Nanopore Technologies, Ltd.* v. *The University of Washington and the UAB Research Foundation*, Feb. 3, 2015, 3 pages.

University of Washington Response to Baker Botts LLP, "Public Records Request PR-2014-00281(Stage 1)," Nov. 18, 2014, and Jens Gundlach May 5, 2011 Email, Exhibit 1050, submitted Mar. 11, 2015, in support of Petitioners Reply to Patent Owners' Response in U.S. Patent Trial and Appeal Board Case No. IPR2014-00513, *Oxford Nanopore Technologies, Ltd.* v. *The University of Washington and the UAB Research Foundation*, 3 pages.

Venkatesan, B.M., and R. Bashir, "Nanopore Sensors for Nucleic Acid Analysis," Nature Nanotechnology 6 (10):615-624, Sep. 2011, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 10 pages.

Vercoutere, W., et al., "Rapid Discrimination Among Individual DNA Hairpin Molecules at Single-Nucleotide Resolution Using an Ion Channel," Nature Biotechnology 19(3):248-252, Mar. 2001, exhibit cited in U.S. Patent Trial and Appeal Board Case No. IPR2014-00512 and Case No. IPR2014-00513.

Vercoutere, W.A., et al., "Discrimination Among Individual Watson-Crick Base Pairs at the Termini of Single DNA Hairpin Molecules," Nucleic Acids Research 31(4):1311-1318, Feb. 2003, exhibit cited in U.S. Patent Trial and Appeal Board Case No. IPR2014-00512 and Case No. IPR2014-00513.

Wang, H., and D. Branton, "Nanopores With a Spark for Single-Molecule Detection," Nature Biotechnology 19 (7):622-623, Jul. 2001, exhibit cited in U.S. Patent Trial and Appeal Board Case No. IPR2014-00512 and Case No. IPR2014-00513.

Wang, H., et al., "DNA Heterogeneity and Phosphorylation Unveiled by Single-Molecule Electrophoresis," Proceedings of the National Academy of Science USA (PNAS) 101(37):13472-13477, Sep. 2004, exhibit cited in U.S. Patent Trial and Appeal Board Case No. IPR2014-00512 and Case No. IPR2014-00513.

Willcocks, S., E-mail dated Apr. 10, 2009, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 3 pages.

Willcocks, S., E-mail dated Jul. 1, 2009, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 2 pages.

WO 2012/107778, filed Feb. 11, 2011 (priority date), by ONT entitled "Mutant Pores," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 110 pages.

WO 2013/014451, filed Jul. 25, 2011 (priority date), by ONT entitled "Hairpin Loop Method for Double Strand Polynucleotide Sequencing Using Transmembrane Pores," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 92 pages.

WO 2013/057495, filed Oct. 21, 2011 (priority date), by ONT entitled "Method of Characterizing a Target Polynucleotide Using a Pore and a heI308 Helicase," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 110 pages.

WO 2013/098562, filed Dec. 29, 2011 (priority date), by ONT entitled "Enzyme Method," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 89 pages.

WO 2014/135838, filed Mar. 8, 2013 (priority date), by ONT entitled "Enzyme Stalling Method," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 109 pages.

WO 2015/055981, filed Oct. 18, 2013 (priority date), by ONT entitled "Modified Enzymes," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 146 pages.

WO 2015/056028, filed Oct. 18, 2013 (priority date), by ONT entitled "Method of Characterizing a Target Ribonucleic Acid (RNA) Comprising Forming a Complementary Polynucleolide Which Moves Through a Transmembrane Pore," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 67 pages.

Wong, R., "Engineering *Mycobacterium smegmatis* Porin A (MspA) for DNA Analysis," University of Washington Summer Research Poster Session, pamphlet cover, program description, schedule of events, abstract and poster, presentation date Aug. 16, 2007, 5 pages.

Wörner, M., et al., "Characterization of Nanostructured Surfaces Generated by Reconstitution of the Porin MspA From *Mycobacterium smegmatis*," Small 3(6):1084-1097, Jun. 2007.

Zhou, Y., et al. "Human $\alpha 4\beta 2$ Acetylcholine Receptors Formed From Linked Subunits," Journal of Neuroscience 23(27):9004-9015, Oct. 2003.

Communication Pursuant to Article 94(3) EPC dated Jan. 2, 2018, in European Patent Application No. 15202190.3, filed Sep. 22, 2009, 3 pages.

```
MspA  MKAISRVLIAMV---AAIAALFTSTGTSHAGLDNELSLVDGQDRTLTVQQWDTFLNGVFPLDRNRLTREW  40
MspB  M AE RVLIAM  SAT AG      GTSHAGLDNELSLVDGQDRTLTVQQWDTFLNGVFPLDRNRLTREW  40
MspC  MKAISRVLIAM  SAT AEL S   GTSHAGLDNELSLVDGQDRTLTVQQWDTFLNGVFPLDRNRLTREW  40
MspD  MA A V      AAVAELFS  AM V    A    LS V    ERTLTVQ  ETFLNGVFPLDRNRLTREW  39

MspA  FHSGRAKYIVAGPGADEFEGTLELGYQIGFPWSLGVGINFSYTTPNILIDDGDITAPPFGLNSVITPNLF  110
MspB  FHSGRAKYIVAGPGADEFEGTLELGYQIGFPWSLGVGINFSYTTPNILIDDGDITAPPFGLNSVITPNLF  110
MspC  FHSGRAKYIVAGPGADEFEGTLELGYQIGFPWSLGVGINFSYTTPNILIDDGDIT PPFGL SVITPNLF  110
MspD  FHSGRA YE VAGPGADEFEGTLELGYQ GFPWSLGVGINFSYTTPNILIDDGDIT PPFGL D TTPNLF  109

MspA  PGVSISADLGNGPGIQEVATFSVDVSGAEGGVAVSNAHGTVTGAAGGVLLRPFARLIASTGDSVTTYGEPWNMN  184
MspB  PGVSISADLGNGPGIQEVATFSVDVSGVSG  GGVAVSNAHGTVTGAAGGVLLRPFARLIASTGDSVTTYGEPWNMN  184
MspC  PGVSISADLGNGPGIQEVATFSVDVSG SG GGVAVSNAHGTVTGAAGGVLLRPFARLIASTGDSVTTYGEPWNMN  184
MspD  PGVSISADLGNGPGIQEVATFSVDV G G VAVSNAHGTVTGAAGGVLLRPFARLIASTGDSVTTYGEPWNMN  183
```

FIGURE 18

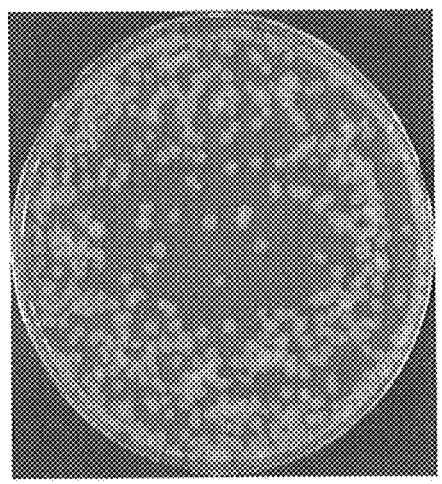
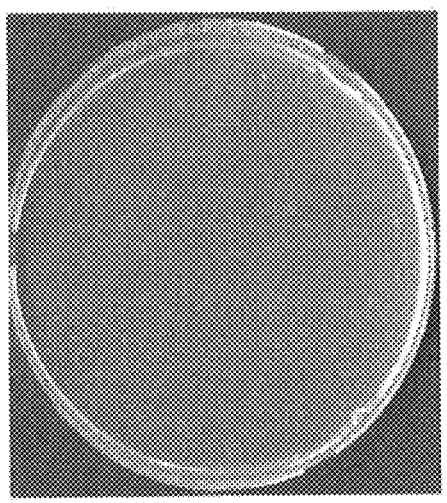
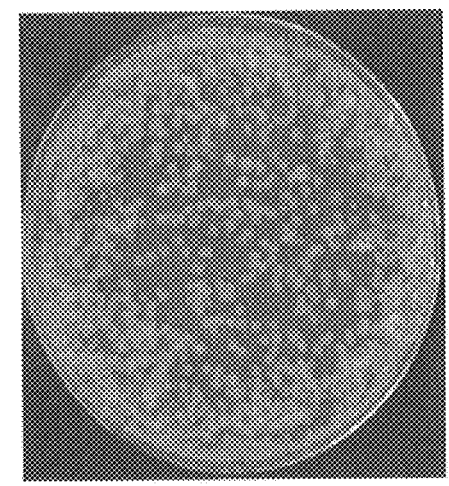
FIGURE 23

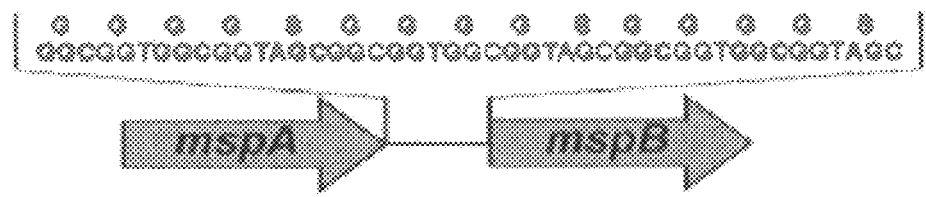
FIGURE 26B
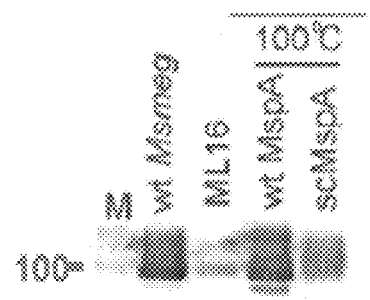
FIGURE 26C

FIGURE 30

MSP NANOPORES AND RELATED METHODS

CROSS-REFERENCES TO RELATED APPLICATIONS

This application is a division of application Ser. No. 14/318,072, filed Jun. 27, 2014 (now U.S. Pat. No. 9,624,275), which is a continuation of application Ser. No. 14/215,871, filed Mar. 17, 2014, now U.S. Pat. No. 9,170,230, which is a continuation of application Ser. No. 13/069,187, filed Mar. 22, 2011, now U.S. Pat. No. 8,673,550, which is a continuation of International Patent Application No. PCT/US2009/057915, filed Sep. 22, 2009, which claims the benefit of Provisional Application No. 61/098,938, filed Sep. 22, 2008, all of which are incorporated herein by reference in their entirety.

STATEMENT OF GOVERNMENT LICENSE RIGHTS

This invention was made with Government support under Grant No. 1 R21 HG004145-01 awarded by the National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 57952_Seq_Final_2017-04-14.txt. The text file is 51 KB; was created on Apr. 14, 2017; and is being submitted via EFS-Web with the filing of the specification.

BACKGROUND

Established DNA sequencing technologies require substantial amounts of DNA and several lengthy steps to construct just several tens of bases out of the full sequence. This information must then be assembled "shotgun" style, an effort that depends non-linearly on the size of the genome and on the length of the fragments from which the full genome is constructed. These steps are expensive and time-consuming, especially when sequencing mammalian genomes.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Provided herein is a method comprising applying an electric field to a *Mycobacterium smegmatis* porin (Msp) porin having a vestibule and a constriction zone that define a tunnel, wherein the Msp porin is positioned between a first conductive liquid medium and a second conductive liquid medium.

Also provided is a method of modifying the conductance through the tunnel of an Msp porin comprising removing, adding, or replacing at least one amino acid in the vestibule or the constriction zone of a wild-type Msp porin.

A system comprising an Msp porin having a vestibule and a constriction zone that define a tunnel is also provided, wherein the tunnel is positioned between a first liquid medium and a second liquid medium, wherein at least one liquid medium comprises an analyte, and wherein the system is operative to detect a property of the analyte.

Further provided is a system comprising an Msp porin having a vestibule and a constriction zone that define a tunnel, wherein the tunnel is positioned in a lipid bilayer between a first liquid medium and a second liquid medium, and wherein the only point of liquid communication between the first and second liquid media occurs in the tunnel.

Mutant Msp porins are also provided. For example, a mutant *Mycobacterium smegmatis* porin A (MspA) porin is provided comprising a vestibule and a constriction zone that define a tunnel, and at least a first mutant MspA monomer comprising a mutation at position 93 and a mutation at position 90, position 91, or both positions 90 and 91. Also provided is a mutant MspA porin comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel, and further comprising at least a first mutant MspA paralog or homolog monomer. Also provided is a mutant MspA paralog or homolog comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel.

Methods of making mutant Msp porins are described. For example, provided herein is a method of making a mutant MspA porin, comprising modifying a wild-type MspA monomer at position 93 and at position 90, position 91, or both positions 90 and 91. Also provided is a method of making a mutant MspA porin having a vestibule and a constriction zone that define a tunnel, comprising deleting, adding, or replacing any amino acid in the vestibule or the constriction zone of a wild-type MspA paralog or homolog monomer such that the resulting mutant MspA porin is capable of translocating an analyte through the tunnel upon application of an electric field.

Also provided is a method comprising translocating an analyte through a tunnel of a *Mycobacterium smegmatis* porin (Msp) porin without employing an electric field.

Nucleic acid sequences are provided herein. Optionally, a nucleic acid sequence may comprise a first and second nucleotide sequence, wherein the first nucleotide sequence encodes a first Msp monomer sequence and the second nucleotide sequence encodes a second Msp monomer sequence. The nucleic acid sequence may further comprise a third nucleotide sequence encoding an amino acid linker sequence. Optionally, the nucleic acid sequence further comprises a third or more nucleotide sequence encoding a third or more Msp monomer sequence. For example, the nucleic acid sequence may further comprise a third, fourth, fifth, sixth, seventh, and eighth nucleotide sequence. The first, second, third, fourth, fifth, sixth, seventh, and eighth nucleotide sequences encode a first, second, third, fourth, fifth, sixth, seventh, and eighth Msp monomer sequence, and the nucleic acid sequence further comprises a ninth nucleotide sequence encoding an amino acid linker sequence. Also provided are Msp porins comprising two or more single-chain Msps.

Polypeptides encoded by nucleic acids described herein are also provided. Vectors comprising polypeptides described herein are also provided. Cultured cells transfected with any vector described herein, or progeny thereof, wherein the cell is capable of expressing an Msp porin or Msp porin monomer, are also provided. A *Mycobacterium smegmatis* strain comprising any vector described herein is also provided.

Also provided is a mutant bacterial strain capable of inducible Msp monomer expression, the bacterial strain comprising (a) a deletion of a wild-type MspA; (b) a deletion of a wild-type MspC; (c) a deletion of a wild-type MspD; and (d) a vector comprising an inducible promoter operably linked to an Msp monomer nucleic acid sequence.

A method of producing a single-chain Msp porin is also provided, the method comprising (a) transforming a mutant bacterial strain with a vector comprising a nucleic acid sequence capable of encoding a single-chain Msp porin; and optionally (b) purifying the single-chain Msp porin from the bacteria. The mutant strain may include deletions of a wild-type MspA, a wild-type MspB, a wild-type MspC, and a wild-type MspD, and a vector comprising an inducible promoter operably linked to an Msp nucleic acid sequence. The mutant strain may be transformed with a vector comprising a nucleic acid sequence capable of encoding a single-chain Msp porin.

Further provided are methods of using Msp porins, such as a single-chain Msp porin. For example, the method may comprise creating a lipid bilayer having a first side and second side, adding an Msp porin, such as a purified single-chain Msp porin, to the first side of the lipid bilayer, applying positive voltage to the second side of the bilayer, translocating an experimental nucleic acid sequence or polypeptide sequence through the Msp porin, measuring the blockade current of the translocating sequence passed through the Msp porin, and comparing the experimental blockade current with a blockade current standard and determining the experimental sequence.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A is a schematic diagram of experiments. FIG. 3B shows representative ionic current signals observed for WTMspA porins at 60 mV (Left) and 100 mV (Right) with no DNA present. Intervals of negative current flow correspond to reversal of the applied voltage, which was often required to reestablish the unblocked ionic current level.

FIG. 5A is a schematic diagram of experiments. FIG. 5B shows representative ionic current signal observed for M1MspA porins in the absence of DNA and the presence of 8 µM hp08 (SEQ ID NO:4) hairpin DNA at 180 and 140 mV. FIG. 5C shows numbered blockades from traces in FIG. 5B at expanded time scales.

FIG. 9A shows animation of molecular configurations: (1) an unblocked pore; (2) a threaded ssDNA with neutravidin (nA) arresting translocation of the nAssDNA complex; (3) target DNA hybridized with nA-ssDNA disassociating at negative voltage; and (4) the nA-ssDNA complex exiting from the pore at a voltage depending on the hybridization of the target DNA. FIG. 9B is a time series of the applied voltage. A current blockade triggers a change from the 180 mV capture voltage to a holding voltage of 40 mV after delay of ~200 ms. The holding voltage is maintained for 5 seconds to allow hybridization, and is then ramped negatively. FIGS. 9C and 9D each show current time series demonstrating nA-ssDNA exit at negative and positive voltages, respectively. Large current spikes occur because of instantaneous voltage changes and spontaneous pore closure at large negative voltage. FIGS. 9E-9G are exit voltage ($V_{exit}$) histograms. FIG. 9E shows an experiment where the probe, 5'-$C_6A_{54}$-CTCTATTCT-TATCTC-3' (SEQ ID NO:7, was complementary to the target ssDNA molecules, 5'-GAGATAAGAATAGAG-3' (SEQ ID NO:9). FIG. 9F shows the same pore as in FIG. 9E, but with a probe, 5'-$C_6A_{54}$-CACACACACACACAC-3' (SEQ ID NO:8), that is not complementary to the target DNA. FIG. 9G shows results from a separate control using the same probe (SEQ ID NO:7) as in FIG. 9E, but without target DNA present in the trans compartment. A significant number of negative $V_{exit}$ events are observed only in FIG. 9E, where the probe (SEQ ID NO:7) is complementary to the target. The infrequent occurrence of negative $V_{exit}$ events in FIGS. 9F and 9G rule out the possibility that a majority of negative $V_{exit}$ in FIG. 9E is caused by nonspecific probe-target association or by binding of the probe to the pore.

FIG. 10A is a schematic diagram of experiments. FIG. 10B shows representative ionic current signals observed for the M1MspA porin with 8 µM $dT_{50}$ (Left) and the M2MspA porin with 2 µM $dT_{50}$ (Right). FIG. 10C shows numbered blockades from traces in FIG. 10B at expanded time scales.

FIG. 15A presents the expression level of this mutant. All proteins were expressed in ML16 M. smegmatis. 10 µl of 0.5% octylpolyoxyethylene raw extract was loaded in each well. Lane 1: WTMspA; Lane 2: background (pMS2, empty vector); Lane 3: M2-QQN (pML866). FIG. 15B shows current traces of the M2-QQN porin in a diphytanoylphosphatidylcholine lipid bilayer that were recorded in 1 M KCl. Approximately 70 mg of protein was added to the bilayer chamber. Approximately 100 pores of four membranes were analyzed in lipid bilayer experiments. The main conductance of the M2-QQN porin is 2.4 nanoseconds (nS).

FIG. 18 shows an alignment of MspA, MspB, MspC, and MspD monomers of M. smegmatis. The first ATG or GTG codon of the open reading frames were taken as the putative start codon. The numbering of the protein starts with the first amino acid of the mature part. The MspA monomer amino acid sequence is SEQ ID NO:28, the MspB monomer amino acid sequence is SEQ ID NO:29, the MspC monomer amino acid sequence is SEQ ID NO:30, and the MspD monomer amino acid sequence is SEQ ID NO:31.

FIG. 21A is the integrative plasmid map for the expression of MspA. AmiC, A, D, S are required for the acetamide-inducible expression of MspA. attP: chromosome attachment site of the phage L5; int: L5 integrase; FRT: Flp recombinase site. FIG. 21B is the plasmid map for the MspB deletion vector. MspBup, MspBdown: regions upstream and downstream of MspB; loxP: Cre recombination site; SacB: levansucrase; XylE: catechol-2,3-dioxygenase; Gfp2+: Green fluorescent protein; tsPAL5000: temperature-sensitive origin of replication for mycobacteria.

FIG. 23 is an image demonstrating the growth of the Msp quadruple mutant ML705 on Middlebrook 7H10 agar plates.

FIGS. 26A-26D shows the structure and tunnel activity of the single-chain MspA nanopore dimer. FIG. 26A is an image of the molecular model of the single-chain nanopore MspA dimer. FIG. 26B shows the scheme of the single-chain MspA nanopore dimer (scMspA) gene construct. The amino acid linker region $(GGGGS)_3$ (SEQ ID NO:3) is enlarged. The DNA sequence (5'-GGCGGTGGCGGTAGCGGCG-GTGGCGGTAGCGGCGGTGGCGGTAGC-3') (SEQ ID NO:19) of the amino acid linker is also shown. FIG. 26C is an image of a Western blot demonstrating the expression of the scMspA nanopore dimer in *M. smegmatis*. Lane 1 is the molecular mass marker (M), lane 2 is the wild-type *M. smegmatis* (WT Msmeg), lane 3 is the ML16 strain without the scMspA gene construct (ML16), lane 4 is the ML16 strain with a wild-type MspA gene construct (WTMspA), and lane 5 is the ML16 strain with the scMspA nanopore dimer gene construct (scMspA). FIG. 26D shows a current trace for the scMspA nanopore dimer.

Figure 30:
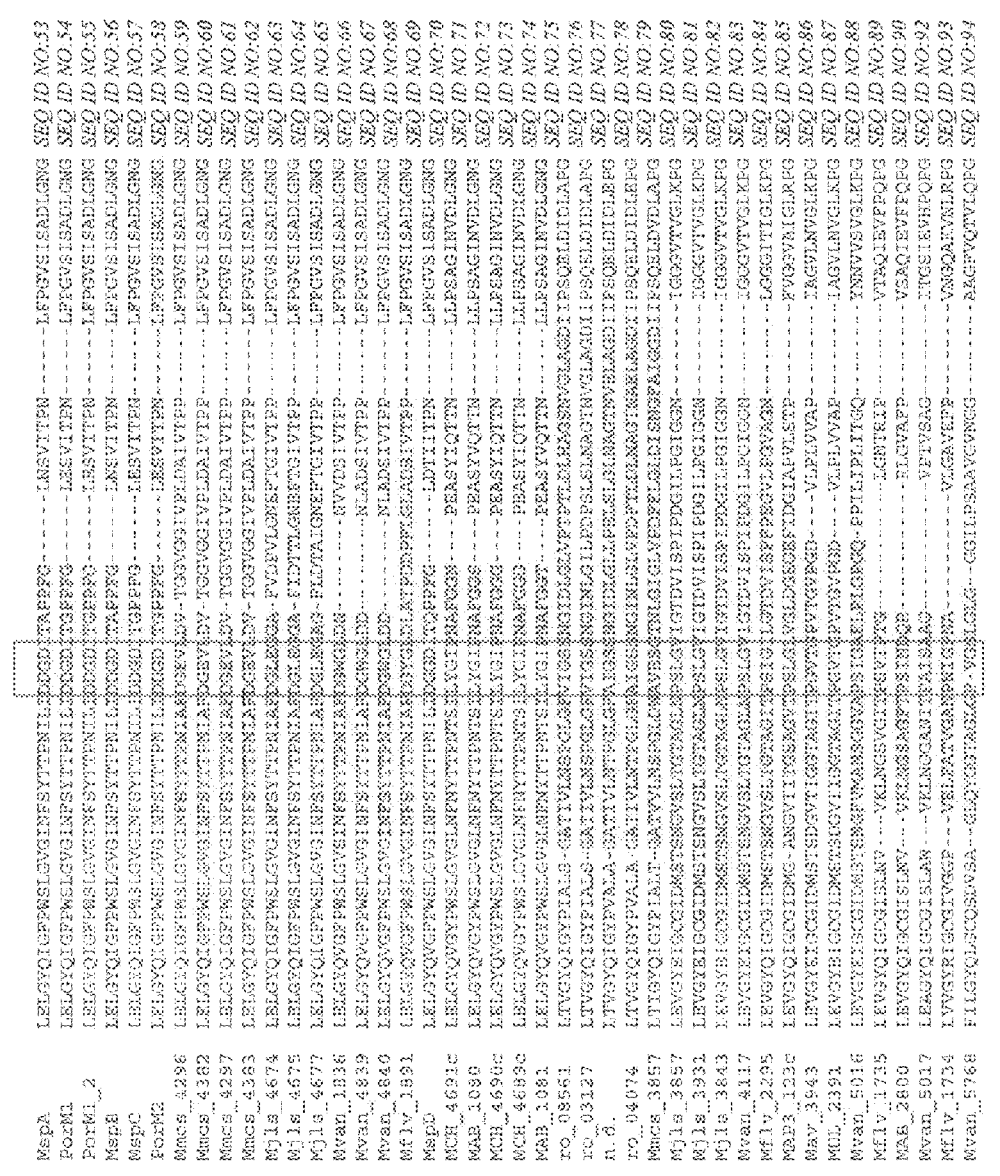

FIG. 30 shows the constriction zone (the rectangular box) of a wild-type MspA monomer and a variety of MspA paralog and homolog monomers.

DETAILED DESCRIPTION

Figure 1:
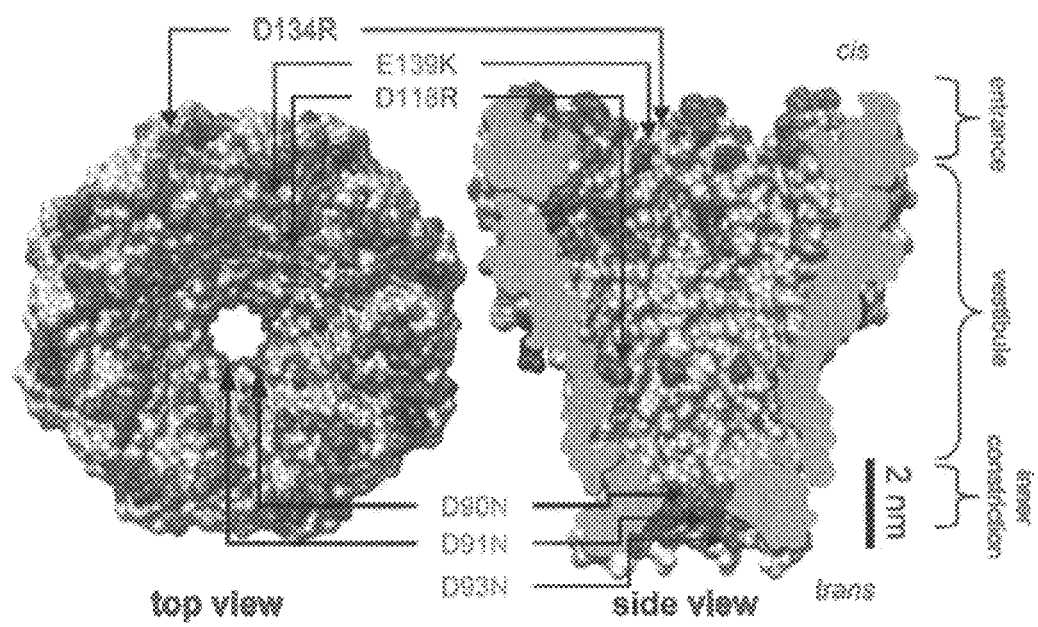
FIG. 1 shows the structure and charge distribution of wild-type MspA (WTMspA) porin. At pH 8, acidic residues are expected to be predominantly negatively charged and the basic residues to be positively charges. Locations and identities of mutation are indicated by arrows and labels. See Faller et al., *Science*, 303:1189 (2004).

Provided herein is a method comprising applying an electric field to a *Mycobacterium smegmatis* porin (Msp) porin having a vestibule and a constriction zone that define a tunnel, wherein the Msp porin is positioned between a first conductive liquid medium and a second conductive liquid medium. Optionally, the first and second liquid conductive media are the same. Optionally, the first and second liquid conductive media are different. The Msp porin may be any Msp porin discussed herein. For example, the Msp porin may be selected from the group consisting of a wild-type MspA porin, a mutant MspA porin, a wild-type MspA paralog or homolog porin, and a mutant MspA paralog or homolog porin.

In any embodiment herein, an Msp porin may further comprise a molecular motor. The molecular motor may be capable of moving an analyte into or through a tunnel with a translocation velocity or an average translocation velocity that is less than the translocation velocity or average translocation velocity at which the analyte electrophoretically translocates into or through the tunnel in the absence of the molecular motor. Accordingly, in any embodiment herein comprising application of an electric field, the electric field may be sufficient to cause the analyte to electrophoretically translocate through the tunnel.

Any liquid medium discussed herein, such as a conductive liquid medium, may comprise an analyte. The analyte may be any analyte discussed herein. Embodiments herein may further comprise detecting the analyte, such as in a method comprising measuring an ion current as the analyte interacts with an Msp porin tunnel to provide a current pattern, wherein the appearance of a blockade in the current pattern indicates the presence of the analyte.

Optionally, an Msp porin is a mutant MspA or mutant MspA paralog or homolog porin, and the analyte has a translocation velocity or an average translocation velocity through the porin tunnel that is less than, or is greater than, the translocation velocity or the average translocation velocity of the analyte through the tunnel of a wild-type MspA or a wild-type MspA paralog or homolog porin.

In any embodiment herein, an analyte may have a translocation velocity or an average translocation velocity through a tunnel of less than 0.5 nm/μs. Optionally, an analyte may have a translocation velocity or an average translocation velocity through a tunnel of less than 0.05 nm/μs.

Any Msp porin discussed herein may be comprised in a lipid bilayer. In such embodiments or any other embodiment herein, the Msp porin may have a cis side and a trans side. Optionally, an analyte electrophoretically or otherwise translocates from the cis side through a tunnel to the trans side. Optionally, an analyte electrophoretically or otherwise translocates from the trans side through a tunnel to the cis side. Optionally, an analyte is electrophoretically or otherwise driven from the cis side or the trans side into a tunnel and stays in the tunnel or then retracts to the cis side or the trans side, respectively.

Any embodiment herein may further comprise identifying an analyte. Such methods may comprise comparing the current pattern obtained with respect to an unknown analyte to that of a known current pattern obtained using a known analyte under the same conditions.

In any embodiment herein, an analyte may be a nucleotide, a nucleic acid, an amino acid, a peptide, a protein, a polymer, a drug, an ion, a pollutant, a nanoscopic object, or a biological warfare agent. Optionally, an analyte is a polymer, such as a protein, a peptide, or a nucleic acid. Optionally, the polymer is a nucleic acid. Optionally, a nucleic acid has a translocation velocity or an average translocation velocity through a tunnel of less than 1 nucleotide/μs. Optionally, a nucleic acid has a translocation velocity or an average translocation velocity through the tunnel of less than 0.1 nucleotide/μs. A nucleic acid may be ssDNA, dsDNA, RNA, or a combination thereof.

Embodiments herein may comprise distinguishing at least a first unit within a polymer from at least a second unit within the polymer. Distinguishing may comprise measuring the ion current produced as the first and second units separately translocate through a tunnel to produce a first and a second current pattern, respectively, where the first and second current patterns differ from each other.

Embodiments herein may further comprise sequencing a polymer. Sequencing may comprise measuring the ion current or optical signals as each unit of the polymer is separately translocated through the tunnel to provide a current pattern that is associated with each unit, and comparing each current pattern to the current pattern of a known unit obtained under the same conditions, such that the polymer is sequenced.

Any embodiment herein may further comprise determining the concentration, size, molecular weight, shape, or orientation of an analyte, or any combination thereof. Any liquid medium discussed herein, such as a conductive liquid medium, may comprise a plurality of analytes. Any analyte described herein may comprise an optical bead or a magnetic bead.

Any Msp porin discussed herein may be further defined as a mutant MspA porin. A mutant MspA porin may comprise a vestibule and a constriction zone that define a tunnel, and at least a first mutant MspA monomer comprising a mutation at position 93, 91, 90, or any combination thereof. A mutant MspA porin may comprise a mutation at positions 93 and 91; positions 93 and 90; positions 91 and 90; or positions 93, 90, and 91. Optionally, a mutant MspA porin comprises one or more mutations at any of the following amino acid positions: 88, 105, 108, 118, 134, or 139, or any other mutation described herein.

In any embodiment herein, the diameter of a mutant MspA porin or mutant MspA paralog or homolog may be less than the diameter of the constriction zone of a corresponding wild-type MspA porin or wild-type MspA paralog or homolog. A mutant MspA porin or mutant MspA paralog or homolog may have a mutation in the vestibule or the constriction zone that permits an analyte to translocate, electrophoretically or otherwise, through the tunnel of the mutant MspA porin or mutant MspA paralog or homolog with a translocation velocity or an average translocation velocity that is less than the translocation velocity or average translocation velocity at which the analyte translocates through the tunnel of a wild-type Msp porin or wild-type MspA paralog or homolog.

A mutant Msp porin, such as a mutant MspA porin or a mutant MspA paralog or homolog porin, may comprise a neutral constriction zone. A mutant Msp porin, such as a mutant MspA porin or a mutant MspA paralog or homolog porin, may comprise a conductance through the tunnel that is higher, such as two-fold higher, than the conductance through the tunnel of its corresponding wild-type Msp porin. A mutant Msp porin, such as a mutant MspA porin or a mutant MspA paralog or homolog porin, may comprise a conductance through the tunnel that is lower than the conductance through the tunnel of its corresponding wild-type Msp porin.

Any Msp porin discussed herein may comprise a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. Also provided herein is a mutant MspA porin comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel, and further comprising at least a first mutant MspA paralog or homolog monomer.

The diameter of the constriction zone of a mutant Msp porin, such as a mutant MspA porin or mutant MspA paralog or homolog, may be less than the diameter of the constriction zone of its corresponding wild-type Msp porin, such as a wild-type MspA porin or wild-type MspA paralog or homolog. A mutant Msp porin, such as a mutant MspA porin or mutant MspA paralog or homolog, may comprise a mutation in the vestibule or the constriction zone that permits an analyte to translocate, electrophoretically or otherwise, through the tunnel of the porin with translocation velocity or an average translocation velocity that is less than the translocation velocity or average translocation velocity at which the analyte translocates through the tunnel of its corresponding wild-type Msp porin, (e.g., wild-type MspA porin, wild-type MspA paralog or homolog).

Optionally, an Msp porin is encoded in full or in part by a nucleic acid sequence encoding a partial or complete single-chain Msp porin, wherein the nucleic acid sequence comprises (a) a first and second nucleotide sequence, wherein the first nucleotide sequence encodes a first Msp monomer sequence and the second nucleotide sequence encodes a second Msp monomer sequence; and (b) a third nucleotide sequence encoding an amino acid linker sequence. The monomer sequences may be any monomer sequence described herein. Optionally, the first and second Msp monomer sequences are independently selected from the group consisting of a wild-type MspA monomer, a wild-type MspB monomer, a wild-type MspC monomer, a wild-type MspD monomer, and mutants thereof. Optionally, the first Msp monomer sequence comprises a wild-type MspA monomer or a mutant thereof. Optionally, the first Msp monomer sequence comprises a mutant MspA monomer.

In any embodiment herein, an Msp porin may be encoded in full or in part by a nucleic acid sequence encoding a partial or complete single-chain Msp porin, wherein the nucleic acid sequence comprises (a) a first, second, third, fourth, fifth, sixth, seventh, and eighth nucleotide sequence or any subset thereof, wherein the first, second, third, fourth, fifth, sixth, seventh, and eighth nucleotide sequences encode a first, second, third, fourth, fifth, sixth, seventh, and eighth Msp monomer sequence, respectively; and (b) a ninth nucleotide sequence encoding an amino acid linker sequence. Thus, the porin may comprise one or more partial single-chain Msp porins that hybridize, dimerize, trimerize, or the like with other Msp monomers or other partial single-chain Msp porins. Alternatively, the full single-chain Msp porin may form a porin without associating with other Msp elements. In any embodiment herein, for example, an Msp porin may be encoded by a nucleic acid sequence encoding a complete single-chain Msp porin, wherein the nucleic acid sequence comprises (a) a first, second, third, fourth, fifth, sixth, seventh, and eighth nucleotide sequence, wherein the first, second, third, fourth, fifth, sixth, seventh, and eighth nucleotide sequences encode a first, second, third, fourth, fifth, sixth, seventh, and eighth Msp monomer sequence, respectively; and (b) a ninth nucleotide sequence encoding an amino acid linker sequence. Each Msp monomer may comprise a wild-type MspA monomer or a mutant thereof. Optionally, at least one Msp monomer comprises a wild-type MspA monomer or a mutant thereof. Thus, the porin can be encoded in full.

In any embodiment herein, an Msp monomer may be a wild-type MspA paralog or homolog, such as MspA/Msmeg0965, MspB/Msmeg0520, MspC/Msmeg5483, MspD/Msmeg6057, MppA, PorM1, PorM2, Mmcs4296, Mmcs4297, Mmcs3857, Mmcs4382, Mmcs4383, Mjls3843, Mjls3857, Mjls3931 Mjls4674, Mjls4675, Mjls4677, Map3123c, Mav3943, Mvan1836, Mvan4117, Mvan4839, Mvan4840, Mvan5016, Mvan5017, Mvan5768, MUL_2391, Mflv1734, Mflv1735, Mflv2295, Mflv1891, MCH4691c, MCH4689c, MCH4690c, MAB1080, MAB1081, MAB2800, RHA1 ro08561, RHA1 ro04074, and RHA1 ro03127.

Also provided herein is a method of modifying the conductance through the tunnel of an Msp porin comprising removing, adding, or replacing at least one amino acid in the vestibule or the constriction zone of a wild-type Msp porin. For example, the method may comprise increasing the conductance. The method may comprise decreasing the conductance.

A method comprising translocating an analyte through a tunnel of an Msp porin without employing an electric field is also provided. In this or any other embodiment herein, an Msp porin may further comprise a molecular motor. The Msp porin may be any Msp porin described herein, such as a wild-type MspA porin, a mutant MspA porin, a wild-type MspA paralog or homolog porin, and a mutant MspA paralog or homolog porin. The Msp porin may be encoded by a nucleic acid sequence encoding a single-chain Msp porin.

Also provided is a system comprising an Msp porin having a vestibule and a constriction zone that define a tunnel, wherein the tunnel is positioned between a first liquid medium and a second liquid medium, wherein at least one liquid medium comprises an analyte, and wherein the system is operative to detect a property of the analyte. A system may be operative to detect a property of any analyte comprising subjecting an Msp porin to an electric field such that the analyte interacts with the Msp porin. A system may be operative to detect a property of the analyte comprising subjecting the Msp porin to an electric field such that the analyte electrophoretically translocates through the tunnel of the Msp porin. Also provided is a system comprising an Msp porin having a vestibule and a constriction zone that define a tunnel, wherein the tunnel is positioned in a lipid bilayer between a first liquid medium and a second liquid medium, and wherein the only point of liquid communication between the first and second liquid media occurs in the tunnel. Moreover, any Msp porin described herein may be comprised in any system described herein.

The first and second liquid media may be the same or different, and either one or both may comprise one or more of a salt, a detergent, or a buffer. Indeed, any liquid media described herein may comprise one or more of a salt, a detergent, or a buffer. Optionally, at least one liquid medium is conductive. Optionally, at least one liquid medium is not conductive. Any liquid medium described herein may comprise a viscosity-altering substance or a velocity-altering substance. The liquid media may comprise any analyte described herein. A property of an analyte may be an electrical, chemical, or physical property.

An Msp porin may be comprised in a lipid bilayer in a system or any other embodiment described herein. A system may comprise a plurality of Msp porins.

A system may comprise any Msp porin described herein, such as a wild-type MspA porin, a mutant MspA porin, a wild-type MspA paralog or homolog porin, or a mutant MspA paralog or homolog porin. Optionally, the Msp porin is further defined as a mutant MspA porin. A system may comprise a mutant Msp porin comprising a vestibule and a constriction zone that define a tunnel, and at least a first mutant MspA monomer comprising a mutation at position 93 and a mutation at position 90, position 91, or both positions 90 and 91. A mutant Msp porin comprised in a system may comprise a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. A mutant MspA porin may further comprise at least a first mutant MspA paralog or homolog monomer. An Msp porin comprised in a system may be encoded by a nucleic acid sequence encoding a single-chain Msp porin.

An Msp porin comprised in a system may further comprise a molecular motor. The molecular motor in a system or any other embodiment herein may be capable of moving an analyte into or through a tunnel with a translocation velocity or an average translocation velocity that is less than the translocation velocity or average translocation velocity at which the analyte translocates into or through the tunnel in the absence of the molecular motor.

Any system described herein may further comprise a patch-clamp amplifier or a data acquisition device. A system may further comprise one or more temperature regulating devices in communication with the first liquid medium, the second liquid medium, or both.

Any system described herein may be operative to translocate an analyte through an Msp porin tunnel either electrophoretically or otherwise.

Also provided is an Msp porin comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. Also provided is a mutant Msp porin comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. Also provided is a mutant MspA porin comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. Also provided is a mutant MspA paralog or homolog porin comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. Any mutant MspA paralog or homolog described herein may further comprise at least a first mutant MspA paralog or homolog monomer. Also provided is a mutant MspA porin comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel, and further comprising at least a first mutant MspA paralog or homolog monomer. Any of these porins may be employed in any embodiment herein.

Also provided is a mutant MspA porin comprising a vestibule and a constriction zone that define a tunnel, and at least a first mutant MspA monomer comprising a mutation at position 93 and a mutation at position 90, position 91, or both positions 90 and 91. This mutant MspA porin, and any other mutant Msp porin or MspA porin described herein, may be employed with any embodiment described herein. The mutant MspA porin may comprise a mutation at positions 93 and 90. The mutant MspA porin may comprise a mutation at positions 93 and 91. The mutant MspA porin may comprise a mutation at positions 93, 91, and 90. The mutant MspA porin may comprise any other mutation described herein.

The diameter of the constriction zone of the mutant MspA porin may be less than the diameter of the constriction zone of a corresponding wild-type MspA porin. The MspA porin may have a mutation in the vestibule or the constriction zone that permits an analyte to translocate, electrophoretically or otherwise, through the tunnel of the mutant with a translocation velocity or an average translocation velocity that is less than the translocation velocity or average translocation velocity at which the analyte translocates through the tunnel of a wild-type Msp porin. The MspA porin may have a mutation in the vestibule or the constriction zone that permits an analyte to translocate, e.g., electrophoretically, through the tunnel with an average translocation velocity of less than 0.5 nm/µs or less than 0.05 nm/µs. The analyte may be selected from the group consisting of a nucleotide, a nucleic acid, an amino acid, a peptide, a protein, a polymer, a drug, an ion, a biological warfare agent, a pollutant, a nanoscopic object, or a combination or cluster thereof. Optionally, the analyte is further defined as a nucleic acid. The nucleic acid may translocate, electrophoretically or otherwise, through the tunnel with an average translocation velocity of less than 1 nucleotide/µs, or less than 0.1 nucleotide/µs. A nucleic acid may be further defined as ssDNA, dsDNA, RNA, or a combination thereof.

An analyte in any embodiment herein may further comprise a magnetic bead. A magnetic bead may be further defined as a streptavidin-coated magnetic bead. An analyte may further comprise an optical bead. Any analyte described herein may be an ion or may be neutral. An analyte may comprise biotin.

Any Msp porin described herein, such as a mutant MspA porin, may comprise 2-15 Msp monomers that are the same or different. Optionally, an Msp porin, such as a mutant MspA porin, comprises 7-9 Msp monomers that are the same or different. Optionally, at least a second monomer is selected from the group consisting of a wild-type MspA monomer, a second mutant MspA monomer, a wild-type MspA paralog or homolog monomer, and a mutant MspA paralog or homolog monomer, wherein the second mutant MspA monomer may be the same or different than the first mutant MspA monomer. Optionally, the second monomer is a wild-type MspA paralog or homolog monomer. A wild-type MspA paralog or homolog monomer may be a wild-type MspB monomer. A MspA monomer may comprise one or more mutations at any of the following amino acid positions: 88, 105, 108, 118, 134, or 139. A MspA monomer may comprise one or more of the following mutations: L88W, D90K/N/Q/R, D91N/Q, D93N, I105W, N108W, D118R, D134R, or E139K. A MspA monomer may comprise the following mutations: D90N/D91N/D93N. A MspA monomer may comprise the following mutations: D90N/D91N/D93N/D118R/D134R/E139K. A MspA monomer may comprise the following mutations: D90Q/D91Q/D93N. A MspA monomer may comprise the following mutations: D90Q/D91Q/D93N/D118R/D134R/E139K. A MspA monomer may comprise the following mutations: D90(K,R)/D91N/D93N. A MspA monomer may comprise the following mutations: (L88, I105)W/D91Q/D93N. A MspA monomer may comprise the following mutations: I105W/N108W. Moreover, an MspA monomer may comprise any other mutation described herein.

In any embodiment herein, a mutant Msp porin, such as a mutant MspA porin or a mutant MspA paralog or homolog, may comprise at least one additional positively charged amino acid compared to the vestibule or the constriction zone of a wild-type Msp porin, respectively; at least one additional negatively charged amino acid compared to the vestibule or the constriction zone of a wild-type MspA porin, respectively; at least one less positively charged amino acid compared to the vestibule or the constriction zone of a wild-type MspA porin, respectively; or at least one less negatively charged amino acid compared to the vestibule or the constriction zone of a wild-type MspA porin, respectively.

Optionally, each positively charged amino acid in the vestibule and the constriction zone of a wild-type Msp porin is replaced with a negatively charged amino acid, and each negatively charged amino acid is the same or different; or each negatively charged amino acid in the vestibule and the constriction zone of a wild-type Msp porin is replaced with a positively charged amino acid, and each positively charged amino acid is the same or different.

Optionally, the vestibule or the constriction zone of a mutant Msp porin comprises a greater number of positively charged residues than that of the vestibule or the constriction zone of a wild-type Msp porin, respectively; or the vestibule or the constriction zone comprises a greater number of negatively charged residues than that of the vestibule or the constriction zone of a wild-type Msp porin, respectively; or at least one positively charged amino acid in the vestibule or the constriction zone of a wild-type Msp porin, such as wild-type MspA porin or a wild-type MspA paralog or homolog porin, is either deleted or replaced by a negatively charged amino acid; or at least one negatively charged amino acid in the vestibule or the constriction zone of a wild-type Msp porin is either deleted or replaced by a positively charged amino acid.

At least one amino acid in the vestibule or the constriction zone of a wild-type Msp porin, such as a wild-type MspA porin or a wild-type MspA paralog or homolog porin, may be substituted by an amino acid having a sterically larger side chain; an amino acid having a sterically smaller side chain; an amino acid having a more polar side chain; an amino acid having a less polar side chain; or an amino acid having a more hydrophobic side chain; an amino acid having a less hydrophobic side chain.

In any embodiment herein, at least one amino acid in the vestibule or the constriction zone of a mutant Msp porin may comprise an unnatural amino acid or a chemically modified amino acid.

Any Msp porin described herein may comprise one or more periplasmic loop deletions, additions, or substitutions.

As described herein, any Msp porin, such as a mutant MspA porin, may further comprise a molecular motor. Any molecular motor described herein may be capable of moving an analyte into or through the tunnel with a translocation velocity or an average translocation velocity that is less than the translocation velocity or average translocation velocity at which the analyte translocates into or through the tunnel in the absence of the molecular motor. In any embodiment herein, the molecular motor may be an enzyme, such as a polymerase, an exonuclease, or a Klenow fragment.

Also provided are methods of making the Msp porins described herein. Accordingly, provided is a method of making a mutant MspA porin comprising at least one mutant MspA monomer, the method comprising modifying a wild-type MspA monomer at position 93 and at position 90, position 91, or both positions 90 and 91. The method may comprise modifying a wild-type MspA monomer at positions 93 and 90. The method may comprise modifying a wild-type MspA monomer at positions 93 and 91. The method may comprise modifying a wild-type MspA monomer at positions 93, 91, and 90. The method may further or alternatively comprise modifying a wild-type MspA monomer at any one or more of the following amino acid positions: 88, 105, 108, 118, 134, or 139, or performing any other modification described herein. A mutant MspA porin made by methods described herein may comprise any mutation or porin property described herein. For example, a mutant MspA may comprise a neutral constriction zone. A mutant MspA porin may further comprises at least one Msp monomer, such as a wild-type MspA monomer, a mutant MspA monomer, a wild-type MspA paralog or homolog, or a second mutant MspA paralog or homolog monomer. The mutant MspA porin may have a conductance through the tunnel that is higher, such as two-fold higher, than the conductance through the tunnel of its corresponding wild-type MspA porin.

Any mutant Msp porin described herein, such as a mutant MspA porin or a mutant MspA paralog or homolog porin, may comprise one or more mutant MspB, mutant MspC, or mutant MspD monomers, or combination thereof.

Also provided is a method of making a mutant MspA porin having a vestibule and a constriction zone that define a tunnel, comprising deleting, adding, or replacing any amino acid in the vestibule or the constriction zone of a wild-type MspA paralog or homolog monomer such that the resulting mutant MspA porin is capable of translocating an analyte through the tunnel upon application of an electric field. The mutant MspA porin may be of any type described herein.

Also provided are nucleic acid sequences encoding the Msp porins described herein. For example, provided is a nucleic acid sequence encoding a mutant MspA porin or a mutant MspA paralog or homolog. Vectors comprising nucleic acid sequences described herein are also contemplated, such as a vector comprising a nucleic acid sequence encoding a mutant MspA porin or a mutant MspA paralog or homolog. Any vector described herein may further comprise a promoter sequence. Any vector described herein may further comprise a constitutive promoter. A constitutive promoter may comprise a $p_{smyc}$ promoter. A promoter may comprise an inducible promoter. An inducible promoter may comprise an acetamide-inducible promoter.

Also provided are cultured cells transfected with any vector described herein, or progeny thereof wherein the cell is capable of expressing an Msp porin, such as a mutant MspA porin or mutant MspA paralog or homolog.

Also provided is a *Mycobacterium smegmatis* strain comprising any vector described herein. A *Mycobacterium smegmatis* strain free of endogenous porins is also contemplated, and may further comprise any vector described herein. By "free" it is meant that an endogenous porin cannot be detected in an immunoblot when using an appropriate Msp-specific antiserum, or comprising less than 1% endogenous porins.

A vector comprising a nucleic acid sequence encoding a wild-type Msp monomer, wherein the nucleic acid sequence is operably controlled by an inducible promoter, is also provided. The vector may be an integration vector. Also provided is a cultured cell transfected with this vector, or progeny thereof, wherein the cell is capable of expressing a wild-type Msp porin. A *Mycobacterium smegmatis* strain comprising this vector is also contemplated.

Also provided are nucleic acid sequences encoding a partial or complete single-chain Msp porin described herein. The nucleic acid sequence may comprise, for example: (a) a first and second nucleotide sequence, wherein the first nucleotide sequence encodes a first Msp monomer sequence and the second nucleotide sequence encodes a second Msp monomer sequence; and (b) a third nucleotide sequence encoding an amino acid linker sequence. The first and second Msp monomer sequences may be independently selected from the group consisting of a wild-type MspA monomer, a mutant MspA monomer, a wild-type MspA paralog or homolog monomer, and a mutant MspA paralog or homolog monomer. The first Msp monomer sequence may comprise a wild-type MspA monomer or a mutant thereof. Optionally, the first Msp monomer sequence comprises a mutant MspA monomer. The first Msp monomer sequence may comprise one or more of the mutations selected from the group consisting of an A to P substitution at amino acid 138, an E to A or K substitution at amino acid 139, a D to K or R or Q substitution at amino acid 90; a D to N or Q substitution at amino acid 91, a D to N substitution at amino acid 93, an L to W substitution at amino acid 88, an I to W substitution at amino acid 105, a N to W substitution at amino acid 108, a D to R substitution at amino acid 118, and a D to R substitution at amino acid 134. Indeed, any Msp monomer described herein may comprise any of these substitutions.

Optionally, the mutant MspA monomer comprises an A to P substitution at amino acid 138, an E to A substitution at amino acid 139, or a combination thereof; a D to K or R substitution at amino acid 90, a D to N substitution at amino acid 91, a D to N substitution at amino acid 93, or any combination thereof a D to Q substitution at amino acid 90, a D to Q substitution at amino acid 91, a D to N substitution at amino acid 93, or any combination thereof a L to W substitution at amino acid 88, an I to W substitution at amino acid 105, a D to Q substitution at amino acid 91, a D to N substitution at amino acid 93, or any combination thereof an I to W substitution at amino acid 105, a N to W substitution at amino acid 108, or a combination thereof; or a D to R substitution at amino acid 118, an E to K substitution at amino acid 139, a D to R substitution at amino acid 134, or any combination thereof.

Any Msp porin may comprise a first, second, or more Msp monomer sequence comprising a wild-type MspA paralog or mutant thereof, wherein the paralog or mutant thereof is a wild-type MspB monomer or a mutant thereof. One or more Msp monomer sequences may comprise SEQ ID NO:1, SEQ ID NO:2, or a combination thereof. Optionally, the second Msp monomer sequence comprises a mutant MspB monomer. Optionally, the first Msp monomer sequence comprises a wild-type MspA monomer or a mutant thereof and the second Msp monomer sequence comprises a wild-type MspB monomer or a mutant thereof. Optionally, the first Msp monomer sequence comprises SEQ ID NO:1 and the second Msp monomer sequence comprises SEQ ID NO:2.

Amino acid linker sequences are described herein. In any embodiment herein, an amino acid linker sequence may, for example, comprise 10 to 20 amino acids. For example, an amino acid linker sequence comprises 15 amino acids. Optionally, the amino acid linker sequence comprises a (GGGGS)$_3$ (SEQ ID NO:3) peptide sequence.

Polypeptides encoded by any nucleic acid sequence described herein are contemplated.

Also provided is a nucleic acid sequence encoding a partial or complete single-chain Msp porin, wherein the nucleic acid sequence comprises (a) a first, second, third, fourth, fifth, sixth, seventh, and eighth nucleotide sequence or any subset thereof, wherein the first, second, third, fourth, fifth, sixth, seventh, and eighth nucleotide sequences encode a first, second, third, fourth, fifth, sixth, seventh, and eighth Msp monomer sequence, respectively; and (b) a ninth nucleotide sequence encoding an amino acid linker sequence. The first and second Msp monomer sequences may be independently selected from the group consisting of a wild-type Msp monomer, a mutant Msp monomer, a wild-type MspA paralog or homolog monomer, and a mutant MspA paralog or homolog monomer. Each Msp monomer may comprise a wild-type MspA monomer or a mutant thereof. Optionally, at least one Msp monomer comprises a wild-type MspA monomer or a mutant thereof. Optionally, at least one Msp monomer comprises a mutant MspA monomer. The mutant Msp monomer sequence may comprise any mutation described herein. For example, one or more of the mutations may be selected from the group consisting of an A to P substitution at amino acid 138, an E to A or K substitution at amino acid 139, a D to K or R or Q substitution at amino acid 90; a D to N or Q substitution at amino acid 91, a D to N substitution at amino acid 93, an L to W substitution at amino acid 88, an I to W substitution at amino acid 105, a N to W substitution at amino acid 108, a D to R substitution at amino acid 118, and a D to R substitution at amino acid 134. Each Msp monomer sequence may comprise SEQ ID NO:1. Optionally, at least one Msp monomer sequence comprises SEQ ID NO:1. Optionally, at least one Msp monomer sequence comprises a wild-type MspA paralog or mutant thereof, wherein the MspA paralog or mutant thereof is a wild-type MspB monomer or a mutant thereof. Optionally, at least one Msp monomer sequence comprises SEQ ID NO:2. Optionally, at least one Msp monomer sequence comprises a mutant MspB monomer. Optionally, at least one Msp monomer sequence comprises a wild-type MspA monomer or a mutant thereof and at least one Msp monomer sequence comprises a wild-type MspB monomer or a mutant thereof. Optionally, at least one Msp monomer sequence comprises SEQ ID NO:1 and at least one Msp monomer sequence comprises SEQ ID NO:2. A polypeptide encoded by any of the foregoing nucleic acid sequences is also provided. A vector comprising any of the foregoing nucleic acid sequences is also provided. The vector may further comprise a promoter sequence. The promoter may comprise a constitutive promoter. The constitutive promoter may comprise a p$_{smyc}$ promoter. The promoter may comprise an inducible promoter. The inducible promoter may comprise an acetamide-inducible promoter.

Also provided is a mutant bacterial strain capable of inducible Msp expression, the bacterial strain comprising (a) a deletion of a wild-type MspA; (b) a deletion of a wild-type MspC; (c) a deletion of a wild-type MspD; and (d) a vector comprising an inducible promoter operably linked to an Msp monomer nucleic acid sequence. The bacterial strain may further comprise *M. smegmatis* strain ML16. The Msp nucleic acid may encode a wild-type MspA monomer or a wild-type MspA paralog or homolog monomer. The Msp nucleic acid may encode an Msp monomer selected from a group consisting of a wild-type MspA monomer, a wild-type MspC monomer, and a wild-type MspD monomer. Optionally, the Msp nucleic acid encodes the wild-type MspA monomer. The inducible promoter may comprise an acetamide inducible promoter. The bacterial strain may further comprise a deletion of a wild-type MspB. The bacterial strain may further comprise a vector as described herein, such as a vector comprising a constitutive promoter operably linked to a nucleic acid sequence that encodes an Msp porin or monomer. The Msp may be a wild-type MspA porin or monomer or a wild-type MspA paralog or homolog porin or monomer. The Msp porin or monomer may be selected from the group consisting of a wild-type MspA porin or monomer, a wild-type MspB porin or monomer, a wild-type MspC porin or monomer, and a wild-type MspD porin or monomer. Optionally, the Msp porin or monomer is a wild-type MspA porin or monomer.

The bacterial strain may further comprise a vector comprising a nucleic acid encoding a full or partial single-chain Msp porin, wherein the nucleic acid comprises (a) a first and second nucleotide sequence, wherein the first nucleotide sequence encodes a first Msp monomer and the second nucleotide sequence encodes a second Msp monomer sequence; and (b) a third nucleotide sequence encoding an amino acid linker sequence. The bacterial strain may further comprise a vector comprising a nucleic acid encoding a full or partial single-chain Msp porin, wherein the nucleic acid comprises (a) a first, second, third, fourth, fifth, sixth, seventh, and eighth nucleotide sequence or any subset thereof, wherein the first, second third, fourth, fifth, sixth, seventh, and eighth nucleotide sequences encode a first, second, third, fourth, fifth, sixth, seventh, and eighth Msp monomer sequence, respectively; and (b) a ninth nucleotide sequence encoding an amino acid linker sequence.

Also provided is a method of producing a full or partial single-chain Msp porin, the method comprising (a) transforming a bacterial strain as described herein with a vector comprising a nucleic acid sequence capable of encoding a full or partial single-chain Msp porin; and (b) purifying the full or partial single-chain Msp porin from the bacteria. The vector may comprise a nucleic acid sequence encoding a full or partial single-chain Msp porin, wherein the nucleic acid sequence comprises (a) a first and second nucleotide sequence, wherein the first nucleotide sequence encodes a first Msp monomer sequence and the second nucleotide sequence encodes a second Msp monomer sequence; and (b) a third nucleotide sequence encoding an amino acid linker sequence. The vector may comprise a nucleic acid sequence encoding a full or partial single-chain Msp porin, wherein the nucleic acid sequence comprises (a) a first, second, third, fourth, fifth, sixth, seventh, and eighth nucleotide sequence or any subset thereof, wherein the first, second, third, fourth, fifth, sixth, seventh, and eighth nucleotide sequences encode a first, second, third, fourth, fifth, sixth, seventh, and eighth Msp monomer sequence, respectively; and (b) a ninth nucleotide sequence encoding an amino acid linker. The Msp monomer sequences may be independently selected from the group consisting of a wild-type MspA monomer, a mutant MspA monomer, a wild-type MspA paralog or homolog monomer, and a mutant MspA paralog or homolog monomer. For example, the Msp monomer sequences are wild-type MspA monomers.

A "*Mycobacterium smegmatis* porin (Msp)" or "Msp porin" refers to a multimer complex comprised of two or more Msp monomers. An Msp monomer is encoded by a gene in *Mycobacterium smegmatis*. *Mycobacterium smegmatis* has four identified Msp genes, denoted MspA, MspB, MspC, and MspD. An Msp porin can, for example, be comprised of wild-type MspA monomers, mutant MspA monomers, wild-type MspA paralog or homolog monomers, or mutant MspA paralog or homolog monomers. Optionally, an Msp porin is a single-chain Msp porin or is a multimer of several single-chain Msp porins. A single-chain Msp porin can, for example comprise a multimer formed by two or more Msp monomers (e.g., eight monomers) connected by one or more amino acid linker peptides. A partial single chain Msp porin refers to a single chain multimer complex that must dimerize, trimerize, or the like to form a porin. A full single chain Msp porin refers to a single chain multimer complex that forms a porin without the need to dimerize, trimerize or the like to form a porin.

The Msp porin of any embodiment herein may be any Msp porin described herein, such as a wild-type MspA porin, a mutant MspA porin, a wild-type MspA paralog or homolog porin, or a mutant MspA paralog or homolog porin. The Msp porin may be encoded by a nucleic acid sequence encoding a single-chain Msp porin. Any Msp porin here may comprise any Msp monomer described herein, such as a mutant Msp monomer.

Nutrients pass through wild-type porins in mycobacteria. Wild-type MspA porins, wild-type MspB porins, wild-type MspC porins, and wild-type MspD porins are examples of wild-type tunnel-forming porins. An Msp porin may be further defined as any Msp porin described herein, including paralogs, homologs, mutants and single-chain porins.

A "mutant MspA porin" is a multimer complex that has at least or at most 70, 75, 80, 85, 90, 95, 98, or 99 percent or more identity, or any range derivable therein, but less than 100%, to its corresponding wild-type MspA porin and retains tunnel-forming capability. A mutant MspA porin may be recombinant protein. Optionally, a mutant MspA porin is one having a mutation in the constriction zone or the vestibule of a wild-type MspA porin. Optionally, a mutation may occur in the rim or the outside of the periplasmic loops of a wild-type MspA porin. A mutant MspA porin may be employed in any embodiment described herein.

Exemplary wild-type MspA paralogs and homologs are provided in Table 1. Provided are wild-type MspA paralogs, which include wild-type MspB, wild-type MspC, and wild-type MspD. A "paralog," as defined herein, is a gene from the same bacterial species that has similar structure and function. A "homolog," as defined herein, is a gene from another bacterial species that has a similar structure and evolutionary origin. By way of an example, provided are wild-type MspA homologs, which include MppA, PorM1, PorM2, PorM1, and Mmcs4296.

A "mutant MspA paralog or homolog porin" is a multimer complex that has at least or at most 70, 75, 80, 85, 90, 95, 98, or 99 percent or more identity, or any range derivable therein, but less than 100%, to its corresponding wild-type MspA paralog or homolog porin and retains tunnel-forming capability. A mutant MspA paralog or homolog porin may be recombinant protein. Optionally, a mutant MspA paralog or homolog porin is one having a mutation in the constriction zone or the vestibule of the wild-type MspA paralog or homolog porin. Optionally, a mutation may occur in the rim or the outside of the periplasmic loops of a wild-type MspA paralog or homolog porin. Any mutant MspA paralog or homolog porin may be employed in any embodiment described herein, and may comprise any mutation described herein.

An Msp porin may comprise two or more Msp monomers. An "Msp monomer" is a protein monomer that is either a wild-type MspA monomer, a mutant MspA monomer, a wild-type MspA paralog or homolog monomer, or a mutant MspA paralog or homolog monomer, and retains tunnel-forming capability when associated with one or more other Msp monomers. Any Msp porin described herein may comprise one or more of any Msp monomer as described herein. Any Msp porin may comprise, for example, 2-15 Msp monomers, wherein each monomer may be the same or different.

A "mutant MspA monomer" refers to an Msp monomer that has at least or at most 70, 75, 80, 85, 90, 95, 98, or 99 percent or more identity, or any range derivable therein, but less than 100%, to a wild-type MspA monomer, and retains tunnel-forming capability when associated with one or more other Msp monomers. Optionally, a mutant MspA monomer is further defined as comprising a mutation in that portion of the sequence that contributes to the formation of the vestibule or the constriction zone of a fully-formed, tunnel-forming porin. The mutant Msp monomer may be a recombinant protein, for example. A mutant MspA monomer may comprise any mutation described herein.

A "mutant MspA paralog or homolog monomer" refers to an MspA paralog or homolog monomer that has at least or at most 70, 75, 80, 85, 90, 95, 98, or 99 percent or more identity, or any range derivable therein, but less than 100%, to a wild-type MspA paralog or homolog monomer, and retains tunnel-forming capability. Optionally, a mutant MspA paralog or homolog monomer is further defined as comprising a mutation in that portion of the sequence that contributes to the formation of the vestibule and/or the constriction zone of a fully-formed, tunnel-forming porin. The mutant MspA paralog or homolog monomer may be a recombinant protein, for example. Any mutant MspA paralog or homolog monomer may be optionally employed in any embodiment herein.

An Msp porin may be expressed as a combination of two or more wild-type MspA monomers, mutant MspA monomers, wild-type MspA paralog or homolog monomers, or mutant MspA paralog or homolog monomers. As such, an Msp porin may be or comprise a dimer, a trimer, a tetramer, a pentamer, a hexamer, a septamer, an octamer, a nonamer, etc. For example, an Msp porin may comprise a combination of wild-type MspA monomers and wild-type MspB monomers. An Msp porin may comprise 1-15 monomers, where each monomer is the same or different. Indeed, any Msp porin described herein may comprise at least or at most 1, 2, 3, 4, 5, 6, 7, 8, 9, 10, 11, 12, 13, 14, or 15 monomers, or any range derivable therein, where each monomer is the same or different. For example, an Msp porin may comprise one or more mutant MspA monomers that are the same or different. As another example, an Msp porin may comprise at least one mutant MspA monomer and at least one MspA paralog or homolog monomer.

As defined above, a single-chain Msp porin comprises two or more Msp monomers connected by one or more amino acid linker peptides. A single-chain Msp porin that comprises two Msp monomers, wherein the Msp monomers are linked by an amino acid linker sequence, may be referred to as a single-chain Msp porin dimer. A single-chain Msp porin that comprises eight Msp monomers, wherein the Msp monomers are linked by an amino acid linker sequence, may be referred to as a single-chain Msp porin octamer. A single-chain Msp porin may comprise 2, 3, 4, 5, 6, 7, 8, 9, 10, 11, 12, 13, 14, 15, or more Msp monomers, or any range derivable therein, linked by amino acid linker sequences. Optionally, a single-chain Msp porin can, for example, comprise two or more single-chain Msp porin dimers, two or more single-chain Msp porin trimers, two or more single-chain Msp porin quadrimers, two or more single-chain Msp porin pentimers, one or more single-chain Msp porin heximers, one or more single-chain Msp porin septimers, one or more single-chain Msp porin octamers, or combinations thereof. For example, a single-chain Msp porin can comprise a single-chain Msp porin dimer and two single-chain Msp porin trimers. By way of another example, a single-chain Msp porin can comprise a single-chain Msp porin quadrimer and two single-chain Msp porin dimers.

A wild-type single-chain Msp porin is comprised of wild-type Msp monomers. Optionally, one or more mutations in a single-chain Msp porin is present in the vestibule or the constriction zone of the single-chain Msp porin. The mutant single-chain Msp porin, for example, has at least one mutation in the amino acid sequence for the periplasmic loop, vestibule, or constriction zone (e.g., deletion, substitution, or addition) compared with a wild-type single-chain Msp. A multimer of single chains can also form a porin, wherein each single chain includes two, three, four, five, six, seven, or more Msp monomers.

Provided herein are nucleic acid sequences encoding Msp monomer sequences and mutants thereof. For the mutant MspA monomer sequences listed below, the reference MspA sequence is the mature wild-type MspA monomer sequence (SEQ ID NO:1). Each nucleotide sequence in the nucleic acid sequences provided herein can, for example, comprise a mutant MspA monomer sequence. Non-limiting examples of mutant MspA sequences are provided in Table 7. Optionally, the mutant MspA comprises an A to P substitution at amino acid 138, an E to A substitution at amino acid 139, or a combination thereof. Optionally, the mutant MspA comprises a D to K or R substitution at amino acid 90, a D to N substitution at amino acid 91, a D to N substitution at amino acid 93, or any combination thereof. Optionally, the mutant MspA comprises a D to Q substitution at amino acid 90, a D to Q substitution at amino acid 91, a D to N substitution at amino acid 93, or any combination thereof. Optionally, the mutant MspA comprises a L to W substitution at amino acid 88, an I to W substitution at amino acid 105, a D to Q substitution at amino acid 91, a D to N substitution at amino acid 93, or any combination thereof. Optionally, the mutant MspA comprises an I to W substitution at amino acid 105, a N to W substitution at amino acid 108, or a combination thereof. Optionally, the mutant MspA comprises a D to R substitution at amino acid 118, an E to K substitution at amino acid 139, a D to R substitution at amino acid 134, or any combination thereof. For the mutant MspB monomer sequences listed below, the reference MspB sequence is the mature wild-type MspB monomer sequence (SEQ ID NO:2). Optionally, the mutant MspB comprises a D to K or R substitution at amino acid 90, a D to N substitution at amino acid 91, a D to N substitution at amino acid 93, or any combination thereof.

Sequences of wild-type Msp monomers discussed herein are disclosed in GenBank, located on the world wide web, and these sequences and others are herein incorporated by reference in their entireties as are individual subsequences or fragments contained therein. For example, the nucleotide and amino acid sequences of a wild-type MspA monomer can be found at GenBank Accession Nos. AJ001442 and CAB56052, respectively. The nucleotide and amino acid sequences of a wild-type MspB monomer can be found, for example, at GenBank Accession Nos. NC_008596.1 (from nucleotide 600086 to 600730) and YP_884932.1, respectively. The nucleotide and amino acid sequences of a wild-type MspC monomer can be found, for example, at GenBank Accession Nos. AJ299735 and CAC82509, respectively. The nucleotide and amino acid sequences of a wild-type MspD monomer can be found, for example, at GenBank Accession Nos. AJ300774 and CAC83628, respectively. Thus provided are the nucleotide sequences of MspA, MspB, MspC, and MspD monomers comprising a nucleotide sequence at least about 70, 75, 80, 85, 90, 95, 98, 99 percent or more, or any range derivable therein, identical to the nucleotide sequence of the aforementioned nucleotide GenBank Accession Numbers. Also provided are amino acid sequences of MspA, MspB, MspC, and MspD monomers (FIG. 18) comprising an amino acid sequence at least about 70, 75, 80, 85, 90, 95, 98, 99 percent or more, or any range derivable therein, identical to the sequences of the aforementioned amino acid GenBank Accession Numbers.

Also provided are amino acid sequences of MspA paralogs and homolog monomers comprising an amino acid sequence at least about 70, 75, 80, 85, 90, 95, 98, 99 percent or more, or any range derivable therein to a wild-type MspA paralog or homolog monomer. Wild-type MspA paralog and homolog monomers are well-known in the art. Table 1 provides a non-limiting list of such paralogs and homologs:

TABLE 1

Wild-type MspA and Wild-type MspA paralogs and homolog monomers

| Protein# | Organism | Identity/Similarity to MspA (%) | Length (aa) | Reference |
|---|---|---|---|---|
| MspA/Msmeg0965 | *M. smegmatis* | 100/100 | 211 | gb\|ABK74363.1\|, (Stahl et al., 2001)* |
| MspB/Msmeg0520 | *M. smegmatis* | 94/95 | 215 | gb\|ABK73437.1\|, (Stahl et al., 2001)* |
| MspC/Msmeg5483 | *M. smegmatis* | 93/95 | 215 | gb\|ABK74976.1\|, (Stahl et al., 2001)* |
| MspD/Msmeg6057 | *M. smegmatis* | 82/89 | 207 | gb\|ABK72453.1\|, (Stahl et al., 2001)* |

TABLE 1-continued

Wild-type MspA and Wild-type MspA paralogs and homolog monomers

| Protein# | Organism | Identity/Similarity to MspA (%) | Length (aa) | Reference |
|---|---|---|---|---|
| MppA | *M. phlei* | 100/100 | 211 | AJ812030, (Dorner et al., 2004)** |
| PorM1 | *M. fortuitum* | 95/96 | 211 | emb\|CAI54228.1\| |
| PorM2 | *M. fortuitum* | 91/93 | 215 | emb\|CAL29811.1\| |
| PorM1 | *M. peregrinum* | 94/96 | 211 | emb\|CAI54230.1\| |
| Mmcs4296 | *Mycobacterium* sp. MCS | 85/91 | 216 | gb\|ABG10401.1\| |
| Mmcs4297 | *Mycobacterium* sp. MCS | 85/91 | 216 | gb\|ABG10402.1\| |
| Mmcs3857 | *Mycobacterium* sp. MCS | 30/44 | 235 | gb\|ABG09962.1\| |
| Mmcs4382 | *Mycobacterium* sp. MCS | 85/91 | 216 | gb\|ABL93573.1\| |
| Mmcs4383 | *Mycobacterium* sp. MCS | 85/91 | 216 | gb\|ABL93574.1\| |
| Mjls3843 | *Mycobacterium* sp. JLS | 26/40 | 235 | gb\|ABN99619.1\| |
| Mjls3857 | *Mycobacterium* sp. JLS | 26/40 | 235 | gb\|ABG09962.1\| |
| Mjls3931 | *Mycobacterium* sp. JLS | 26/40 | 235 | gb\|ABL93123.1\| |
| Mjls4674 | *Mycobacterium* sp. JLS | 85/89 | 216 | gb\|ABO00440.1\| |
| Mjls4675 | *Mycobacterium* sp. JLS | 83/89 | 216 | gb\|ABO00441.1\| |
| Mjls4677 | *Mycobacterium* sp. JLS | 84/89 | 216 | gb\|ABO00443.1\| |
| Map3123c | *M. avium paratuberculosis* | 24/39 | 220 | gb\|AAS05671.1\| |
| Mav3943 | *M. avium* | 24/39 | 227 | gb\|ABK66660.1\| |
| Mvan1836 | *M. vanbaalenii* PYR-1 | 82/88 | 209 | gb\|ABM12657.1\| |
| Mvan4117 | *M. vanbaalenii* PYR-1 | 32/43 | 239 | gb\|ABM14894.1\| |
| Mvan4839 | *M. vanbaalenii* PYR-1 | 83/88 | 209 | gb\|ABM15612.1\| |
| Mvan4840 | *M. vanbaalenii* PYR-1 | 83/89 | 209 | gb\|ABM15613.1\| |
| Mvan5016 | *M. vanbaalenii* PYR-1 | 30/41 | 238 | gb\|ABM15788.1\| |
| Mvan5017 | *M. vanbaalenii* PYR-1 | 25/35 | 227 | gb\|ABM15789.1\| |
| Mvan5768 | *M. vanbaalenii* PYR-1 | 21/32 | 216 | gb\|ABM16533.1\| |
| MUL_2391 | *M. ulcerans* Agy99 | 21/34 | 233 | gb\|ABL04749.1\| |
| Mflv1734 | *M. gilvum* PYR-GCK | 21/32 | 225 | gb\|ABP44214.1\| |
| Mflv1735 | *M. gilvum* PYR-GCK | 32/41 | 226 | gb\|ABP44215.1\| |
| Mflv2295 | *M. gilvum* PYR-GCK | 25/40 | 250 | gb\|ABP44773.1\| |
| Mflv1891 | *M. gilvum* PYR-GCK | 84/90 | 217 | gb\|ABP44371.1\| |
| MCH4691c | *M. chelonae* | 70/80 | 223 | gb\|ACV04474.1\| |
| MCH4689c | *M. chelonae* | 66/78 | 223 | gb\|ACV04472.1\| |
| MCH4690c | *M. chelonae* | 72/81 | 217 | gb\|ACV04473.1\| |
| MAB1080 | *M. abscessus* | 69/79 | 223 | emb\|CAM61170.1\| |
| MAB1081 | *M. abscessus* | 68/78 | 222 | emb\|CAM61171.1\| |
| MAB2800 | *M. abscessus* | 27/44 | 246 | emb\|CAM62879.1\| |
| RHA1 ro08561 | *Rhodococcus jostii* RHA1 | 34/51 | 233 | gb\|ABG99605.1\| |
| n.d. | *Rhodococcus opacus* B4 | 34/51 | 233 | gbj\|BAH52196.1\| |
| RHA1 ro04074 | *Rhodococcus* sp. RHA1 | 34/50 | 233 | gb\|ABG95871.1\| |
| RHA1 ro03127 | *Rhodococcus* sp. RHA1 | 34/50 | 233 | gb\|ABG94930.1\| |
| n.d. | *Rhodococcus erythropolis* PR4 | 35/50 | 229 | gbj\|BAH30938.1\| |

Only proteins with significant amino acid similarities over the full length of the protein were included. Data were obtained by PSI-Blast algorithm (BLOSUM62 matrix) using the NIH GenBank database on the world wide web.
n.d.: "not determined"
*Stahl et al., *Mol. Microbiol.* 40: 451 (2001)
**Dorner et. al., *Biochim. Biophys. Acta.* 1667: 47-55 (2004)

The peptides, polypeptides, monomers, multimers, proteins, etc. described herein can be further modified and varied so long as the desired function is maintained or enhanced. It is understood that one way to define any known modifications and derivatives or those that might arise, of the disclosed genes and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to a wild-type MspA and wild-type MspA paralogs or homologs (e.g., wild-type MspB, wild-type MspC, wild-type MspD, MppA, PorM1, Mmcs4296), and mutants provided herein.

Those of skill in the art readily understand how to determine the identity of two polypeptides. For example, the identity can be calculated after aligning the two sequences so that the identity is at its highest level. For example, to determine the "percent identity" of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., percent identity=number of identical positions/total number of positions (e.g., overlapping positions)×100). In one embodiment, the two sequences are the same length.

Several methods exist for determining percent identity. One may determine percent identity in the following manner. A target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site. Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options may be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. The following command will generate an output file containing a comparison between two sequences: C:\Bl2seq c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length may be determined by counting the number of matched positions over that length and dividing that number by the length followed by multiplying the resulting value by 100. For example, if (1) a 50 nucleotide target sequence is compared to the sequence encoding wild-type MspA (2) the Bl2seq program presents 45 nucleotides from the target sequence aligned with a region of the sequence encoding wild-type MspA where the first and last nucleotides of that 45 nucleotide region are matches, and (3) the number of matches over those 45 aligned nucleotides is 40, then the 50 nucleotide target sequence contains a length of 45 and a percent identity over that length of 89 (i.e., 40/45×100=89).

Another way of calculating identity can be performed by published algorithms. Optimal alignment of sequences for comparison may be conducted by the local identity algorithm of Smith and Waterman, *Adv. Appl. Math* 2:482 (1981), by the identity alignment algorithm of Needleman and Wunsch, *J. Mol. Biol.* 48:443 (1970), by the search for similarity method of Pearson and Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, *Science* 244:48-52 (1989); Jaeger et al., *Proc. Natl. Acad. Sci. USA* 86:7706-10 (1989); Jaeger et al., *Methods Enzymol.* 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Nucleic acids that encode protein sequences disclosed herein, as well as variants and fragments thereof, are also disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

Fragments and partial sequences of an Msp porin or monomer may be useful in methods described herein. As with all peptides, polypeptides, and proteins, including fragments thereof, it is understood that additional modifications in the amino acid sequence of the Msp polypeptides disclosed herein can occur that do not alter the nature or function of the peptides, polypeptides, and proteins. It will be appreciated that the only limitation on these is practical, they must comprise the necessary functional elements (e.g., tunnel-forming capability) for use in the relevant embodiment. Such modifications include conservative amino acids substitutions and are discussed in greater detail below.

Methods of determining whether a protein is a tunnel-forming protein are well-known in the art. One may determine if an Msp forms a tunnel by determining whether the protein inserts into a bilayer, such as described in Example 2 below: if the protein inserts into the bilayer, then the porin is a tunnel-forming protein. Typically, tunnel formation is detected by observing a discrete change in conductivity. See, e.g., FIG. 2, Example 2, and Niederweis et al., *Mol. Microbiol.* 33:933 (1999). Bilayers are described herein.

As suggested above, an Msp porin will typically be able to be inserted in a lipid bilayer or other thin film, which are each well-known in the art. An example of inserting a mutant MspA porin into a lipid bilayer is explained herein; this technique may be applied to other Msp porins as well. In addition, U.S. Pat. No. 6,746,594, incorporated herein by reference, describes a variety of lipid bilayers and thin films, including inorganic materials, that may be employed with respect to the Msp porins discussed herein. Methods, apparatuses, and techniques described in U.S. Pat. No. 6,267,872, incorporated herein by reference in its entirety, are also employable with respect to Msp porins discussed herein.

Moreover, more than one Msp porin may be comprised in a lipid bilayer. For example, 2 3, 4, 5, 10, 20, 200, 2000, or more may be comprised in a lipid bilayer. Optionally, anywhere from 2 to $10^{10}$ Msp porins may be employed in methods described herein. Such a plurality of Msp porins may be in the form of clusters of Msp porins. Clusters may be randomly assembled or may adopt a pattern. As used herein, a "cluster" refers molecules that are grouped together and move as a unit, but are not covalently bound to one another.

Optionally, Msp porins do not gate spontaneously. "To gate" or "gating" refers to the spontaneous change of electrical conductance through the tunnel of the protein that is usually temporary (e.g., lasting for as few as 1-10 milliseconds to up to a second). Long lasting gating events can often be reversed by changing the polarity. Under most circumstances, the probability of gating increases with the application of higher voltages. Gating and the degree of conductance through the tunnel change are highly variable among Msp porins, depending on, for example, the make-up of the vestibule and constriction zone as well as the properties of the liquid medium in which the protein is submerged. Typically, the protein becomes less conductive during gating, and conductance may permanently stop (i.e., the tunnel may permanently shut) as a result, such that the process is irreversible. Optionally, gating refers to the conductance through the tunnel of a protein spontaneously changing to less than 75% of its open state current.

Various conditions such as light and the liquid medium that contacts an Msp porin, including its pH, buffer composition, detergent composition, and temperature, may affect the behavior of an Msp porin, particularly with respect to its conductance through the tunnel as well as the movement of an analyte with respect to the tunnel, either temporarily or permanently.

Of particular relevance is the geometry of the Msp porin tunnels, particularly the MspA porin. The Msp porin geometry may provide improved spatial resolution. Further, wild-type MspA porin is very robust and retains tunnel-forming activity after exposure to any pH and after extraction at extreme temperatures (e.g., up to 100° C. for up to 30 minutes and incubation at up to 80° C. for up to 15 minutes). The polypeptides may be tested for their desired activity using the in vitro assays described herein.

Regarding the MspA porin in particular, optionally, the MspA porin is an octamer that consists of eight 184-amino acid MspA monomers. One or more mutations may take place in one or more of the amino acid MspA monomers of a wild-type MspA porin to yield a mutant MspA porin. In addition, an MspA porin may have fewer or more than eight monomers, any one or more of which may comprise a mutation.

Moreover, wild-type MspA porin comprises a periplasmic loop that consists of thirteen amino acids and is directly adjacent to the constriction zone. See Huff et al., *J. Biol. Chem.* 284:10223 (2009). Wild-type MspB, C, and D porins also contain a periplasmic loop. One or more mutations may occur in the periplasmic loop of a wild-type Msp porin to generate a mutant Msp porin. For example, deletions of up to all thirteen amino acids may occur in the periplasmic loop of wild-type MspA porin. Typically, deletions in the periplasmic loop do not affect the tunnel-forming ability of an Msp porin.

An Msp porin or Msp monomer may also be chemically or biologically modified. For example, one may modify an Msp porin or Msp monomer with chemicals to produce disulfide bridges, as is known by those of skill in the art.

An Msp porin may comprise a nucleotide binding site. As used herein, a "nucleotide binding site" refers to a site in an Msp porin where a nucleotide stays in contact with, or resides at, an amino acid for a period of time that is longer than attributable to diffusion movement, such as greater than one picosecond or one nanosecond. Molecular dynamics calculations may be employed to assess these temporary resting times.

A "vestibule" refers to the cone-shaped portion of the interior of an Msp porin whose diameter generally decreases from one end to the other along a central axis, where the narrowest portion of the vestibule is connected to the constriction zone. A vestibule may also be referred to as a "goblet." See FIG. 1 for an example of the vestibule of a wild-type MspA porin. The vestibule and the constriction zone together define the tunnel of an Msp porin.

When referring to a diameter of the vestibule, it is understood that because the vestibule is cone-like in shape, the diameter changes along the path of a central axis, where the diameter is larger at one end than the opposite end. The diameter may range from about 2 nm to about 6 nm. Optionally, the diameter is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. The length of the central axis may range from about 2 nm to about 6 nm. Optionally, the length is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. When referring to "diameter" herein, one may determine a diameter by measuring center-to-center distances or atomic surface-to-surface distances.

A "constriction zone" refers to the narrowest portion of the tunnel of an Msp porin, in terms of diameter, that is connected to the vestibule. The constriction zone of a wild-type MspA porin is shown in FIG. 1 (labeled "inner constriction"). The length of the constriction zone may range from about 0.3 nm to about 2 nm. Optionally, the length is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. The diameter of the constriction zone may range from about 0.3 nm to about 2 nm. Optionally, the diameter is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein.

A "neutral constriction zone" refers to a constriction zone comprising amino acid side chains that cumulatively exhibit no net electrical charge when immersed in an aqueous solution. The pH of the liquid medium (e.g., a buffered aqueous solution) in contact with the constriction zone may affect whether the constriction zone is characterized as neutral or not.

A "tunnel" refers to the central, empty portion of an Msp that is defined by the vestibule and the constriction zone, through which a gas, liquid, ion, or analyte may pass.

As used herein, "cis" refers to the side of an Msp tunnel through which an analyte enters the tunnel or across the face of which the analyte moves.

As used herein, "trans" refers to the side of an Msp tunnel through which an analyte (or fragments thereof) exits the tunnel or across the face of which the analyte does not move.

As used herein, "electrophoretically translocating an analyte," and grammatical variants thereof, refers to applying an electric field to an Msp porin that is in contact with one or more solutions (e.g., immersed in a solution), such that current flows through the Msp porin tunnel. The electric field moves an analyte such that it interacts with the tunnel. By "interacts," it is meant that the analyte moves into and, optionally, through the tunnel, where "through the Msp tunnel" (or "translocates") means to enter one side of the tunnel and move to and out of the other side of the tunnel.

It is specifically contemplated that any analyte discussed herein may translocate through an Msp porin tunnel, either electrophoretically or otherwise, in any embodiment discussed herein. In this regard, it is specifically contemplated that any embodiment herein comprising translocation may refer to electrophoretic translocation or non-electrophoretic translocation, unless specifically noted. Optionally, methods that do not employ electrophoretic translocation are contemplated.

A "liquid medium" includes aqueous, organic-aqueous, and organic-only liquid media. Organic media include, e.g., methanol, ethanol, dimethylsulfoxide, and mixtures thereof. Liquids employable in methods described herein are well-known in the art. Descriptions and examples of such media, including conductive liquid media, are provided in U.S. Pat. No. 7,189,503, for example, which is incorporated herein by reference in its entirety. Salts, detergents, or buffers may be added to such media. Such agents may be employed to alter pH or ionic strength of the liquid medium. Viscosity-altering substances, such as glycerol or various polymers (e.g., polyvinylpyrrolidone, polyethylene glycol, polyvinyl alcohol, cellulose polymers), and mixtures thereof, may be included in liquid media. Methods of measuring viscosity are well-known in the art. Any agent that may be added to a liquid medium may also alter the velocity of an analyte that is being studied. As such, a velocity-altering agent may be a salt, a detergent, a buffer, a viscosity-altering substance, or any other agent added to a liquid medium that increases or decreases the velocity of an analyte.

Typically, an analyte employed herein is soluble or partially soluble in at least one liquid medium that is in contact with an Msp described herein. Any analyte may be used herein, including, for example, a nucleotide, a nucleic acid, an amino acid, a peptide, a protein, a polymer, a drug, an ion, a biological warfare agent, a pollutant, a nanoscopic object, or any other molecule comprising one of these analytes or a combination of thereof. An analyte may be a cluster of molecules, in that the cluster as a whole is considered an analyte. Typically, an analyte's size will not be so great such that it cannot enter a tunnel of an Msp: in other words, a typical analyte will be smaller in size than the opening of a tunnel of an Msp. However, an analyte having a size larger than the opening of a tunnel may be employed, and it may be determined using methods described herein that the analyte's size is too large to enter the tunnel. Optionally, the molecular weight of the analyte is less than one million Da. Optionally, the molecular weight of the analyte is about, at most about, or at least about 1,000,000, 950,000, 900,000, 850,000, 800,000, 750,000, 700,000, 650,000, 600,000, 550,000, 500,000, 450,000, 400,000, 350,000, 300,000, 250,000, 200,000, 150,000, 100,000, 75,000, 50,000, 25,000, 20,000, 15,000, 10,000, 7,500, 5,000, 2,500, 2,000, 1,500, 1,000, or 500 Da or less, or any range derivable therein.

Protein modifications include amino acid sequence modifications. Modifications in amino acid sequence may arise naturally as allelic variations (e.g., due to genetic polymorphism), may arise due to environmental influence (e.g., due to exposure to ultraviolet radiation), or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations may or may not place the sequence out of reading frame and may or may not create complementary regions that could produce secondary mRNA structure. Substitutional modifications are those in which at least one residue has been removed and a different residues inserted in its place.

Modifications, including the specific amino acid substitutions, are made by known methods. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

One or more mutations in an Msp porin may occur in the vestibule or the constriction zone of the protein. Optionally, a mutant Msp porin has at least one difference in its periplasmic loop, vestibule, or constriction zone amino acid sequence (e.g., deletion, substitution, addition) compared with the wild-type Msp porin.

As used herein, an "amino acid" refers to any of the 20 naturally occurring amino acids found in proteins, D-stereoisomers of the naturally occurring amino acids (e.g., D-threonine), unnatural amino acids, and chemically modified amino acids. Each of these types of amino acids is not mutually exclusive. α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine).

The following abbreviations are used for the 20 naturally occurring amino acids: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unnatural amino acids (that is, those that are not naturally found in proteins) are also known in the art, as set forth in, for example, Williams et al., *Mol. Cell. Biol.* 9:2574 (1989); Evans et al., *J. Amer. Chem. Soc.* 112:4011-4030 (1990); Pu et al., *J. Amer. Chem. Soc.* 56:1280-1283 (1991); Williams et al., *J. Amer. Chem. Soc.* 113:9276-9286 (1991); and all references cited therein. β- and γ-Amino acids are known in the art and are also contemplated herein as unnatural amino acids. The following table shows non-limiting examples of unnatural amino acids that are contemplated herein.

TABLE 2

Exemplary Unnatural Amino Acids

| Abbr. | Amino Acid |
|---|---|
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

As used herein, a "chemically modified amino acid" refers to an amino acid whose side chain has been chemically modified. For example, a side chain may be modified to comprise a signaling moiety, such as a fluorophore or a radiolabel. A side chain may be modified to comprise a new functional group, such as a thiol, carboxylic acid, or amino group. Post-translationally modified amino acids are also included in the definition of chemically modified amino acids.

Amino acids, and, more specifically, their side chains, may be characterized by their chemical characteristic(s). For example, amino acid side chains may be positively charged, negatively charged, or neutral. The pH of a solution affects the charged nature of certain side chains, as is known by those of skill in the art. Non-limiting examples of side chains that may be positively charged include histidine, arginine, and lysine. Non-limiting examples of side chains that may be negatively charged include aspartic acid and glutamic acid. Non-limiting examples of side chains that may be characterized as neutral include glycine, alanine, phenylalanine, valine, leucine, isoleucine, cysteine, asparagine, glutamine, serine, threonine, tyrosine, methionine, proline, and tryptophan.

Sterics of side chains may also be used to characterize an amino acid. Tables of atom diameters may assist one in determining whether one side chain is larger than another. Computer models may also help with this determination.

Amino acids may be characterized by the polarity of their side chains. Polar side chains, which are typically more hydrophilic than non-polar side chains, include, for example, those of serine, threonine, tyrosine, cysteine, asparagine, and glutamine. Non-polar side chains, which are typically more hydrophobic than polar side chains, include, for example, those of glycine, alanine, valine, leucine, isoleucine, proline, methionine, phenylalanine, and tryptophan. One may determine polarity of a side chain using conventional techniques known in the art involving atom electronegativity determinations and three-dimensional structural assessments of side chains. One may also compare hydrophobicities/hydrophilicities of side chains using conventional techniques known in the art, such as comparing the octanol/water partition coefficient of each amino acid. See Sangster, In: Octanol-Water Partition Coefficients: Fundamentals and Physical Chemistry, Wiley Series in Solution Chemistry, Chichester: John Wiley & Sons Ltd., 2:178 pages (1997).

The following table provides non-limiting examples of properties of amino acids that may assist a skilled artisan in determining how to select amino acids for modifications of an Msp porin or monomer as described herein.

TABLE 3

Amino Acid Properties

| Amino Acid | Percent Buried Residues[a] (%) | Average Volume[b] (Å³) | van der Waals volume[c] (Å³) | Accessible surface area[d] (Å²) | Ranking of amino acid polarities[e] |
|---|---|---|---|---|---|
| alanine | 38 (12) | 92 | 67 | 67 | 9 (7) |
| arginine | 0 | 225 | 148 | 196 | 15 (19) |
| asparagine | 10 (2) | 135 | 96 | 113 | 16 (16) |
| aspartic acid | 14.5 (3) | 125 | 91 | 106 | 19 (18) |
| cysteine | 47 (3) | 106 | 86 | 104 | 7 (8) |
| glutamine | 6.3 (2.2) | 161 | 114 | 144 | 17 (14) |
| glutamic acid | 20 (2) | 155 | 109 | 138 | 18 (17) |
| glycine | 37 (10) | 66 | 48 | | 11 (9) |
| histidine | 19 (1.2) | 167 | 118 | 151 | 10 (13) |
| isoleucine | 65 (12) | 169 | 124 | 140 | 1 (2) |
| leucine | 41 (10) | 168 | 124 | 137 | 3 (1) |
| lysine | 4.2 (0.1) | 171 | 135 | 167 | 20 (15) |
| methionine | 50 (2) | 171 | 124 | 160 | 5 (5) |
| phenylalanine | 48 (5) | 203 | 135 | 175 | 2 (4) |
| proline | 24 (3) | 129 | 90 | 105 | 13 (—) |
| serine | 24 (8) | 99 | 73 | 80 | 14 (12) |
| threonine | 25 (5.5) | 122 | 93 | 102 | 12 (11) |
| tryptophan | 23 (1.5) | 240 | 163 | 217 | 6 (6) |
| tyrosine | 13 (2.2) | 203 | 141 | 187 | 8 (10) |
| valine | 56 (15) | 142 | 105 | 117 | 4 (3) |

[a] This column represents the tendency of an amino acid to be buried (defined as <5% of residue available to solvent) in the interior of a protein and is based on the structures of nine proteins (total of ~2000 individual residues studied, with 587 (29%) of these buried). Values indicate how often each amino acid was found buried, relative to the total number of residues of this amino acid found in the proteins. Values in parentheses indicate the number of buried residues of this amino acid found relative to all buried residues in the proteins. Data from Schien, BioTechnology 8:308 (1990); for other calculation methods with similar results, see Janin, Nature 277:491 (1979); and Rose et al., Science 229:834 (1985).

[b] Average volume ($V_r$) of buried residues, calculated from the surface area of the side chain. Richards, Annu. Rev. Biophys. Bioeng. 6:151 (1977); Baumann, Protein Eng. 2:329 (1989).

[c] Data from Darby N. J. and Creighton T. E. Protein structure. In In focus (ed. D. Rickwood), p. 4. IRL Press, Oxford, United Kingdom (1993).

[d] Total accessible surface area (ASA) of amino acid side chain for residue X in a Gly-X-Gly tripeptide with the main chain in an extended conformation. Miller et al., J. Mol. Biol. 196:641 (1987).

$^e$ Values shown represent the mean ranking of amino acids according to the frequency of their occurrence at each sequence rank for 38 published hydrophobicity scales. Trinquier and Sanejouand, *Protein Eng.* 11:153 (1998). Although the majority of these hydrophobicity scales are derived from experimental measurements of chemical behavior or physicochemical properties (e.g., solubility in water, partition between water and organic solvent, chromatographic migration, or effects on surface tension) of isolated amino acids, several "operational" hydrophobicity scales based on the known environment characteristics of amino acids in proteins, such as their solvent accessibility or their inclination to occupy the core of proteins (based on the position of residues in the tertiary structures as observed by x-ray crystallography or NMR) are included. The lower rankings represent the most hydrophobic amino acids, and higher values represent the most hydrophilic amino acids. For comparative purposes, the hydrophobicity scale of Radzicka and Wolfenden, *Biochem.* 27:1664 (1988) is shown in parentheses. That scale was derived from the measured hydration potential of amino acids that is based on their free energies of transfer from the vapor phase to cyclohexane, 1-octanol, and neutral aqueous solution.

Alternatively, one may consider the hydropathic index of amino acids. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5). The importance of the hydropathic amino acid index in conferring interactive biological function on a protein is generally understood in the art. It is known that certain amino acids may be substituted for other amino acids having a similar hydropathic index and/or score and/or still retain a similar biological activity. In making changes based upon the hydropathic index, the substitution of amino acids whose hydropathic indices may be within ±2; within ±1, or within ±0.5.

It also is understood in the art that the substitution of like amino acids can be made effectively on the basis of hydrophilicity. As detailed in U.S. Pat. No. 4,554,101, incorporated herein by reference, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is contemplated that the substitution of amino acids whose hydrophilicity values may be within ±2, within ±1, or those within ±0.5.

Any mutant Msp porin or monomer may comprise a conservative amino acid substitution as compared to a wild-type Msp porin or monomer. Any substitution mutation is conservative in that it minimally disrupts the biochemical properties of the protein. Non-limiting examples of mutations that are introduced to substitute conservative amino acid residues include: positively-charged residues (e.g., H, K, and R) substituted with positively-charged residues; negatively-charged residues (e.g., D and E) substituted with negatively-charged residues; neutral polar residues (e.g., C, G, N, Q, S, T, and Y) substituted with neutral polar residues; and neutral non-polar residues (e.g., A, F, I, L, M, P, V, and W) substituted with neutral non-polar residues. Conservative substitutions may made in accordance with the following Table 4. Nonconservative substitutions can be made as well (e.g., proline for glycine).

TABLE 4

Exemplary Amino Acid Substitutions

| Amino Acid | Substitutions |
| --- | --- |
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

As used herein, a "peptide" refers to two or more amino acids joined together by an amide bond (that is, a "peptide bond"). Peptides comprise up to or include 50 amino acids. Peptides may be linear or cyclic. Peptides may be α, β, γ, δ, or higher, or mixed. Peptides may comprise any mixture of amino acids as defined herein, such as comprising any combination of D, L, α, β, γ, δ, or higher amino acids.

As used herein, a "protein" refers to an amino acid sequence having 51 or more amino acids.

As used herein, a "polymer" refers to a molecule that comprises two or more linear units (also known as a "mers"), where each unit may be the same or different. Non-limiting examples of polymers include nucleic acids, peptides, and proteins, as well as a variety of hydrocarbon polymers (e.g., polyethylene, polystyrene) and functionalized hydrocarbon polymers, wherein the backbone of the polymer comprises a carbon chain (e.g., polyvinyl chloride, polymethacrylates). Polymers include copolymers, block copolymers, and branched polymers such as star polymers and dendrimers.

Methods of sequencing polymers using Msp porins are described herein. In addition, sequencing methods may be performed in methods analogous to those described in U.S. Pat. No. 7,189,503, incorporated herein by reference in its entirety. See also U.S. Pat. No. 6,015,714, incorporated herein by reference in its entirety. More than one read may be performed in such sequencing methods to improve accuracy. Methods of analyzing characteristics of polymers (e.g., size, length, concentration, identity) and identifying discrete units (or "mers") of polymers are discussed in the '503 patent as well, and may be employed with respect to the present Msp porins. Indeed, an Msp porin may be employed with respect to any method discussed in the '503 patent.

At present, several types of observable signals are being explored as readout mechanisms in nanopore sequencing and analyte detection. The originally proposed, most straightforward, and most explored readout method relies on an ionic "blockade current" or "copassing current" uniquely determined by the identity of a nucleotide or other analyte occupying the narrowest constriction in the pore. This method is referred to as "blockade current nanopore sequencing," or BCNS. Blockade current detection and characterization of nucleic acids has been demonstrated in both the protein pore α-hemolysin (αHL) and solid-state nanopores. Blockade current detection and characterization has been shown to provide a host of information about the structure of DNA passing through, or held in, a nanopore in various contexts.

In general, a "blockade" is evidenced by a change in ion current that is clearly distinguishable from noise fluctuations and is usually associated with the presence of an analyte molecule at the pore's central opening. The strength of the blockade will depend on the type of analyte that is present. More particularly, a "blockade" refers to an interval where the ionic current drops below a threshold of about 5-100% of the unblocked current level, remains there for at least 1.0 µs, and returns spontaneously to the unblocked level. For example, the ionic current may drop below a threshold of about, at least about, or at most about 5%, 10%, 15%, 20%, 25%, 30%, 35%, 40%, 45%, 50%, 55%, 60%, 65%, 70%, 75%, 80%, 85%, 90%, 95%, or 100%, or any range derivable therein. Blockades are rejected if the unblocked signal directly preceding or following it has an average current that deviates from the typical unblocked level by more than twice the rms noise of the unblocked signal. "Deep blockades" are identified as intervals where the ionic current drops <50% of the unblocked level. Intervals where the current remains between 80% and 50% of the unblocked level are identified as "partial blockades."

As used herein, the term "subject" refers to a living mammalian organism, such as a human, monkey, cow, sheep, goat, dogs, cat, mouse, rat, guinea pig, or transgenic species thereof. Optionally, the patient or subject is a primate. Non-limiting examples of human subjects are adults, juveniles, infants, and fetuses.

The term "nucleic acid" refers to a deoxyribonucleotide or ribonucleotide polymer in either single- or double-stranded form, and unless otherwise limited, encompasses known analogs of natural nucleotides that hybridize to nucleic acids in manner similar to naturally occurring nucleotides, such as peptide nucleic acids (PNAs) and phosphorothioate DNA. Unless otherwise indicated, a particular nucleic acid sequence includes the complementary sequence thereof. Nucleotides include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP, 2-thiothymidine triphosphate, pyrrolopyrimidine triphosphate, and 2-thiocytidine, as well as the alphathiotriphosphates for all of the above, and 2'-O-methyl-ribonucleotide triphosphates for all the above bases. Modified bases include, but are not limited to, 5-Br-UTP, 5-Br-dUTP, 5-F-UTP, 5-F-dUTP, 5-propynyl dCTP, and 5-propynyl-dUTP.

As used herein, a "drug" refers to any substance that may alter a biological process of a subject. Drugs may be designed or used for or in the diagnosis, treatment, or prevention of a disease, disorder, syndrome, or other health affliction of a subject. Drugs may be recreational in nature, that is, used simply to alter a biological process and not used for or in the diagnosis, treatment, or prevention of a disease, disorder, syndrome, or other health affliction of a subject. Biologics, which refer to substances produced by biological mechanisms involving recombinant DNA technology, are also encompassed by the term "drug." Drugs include, for example, antibacterials, antiinflammatories, anticoagulants, antivirals, antihypertensives, antidepressants, antimicrobials, analgesics, anesthetics, beta-blockers, bisphosphonates, chemotherapeutics, contrast agents, fertility medications, hallucinogens, hormones, narcotics, opiates, sedatives, statins, steroids, and vasodilators. Non-limiting examples of drugs may also be found in the Merck Index. Antibacterial drugs used in the treatment of tuberculosis, for example, include isoniazid, rifampicin, pyrazinamide, and ethambutol.

Methods employing a drug as an analyte may further comprise drug screening. For example, uptake of a drug into a cell or an organism may be investigated using an Msp porin by observing ion current blockades. Specific Msp porin constriction zones and/or vestibules with various sizes, electrostatic properties, and chemical properties can be constructed to closely emulate the desired pathway for drugs to enter or exit a cell or organism. These methods could greatly accelerate screening for drugs as well as drug design. Such studies have been performed with other porins, such as described by Pagel et al., J. Bacteriology 189:8593 (2007).

As used herein, a "biological warfare agent" refers to any organism or any naturally occurring, bioengineered, or synthesized component of any such microorganism capable of causing death or disease in plants or animals (including humans) or degradation of food or water supplies, or degradation of the environment. Non-limiting examples include Ebola viruses, Marburg virus, *Bacillus anthracis* and *Clostridium botulinum*, Variola major, Variola minor, anthrax, and ricin.

As used herein, a "pollutant" refers to a material that pollutes air, water, or soil. Non-limiting examples of pollutants include fertilizers, pesticides, insecticides, detergents, petroleum hydrocarbons, smoke, and heavy metal-containing substances, such as those containing zinc, copper, or mercury (e.g., methylmercury).

An analyte may be a "nanoscopic object," which is an object that is smaller than 100 nm in two of its dimensions.

Beads that may be employed include magnetic beads and optical beads. For example, one may use streptavidin-coated magnetic beads to apply an opposing force to the electrostatic forces that pull DNA through the tunnel of an Msp porin. In this latter technique a magnetic bead is attached to biotinylated DNA, and a force comparable to the electrostatic driving force (~10 pN) would be applied using a strong magnetic field gradient. See Gosse and Croquette, *Biophys. J.* 82:3314 (2002). In this way, the blockade-current readout would be unaffected, but the forces on the DNA could be independently controlled. Tens or hundreds of complete, independent reads of each DNA could then be correlated and assembled to reconstruct an accurate DNA sequence.

Optical beads manipulated by "optical tweezers" are also known in the art, and such methods may be applied to the Msp porins described herein. Optical tweezers are a common tool used to exert a force on a nanoscopic object. An analyte is attached on one end of the bead, while the other end may be inserted into the tunnel of the porin. The position and force of the bead is controlled and measured with the optical tweezers. Such methods control the passage of the analyte into the tunnel and allow for more control of the reading of the analyte, such as the reading of the units of a polymer. See, e.g., Trepagnier et al., *Nano Lett.* 7:2824 (2007) for a description of such methods in the context of artificial nanopores. U.S. Pat. No. 5,795,782, incorporated herein by reference, also discusses the use of optical tweezers.

Fluorescence resonance energy transfer (FRET), a well-known technique, may be employed in analytical methods described herein. For example, a fluorescent FRET-acceptor or FRET-donor molecule may be incorporated into an Msp porin. The analyte is then labeled with a matching FRET-donor or FRET-acceptor. When the matching FRET-donor is within the Förster distance to the FRET acceptor, energy transfer will likely occur. The resulting signal could be used for analytical purposes instead of or in addition to methods using ion current as described herein. Accordingly, methods of detection, identification, or sequencing may comprise FRET technology.

Other optical methods that may be employed include introducing optically active molecules into the interior of an Msp porin (such as the vestibule or the constriction zone). External light would be applied to affect the interior of the protein: such methods could be used to affect the translocation velocity of an analyte or could allow the analyte's entry or exit from the tunnel, offering controlled passage of the analyte. Alternatively, optical pulses focused onto the pore could be used to heat the pore to affect how it interacts with the analyte. Such control could be very fast as the heat from a small volume of a focal point would dissipate rapidly. Methods of controlling the translocation velocity of an analyte may therefore employ such optically active molecules or optical pulses.

Manipulation of translocation velocity may also be accomplished by attaching an object to one end of an analyte, and the other end of the analyte then interacts with the Msp porin. The object may be a bead (e.g., a polystyrene bead), a cell, a large molecule such as streptavidin, neutravidin, DNA, etc., or a nanoscopic object. The object could then be subjected to a fluid flow our could be subject to passive viscous drag.

"Molecular motors" are well-known in the art and refer to a molecule (e.g., an enzyme) that physically interacts with an analyte, such as a polymer (e.g., a polynucleotide), and is capable of physically moving the analyte with respect to a fixed location, such as the vestibule, constriction zone, or tunnel of an Msp porin. Although not intending to be bound by theory, molecular motors utilize chemical energy to generate mechanical force. A molecular motor may interact with each unit (or "mer") of a polymer in a sequential manner. Non-limiting examples of molecular motors include DNA polymerases, RNA polymerases, helicases, ribosomes, and exonucleases. Non-enzymatic motors are also known, such as virus motors that pack DNA. See Smith et al., Nature 413:748 (2001). A variety of molecular motors and desirable properties of such motors are described in U.S. Pat. No. 7,238,485, which is incorporated herein by reference in its entirety. A molecular motor may be disposed on the cis side or the trans side of an Msp porin and may optionally be immobilized, such as described by the '485 patent. Methods of incorporating a molecular motor into an Msp porin may be performed using methods described in the '485 patent. Systems and apparatuses described in the '485 patent may be employed with respect to an Msp porin described herein as well. Indeed, any embodiment discussed in the '485 patent may be employed using an Msp porin, as described herein. Molecular motors are also discussed in, e.g., Cockroft et al., J. Amer. Chem. Soc. 130:818 (2008); Benner et al., Nature Nanotech. 2:718 (2007); and Gyarfas et al., ACS Nano 3:1457 (2009).

A molecular motor is typically employed to regulate the rate or translocation velocity at which an analyte interacts with an Msp porin. Any Msp protein described herein may comprise a molecular motor. Optionally, a molecular motor is employed to decrease the rate at which an analyte enters an Msp porin tunnel or to decrease the translocation velocity at which an analyte translocates through an Msp porin tunnel. Optionally, the translocation velocity or average translocation velocity is less than 0.5 nm/µs. Optionally, the translocation velocity or average translocation velocity is less than 0.05 nm/µs. Optionally, the translocation velocity or average translocation velocity is less than 1 nucleotide/µs. Optionally, the translocation velocity or average translocation velocity is less than 0.1 nucleotide/µs. Optionally, the rate of movement of an analyte ranges from greater than 0 Hz to 2000 Hz. Here, rate refers to the number of subunits (or "mers") of a regular polymer advancing in one second (Hz). Optionally, the range is between about 50-1500 Hz, 100-1500 Hz, or 350-1500 Hz. Optionally, the rate of movement is about, at most about, or at least about 25, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 Hz, or any range derivable therein. The rate may be controlled by the use of a molecular motor that moves an analyte at a substantially constant rate, at least for a portion of time during a characterization. In addition, the range of rate of movement may depend on the molecular motor. For example, for an RNA polymerase, a range may be 350-1500 Hz; for a DNA polymerase, a range may be 75-1500 Hz; and for ribosomes, helicases, and exonucleases, a range may be 50-1500 Hz.

Recording and detection techniques that may be employed in the methods described herein. In addition, U.S. Pat. Nos. 5,795,782 and 7,189,503, incorporated herein by reference in its entirety, also describes recording methods and instrumentation that may be employed with respect to Msp porins, as well as methods for optimizing conductance readings. U.S. Pat. No. 6,746,594, incorporated herein by reference in its entirety, describes a support for thin films containing nanopores and methods for using such supports that may be employed with respect to the Msp porins described herein.

Further provided are vectors comprising any of the nucleic acids described herein. As used herein, a vector can comprise nucleic acid molecules encoding a single-chain Msp nanopore (e.g., a single-chain Msp dimer or a single-chain Msp octamer), wherein the nucleic acid molecule is operably linked to an expression control sequence. Suitable vector backbones include, for example, those routinely used in the art such as plasmids, artificial chromosomes, BACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

In another aspect, a cultured cell is provided that is transfected with a vector comprising the nucleic acids described herein. In this regard, a cell is successfully transfected with a vector when the transcription machinery of the intact cell has access to the nucleic acid template for the production of mRNA. Protocols to facilitate transfection of vectors into cells are well known in the art.

Provided herein are the progeny of a cultured cell that was stably transfected with the vector as described above. Such progeny will contain copies of the vector without having undergone the transfection protocol and are capable of transcribing the nucleic acids contained in vector under the control of an expression control sequence. Techniques utilizing cultured cells transfected with expression vectors to produce quantities of polypeptides are well known in the art. See, for example, Wang, H., et al., *J. Virology* 81:12785 (2007).

Also provided herein is a mutant bacterial strain capable of inducible Msp expression. The mutant bacterial strain comprises a deletion of a wild-type MspA, a deletion of a wild-type MspC, a deletion of a wild-type MspD, and a vector comprising an inducible promoter operably linked to a Msp monomer nucleic acid sequence. Optionally, the mutant bacterial strain comprises a *M. smegmatis* strain ML16. Optionally, the Msp monomer nucleic acid sequence encodes an Msp monomer selected from the group consisting of a wild-type MspA monomer, a wild-type MspC monomer, a wild-type MspD monomer, and mutant monomers thereof. Optionally, the inducible promoter comprises an acetamide inducible promoter.

Optionally, the mutant bacterial strain further comprises a deletion of a wild-type MspB. The mutant bacterial strain comprising a deletion of a wild-type MspB can further comprise a vector with a constitutive promoter operably linked to a nucleic acid sequence that encodes an Msp porin or monomer. Optionally, the Msp porin or monomer is selected from the group consisting of a wild-type MspA, a wild-type MspC, a wild-type MspD, and mutants thereof. Optionally, the vector comprises any of the nucleic acids described herein.

Also provided is a method of producing a full or partial single-chain Msp porin. The method comprises transforming a mutant bacterial strain. The mutant strain comprises a deletion of a wild-type MspA, a wild-type MspB, a wild-type MspC, a wild-type MspD, and a vector comprising an inducible promoter operably linked to a Msp monomer nucleic acid sequence. The mutant strain is transformed with a vector comprising a nucleic acid sequence capable of encoding a single-chain Msp porin. The single-chain Msp porin is then purified from the bacteria. Optionally, the single-chain Msp porin comprises a single-chain MspA porin. Optionally, the vector comprises any of the nucleic acids described herein.

Further provided is a method of sequencing nucleic acids or polypeptides using a single-chain Msp porin. The method comprises creating a lipid bilayer comprising a first and second side, adding a purified Msp porin to the first side of the lipid bilayer, applying positive voltage to the second side of the lipid bilayer, translocating an experimental nucleic acid or polypeptide sequence through the single-chain Msp porin, comparing the experimental blockade current with a blockade current standard, and determining the experimental sequence. Optionally, the single-chain Msp porin comprises a wild-type MspA monomer or a mutant monomer thereof. Optionally, the Msp monomer comprises an MspA paralog or homolog monomer selected from Table 1.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In any embodiment discussed in the context of a numerical value used in conjunction with the term "about," it is specifically contemplated that the term about can be omitted.

Following long-standing patent law, the words "a" and "an," when used in conjunction with the word "comprising" in the claims or specification, denotes one or more, unless specifically noted.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed. It is therefore contemplated that any embodiment discussed in this specification can be implemented with respect to any method, compound, protein, porin, peptide, polypeptide, multimer, monomer, nucleic acid, vector, strain, cultured cell, system, or composition, etc., described herein, and vice versa. For example, any protein described herein can be employed in any method described herein.

Publications cited herein and the material for which they are cited are hereby specifically incorporated by reference in their entireties.

The following examples are provided for the purpose of illustrating, not limiting, the material disclosed herein.

EXAMPLES

Example 1: Materials and Methods for Examples 1-7

Homogeneous ssDNA oligonucleotides $dA_{50}$, $dC_{50}$, and $dT_{50}$ (SEQ ID NO:10, SEQ ID NO:16, and SEQ ID NO:17, respectively) and hairpin constructs hp08 (5' GCTGTTGC TCTCTC GCAACAGC $A_{50}$ 3') (SEQ ID NO:4), hp10 (5' GCTCTGTTGC TCTCTC GCAACAGAGC $A_{50}$ 3') (SEQ ID NO:5), and hp12 (5' GCTGTCTGTTGC TCTCTC GCAACAGACAGC $A_{50}$ 3') (SEQ ID NO:6) were synthesized by Integrated DNA Technologies, (IDT; Coralville, Iowa).

Bacterial Strains and Growth Conditions. All bacterial strains used in this study are listed in Table 5. Mycobacteria were grown at 37° C. in Middlebrook 7H9 liquid medium (Difco) supplemented with 0.2% glycerol, 0.05% Tween 80® or on Middlebrook 7H10 agar (Difco) supplemented with 0.2% glycerol. *Escherichia coli* DH5a was used for all cloning experiments and was routinely grown in Luria-Bertani (LB) medium at 37° C. Hygromycin was used at concentrations of 200 μg/mL for *E. coli* and 50 μg/mL for *M. smegmatis*.

TABLE 5

Strains and plasmids.

| Strain/Plasmid | Parent Strain and Relevant Genotype |
|---|---|
| Strain | |
| E. coli DH5α | recA1, endA1, gyrA96, thi; relA1, hsdR17($r_K^-$, $m_K^+$), supE44, φ80ΔlacZΔM15, ΔlacZ(YA-argF)UE169 |
| M. smegmatis ML16 | ML15, ΔmspA::FRT, ΔmspC::FRT, ΔmspD::FRT, attB::loxp, FRT |
| Plasmid | |
| pMS2 | ColE1 origin, PAL5000 origin, Hyg$^R$ |
| pMN016 | p$_{smyc}$-mspA, ColE1 origin, PAL5000 origin, Hyg$^R$ |
| pMN035 | p$_{smyc}$-rv1698, ColE1 origin, PAL5000 origin, Hyg$^R$ |
| pML904 | pMN016 derivative, mspA D90N/D91N/D93N (m1mspA) |
| pML840 | pML904 derivative, mspA D90N/D91N/D93N/D118R |
| pML841 | pML840 derivative, mspA D90N/D91N/D93N/D118R/E139R |
| pML843 | pML840 derivative, mspA D90N/D91N/D93N/D118R/E139K |
| pML844 | pML843 derivative, mspA D90N/D91N/D93N/D118R/E139K/D134R (m2mspA) |

The annotation HygR indicates resistance to hygromycin. MspA, mspC, and mspD are porin genes of *M. smegmatis*.

Site-Directed Mutagenesis of mspA. The M1MspA and M2MspA mutant monomers were constructed in a stepwise fashion by site-directed mutagenesis using the combined chain reaction (CCR) as described by Bi and Stambrook, *Nucl. Acids Res.* 25:2949 (1997). The plasmid pMN016 carries a p$_{smyc}$-mspA transcriptional fusion (Stephan et al., *Mol. Microbiol.* 58:714 (2005)) and was used as a template. The oligonucleotides psmyc1 and pMS-seq1 as forward and reverse primers, respectively, and an appropriate mutagenesis primer (Table 6) were used in CCR. Three subsequent mutations were introduced into mspA to construct the m1mspA gene. Three further mutations were introduced into m1mspA to yield m2mspA. All plasmids were verified by sequencing the entire mspA gene before they were transformed into the triple porin mutant *M. smegmatis* ML16 (Stephan et al., *Mol. Microbiol.* 58:714 (2005)) for protein production.

Single Tunnel Experiments. Bilayers were made with diphytanoyl-PA and diphytanoyl-PC lipids prepared in equal or unequal proportion and were formed across a horizontal, ~20 μm-diameter aperture in Teflon as described (Akeson et al., *Biophys. J.* 77:3227 (1999)). MspA porins were added to one side of the bilayer (cis side) at a concentration of ~2.5 ng/mL. The cis side was grounded, and positive voltage was applied to the trans side of the bilayer. An Axopatch-1B patch-clamp amplifier (Axon Instruments) was employed to apply voltage across the bilayer and measure the ionic current flowing through the pore. The analog signal was low-pass-filtered at 50 kHz with a 4-pole Bessel filter. The amplified, filtered signal was digitized at 250 kHz. Data acquisition was controlled with custom software written in LabWindows/CVI (National Instruments). All experiments were performed at 21±2° C. in 1 M KCl, 10 mM Hepes/KOH buffered at pH 8.

Data Analysis. Data analysis was implemented with custom software written in Matlab (The MathWorks; Natick, Mass.). Blockades were identified as intervals where the ionic current dropped below a threshold of 80% of the unblocked current level, remained there for at least 12 μs, and returned spontaneously to the unblocked level. Blockades were rejected if the unblocked signal directly preceding or following it had an average current that deviated from the typical unblocked level by more than twice the rms noise of the unblocked signal. Blockades were also rejected if they occurred within 26 μs of another blockade. Deep blockades were identified as intervals where the ionic current dropped <50% of the unblocked level. Intervals where the current remained between 80% and 50% of the unblocked level were identified as partial blockades. Each event was parameterized by the dwell times and average currents of its constituent partial and deep subintervals.

Figure 8:
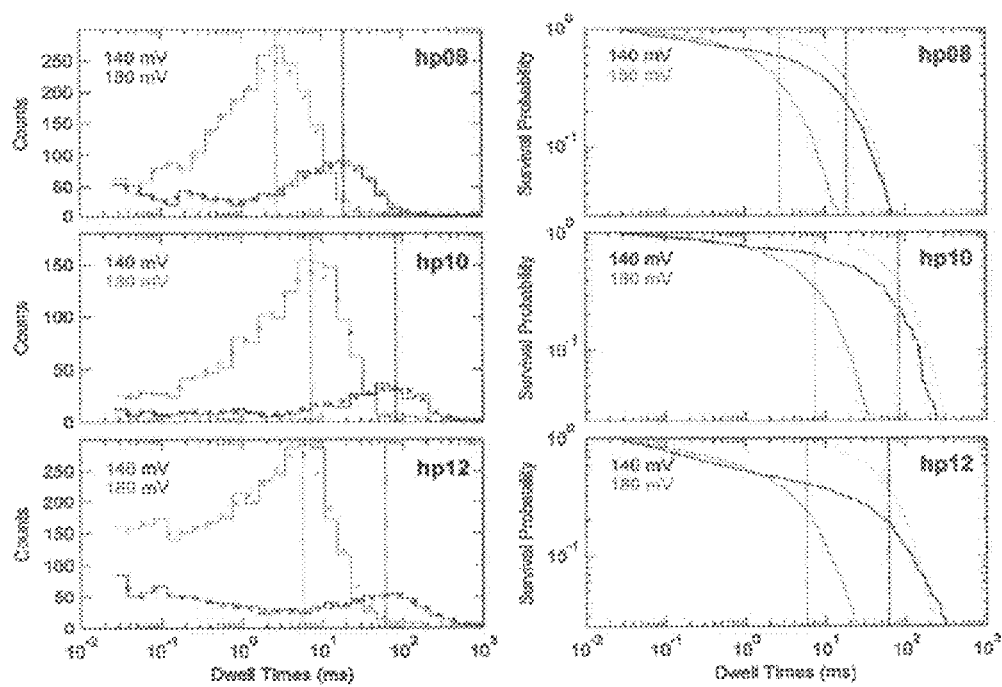
FIG. 8 provides a detailed look at dwell time distributions of hairpin construct deep blockades in the M1MspA porin. Panels on the Left show well time histograms with logarithmically spaced bins (stair plots) and corresponding kernel-smoothed density estimates of the probability distribution of the $\log_{10}$ of the dwell times (x). The maximum of these smoothed density estimates, $t_D$, was used to parameterize the dwell time distributions. Vertical lines show the $t_D$ values. Panels on the Right show survival probability curves derived from the dwell time data (solid lines) and single decaying exponentials, with time constants set to the $t_D$ values of each data set (dashed lines). The data clearly deviate from simple exponential behavior. However, it is reasonable to make qualitative comparisons between the $t_D$ value and exponential time constants used in other investigations (Kasianowicz et al., *Proc. Nat'l Acad. Sci. USA*, 93:13770 (1996)) because both parameters reflect similar aspects of the dwell time distributions.

The $t_D$ values used to parameterize the hairpin deep blockade dwell time distributions were estimated as the peak of the probability density distribution of the $\log_{10}$ of the dwell times (FIG. 8). This distribution was estimated with the Matlab Kernel smoothing density estimator using a normal kernel function and a width of 0.15. Trans-bilayer data was analyzed by detecting abrupt changes in the

TABLE 6

Oligonucleotides.

| Oligonucleotide | Sequence (5' to 3' direction) | Purpose |
|---|---|---|
| P$_{smyc}$1 | CGACCAGCACGGCATACATC (SEQ ID NO: 41) | Amplification and sequencing |
| pMS-SEQ1 | CGTTCTCGGCTCGATGATCC (SEQ ID NO: 42) | Amplification and sequencing |
| MspA909193NFP | CCTGATC<u>AAC</u><u>AAC</u>GGT<u>AAC</u>ATCACCGC (SEQ ID NO: 43) | Cloning of pML904 |
| MspA_118R | CTGGGCA<u>CGC</u>CTGGGCAACGG (SEQ ID NO: 44) | Cloning of pML840 |
| MspA_139R | TCCGGCGCC<u>CGC</u>GGTGGCGTG (SEQ ID NO: 45) | Cloning of pML841 |
| MspA_139K | GGCGCC<u>AAG</u>GGTGGCGTGG (SEQ ID NO: 46) | Cloning of pML843 |
| MspA_134R | CGTTCTCGGTC<u>CGC</u>GTCTCC (SEQ ID NO: 47) | Cloning of pML844 |

The codons that were altered to introduce the MspA mutations are underlined.

conductance from less than 1 nS to greater than 1 nS. The voltage at which these changes occurred was recorded and then summarized in the histograms shown in FIGS. 9E-9G.

In all experiments, the pores were oriented such that the "entrance" (FIG. 1) was exposed to the cis compartment of the apparatus.

All of the hairpin data displayed in FIGS. 5-8 were derived from data taken on the same long-lived M1MspA porin. The homopolymer data presented in Example 5 were obtained with a different long-lived M1MspA porins than the hairpin data, but there is quantitative agreement between extensive hairpin datasets taken on the two pores.

Example 2: Blockade Characteristics of Wild-Type MspA (WTMspA) Porins with and without Analyte Purification of MspA porins. MspA porins were selectively extracted from *M. smegmatis* and purified by subsequent anion exchange and gel filtration chromatography as described (Heinz and Niederweis, *Anal. Biochem.* 285:113 (2000); Heinz et al., *Methods Mol. Biol.* 228:139 (2003)).

Figure 2:
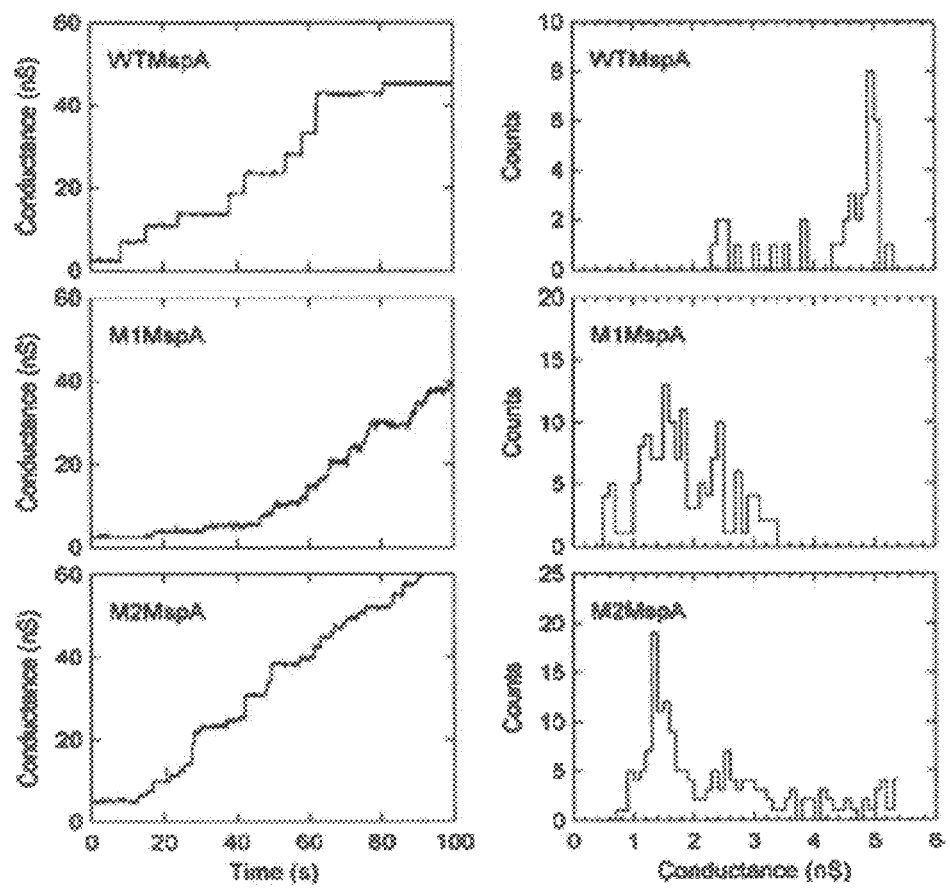
FIG. 2 shows the results of assays of tunnel-forming activity and single-tunnel conductance for WTMspA, mutant D90N/D91N/D93N (M1MspA, also called M1-NNN), and mutant D90N/D91N/D93N/D118R/E139K/D134R (M2MspA, also called M2-NNN) porins. The Left panels show bilayer conductance over time when an MspA porin is present in the solution (1 M KCl, 20° C.) bathing the bilayer. Stepwise increases in conductance are interpreted as insertions of MspA porins into the bilayer. On the Right are histograms of the sizes of these conductance steps. The WTMspA, M1MspA, and M2MspA porin histograms summarize 40 insertions from 3 repeated experiments, 144 insertions from 3 repeated experiments, and 169 insertions from 5 repeated experiments, respectively.
Figures 3A, 3B:
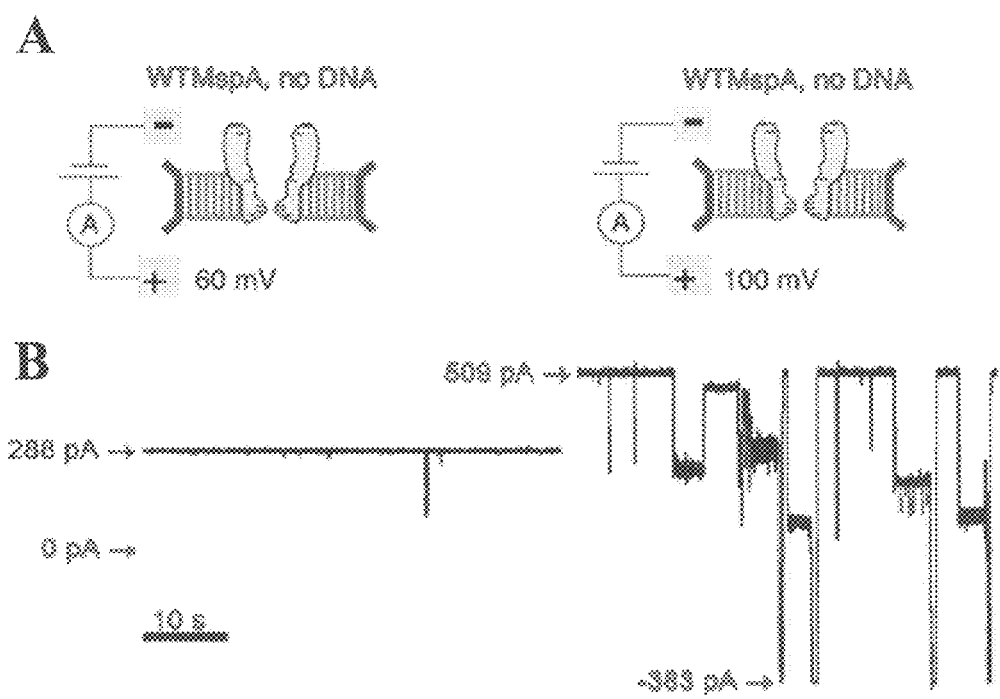
FIGS. 3A and 3B show spontaneous blockade behavior of WTMspA porins.

Consistent with previous results (Niederweis et al., *Mol. Microbiol.* 33:933 (1999)), the purified protein demonstrated high tunnel-forming activity with a most frequent conductance of 4.9 nS in 1.0 M KCl at ~20° C. (FIG. 2). The cis compartment was held at ground and positive voltage was applied to the trans compartment (FIG. 3A). Above ~60 mV, the WTMspA porin demonstrated frequent, spontaneous blockades of the ionic current in the absence of ssDNA (FIG. 3B). Some spontaneous blockades were transient, and others required reversal of the voltage to reestablish the unblocked current level. Despite this behavior, there remained intervals of steady, unobstructed signal lasting tens of seconds for voltages up to ~100 mV (FIG. 3B). The addition of ~2-8 µM $dC_{50}$ (SEQ ID NO:48) ssDNA to the cis compartment did not lead to a noticeable enhancement or alteration of these blockade characteristics. Above ~100 mV the spontaneous blockades were so frequent that ssDNA detection experiments were impractical.

One explanation for the apparent absence of ssDNA interactions with the WTMspA porin is the high density of negative charge in the pore (FIG. 1). Electrostatic interaction with the negatively-charged tunnel interior likely inhibits the entry of DNA into the pore. To address this issue aspartate residues in the constriction zone were replaced with asparagines (FIG. 1). The resulting MspA mutant D90N/D91N/D93N (M1MspA) porin is discussed in Example 3.

Example 3: Blockade Characteristics of MspA Mutant M1MspA Porin with and without Analyte Experimental.

Figure 4:
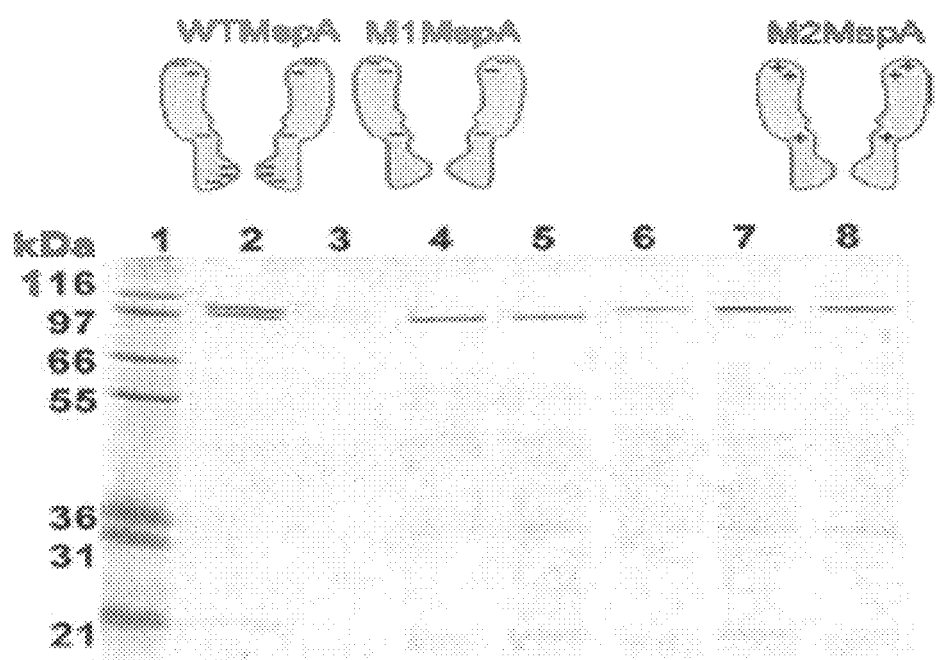
FIG. 4 shows the expression of mutant MspA monomers in an electrophoretic gel. Raw extract (13 µL) was added to each lane. Gel was stained with Coomassie blue. Lane 1: protein mass marker; Lane 2: WTMspA; Lane 3: no MspA; Lane 4: mutant M1MspA; Lane 5: mutant D90N/D91N/D93N/D118R; Lane 6: mutant D90N/D91N/D93N/D118R/E139R; Lane 7: mutant D90N/D91N/D93N/D118R/E139K; Lane 8: mutant M2MspA. Mutants in lanes 5-7 were constructed, extracted and assayed to ensure that expression and tunnel-forming activity were retained for each successive amino acid replacement. Diagrams above the gel show schematically the approximate location and polarity of the amino acids mutated in this experiment.
Figures 5A, 5B, 5C:
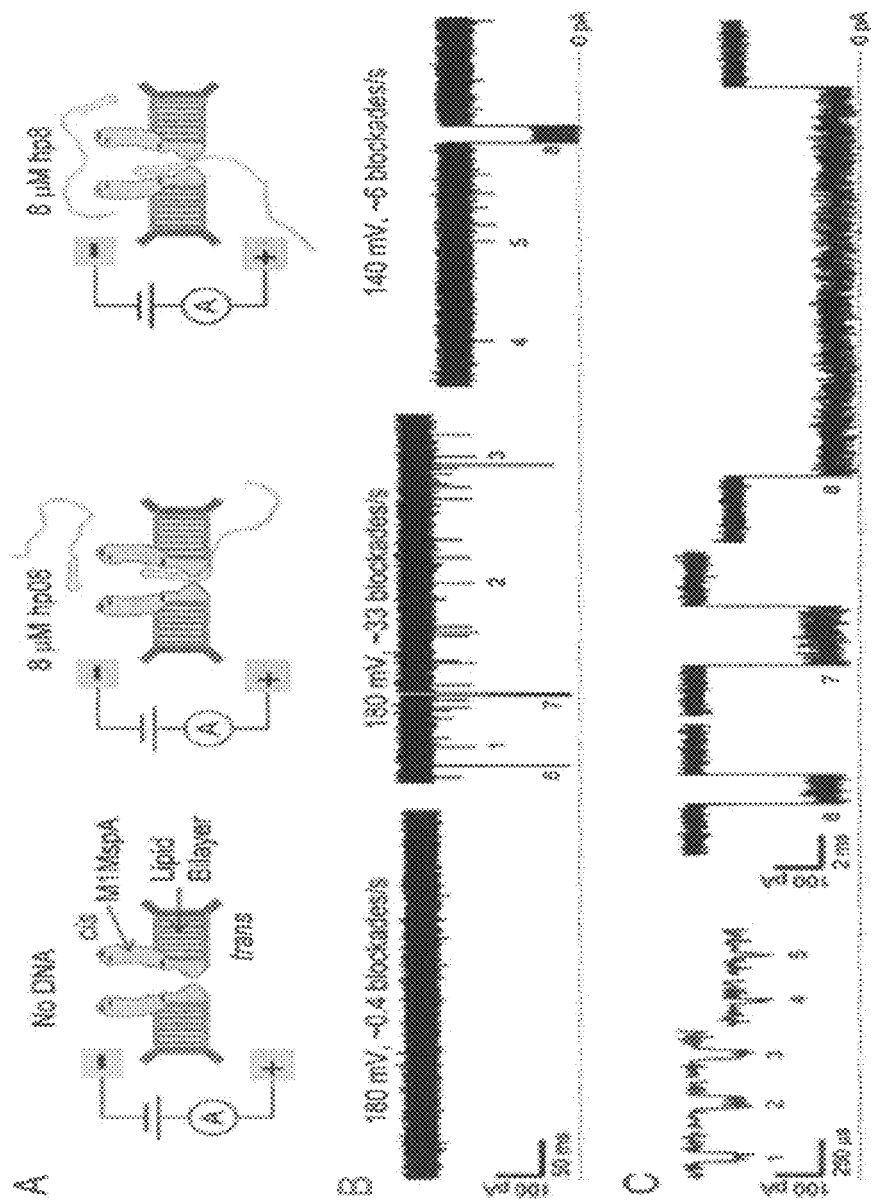
FIGS. 5A-5C show detection of ssDNA hairpin constructs with M1MspA porins.
Figure 6:
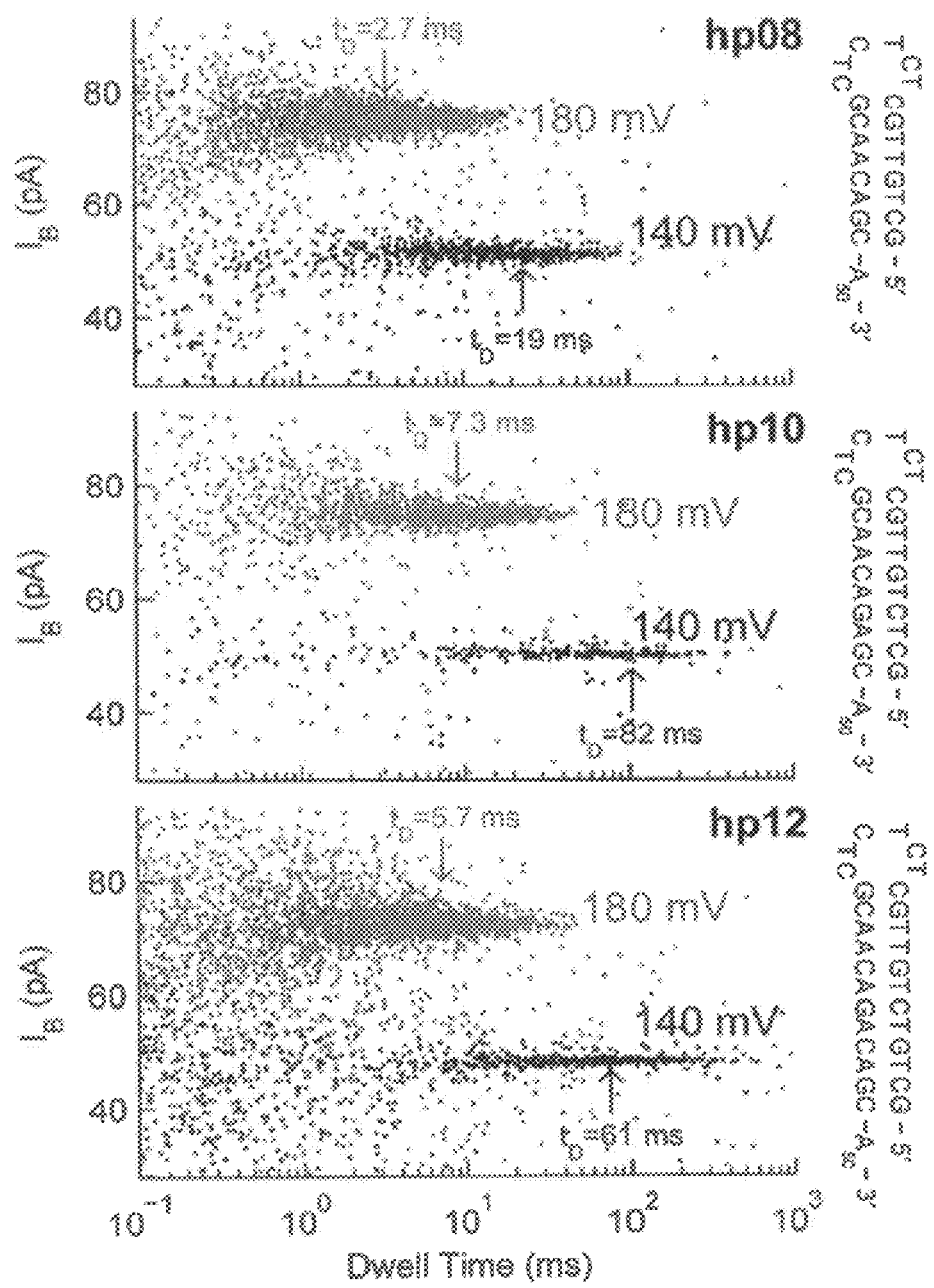
FIG. 6 shows characteristics of deep blockades from hairpin constructs in the M1MspA porin. The coordinates of each point give the duration and average current of 1 deep blockade. Black and gray data were acquired at 140 and 180 mV, respectively. The mode of the $\log_{10}$ of the deep blockade dwell times, $t_D$, is indicated for each dataset. Diagrams at right show the sequence of each hairpin construct: hp08 (5' GCTGTTGC TCTCTC GCAACAGC $A_{50}$ 3') (SEQ ID NO:4), hp10 (5' GCTCTGTTGC TCTCTC GCAACAGAGC $A_{50}$ 3') (SEQ ID NO:5), and hp12 (5' GCTGTCTGTTGC TCTCTC GCAACAGACAGC $A_{50}$-3') (SEQ ID NO:6).
Figure 7:
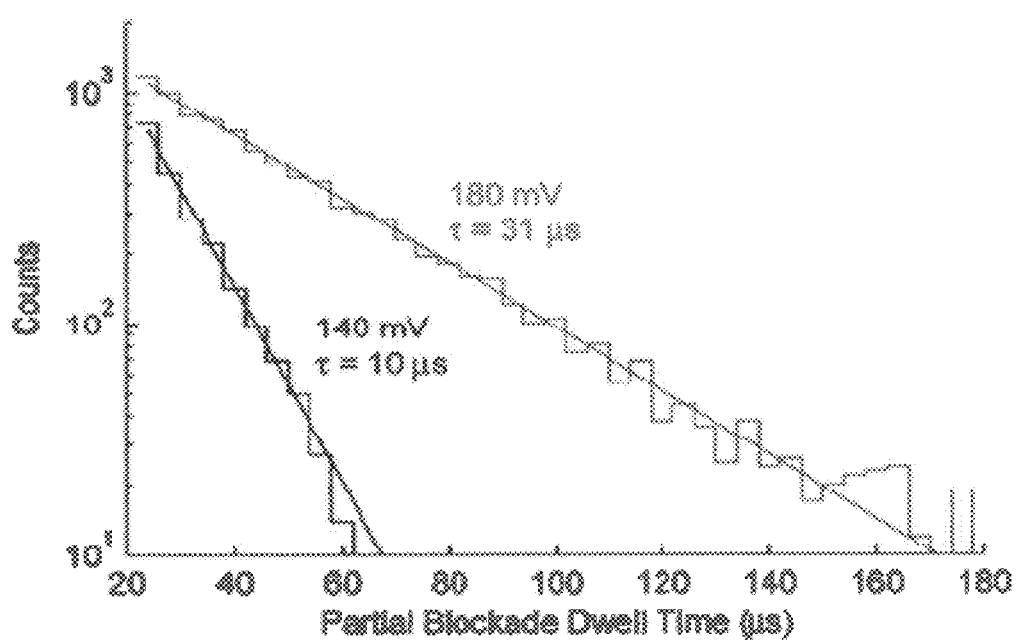
FIG. 7 is a graph showing partial blockade dwell time distributions for hp08 (SEQ ID NO:4) in the M1MspA porin. Distributions are well-fitted by single exponentials. The partial blockades at 180 mV have a time constant that is a factor of ~3 longer than at 140 mV.

As noted in Example 2, electrostatic interactions between ssDNA and the tunnel of the WTMspA porin may affect translocation of ssDNA through the pore. The MspA mutant D90N/D91N/D93N (M1MspA, also referred to as M1-NNN) was designed to test this theory. The M1MspA porin was expressed and purified from the *M. smegmatis* strain ML16 that lacks most endogenous porins (Stephan et al., *Mol. Microbiol.* 58:714 (2005)). The expression levels of the M1MspA porin (FIG. 4) and its tunnel-forming activity were similar to the WTMspA porin, whereas the conductance was reduced by a factor of 2-3 (FIG. 2). Further, the frequency of spontaneous blockades was dramatically reduced in the M1MspA porin, making it possible to conduct DNA detection experiments at voltages up to and above 180 mV (FIG. 5).

ssDNA hairpin constructs were used to investigate the interaction of DNA with the M1MspA porin. Each construct had a 50-nt poly-dA overhang on the 3' end, a dsDNA duplex region of variable length (8, 10, and 12 bp for constructs hp08 (SEQ ID NO:4), hp10 (SEQ ID NO:5), and hp12 (SEQ ID NO:6), respectively), and a 6-nt loop (FIG. 6). At 180 mV, the addition of ~8 µM hp08 ssDNA to the cis compartment caused the rate of transient ionic current blockades to increase from 0.1-0.6 blockades per second to 20-50 blockades per second (FIG. 5). Blockade rates were proportional to DNA concentration and were strongly voltage-dependent, decreasing ~3-fold for a 20-mV decrease in the applied voltage. Blockades long enough to be well-resolved were either partial blockades where the ionic current was reduced to between 80% and 50% of the unblocked level or deep blockades where the ionic current was reduced to less than 50% of the unblocked level (FIG. 5C). Blockades exhibiting both partial and deep subsegments were very rare. Partial blockades lasted tens to hundreds of microseconds and their dwell times increased with increasing voltage (FIGS. 5C and 7). Deep blockades lasted hundreds of microseconds to hundreds of milliseconds and their dwell times decreased with increasing voltage (FIGS. 6 and 7). These trends were observed in experiments with all three hairpins.

Analysis.

In analogy to similar signals observed with αHL (Butler et al., *Biophys. J.* 93:3229-40 (2007)), the partial blockades are interpreted as DNA entry into the M1MspA porin vestibule without threading of the single-stranded segment through the tunnel constriction. For this mechanism, a moderate reduction of the ionic current is expected. Without meaning to be limited by theory, the increase in dwell time with voltage (FIG. 7) most likely results from an increasing electrostatic barrier against escape of a DNA molecule from the vestibule back into the cis compartment. This explanation for the dwell time increase can be understood within a kinetic framework where decay of the polymer from the vestibule occurs via the two first-order processes of escape against the applied voltage gradient and threading of one end through the constriction. The lifetime is then the inverse of the sum of the rate constants for these processes. This lifetime will increase with voltage if (i) the escape rate constant decreases with voltage and (ii) its decrease dominates any changes in the threading rate constant.

For the deep blockades, the clear decrease in dwell times with increasing voltage is inconsistent with any process involving escape of the DNA back into the cis compartment. Both the degree of ionic current reduction and the voltage dependence of the dwell times are consistent with a process where the single stranded polydA segment is driven through the ~1-nm-diameter constriction until the ~2.2-nm-diameter DNA duplex reaches the constriction and arrests translocation (FIG. 5A). The hairpin construct remains in this threaded configuration until either unzipping of the DNA duplex (Vercoutere et al., *Nat. Biotech.* 19:248-52 (2001); Sauer-Budge et al., *Phys. Rev. Lett.* 90:238101 (2003); Mathe et al., *Biophys. J.* 87:3205-12 (2004)) or a conformational rearrangement of the M1MspA porin constriction zone allows translocation to be completed. Without being bound by theory, the unzipping mechanism of translocation completion appears most plausible because passage of a dsDNA helix would require the constriction to approximately double in diameter, disrupting the hydrogen bonds of the β-barrel flanking the constriction (Faller et al., *Science* 303:1189 (2004)) and potentially exposing the hydrophobic regions of the protein and bilayer interior to water.

The hairpin deep blockades in the M1MspA porin had very broad dwell time distributions that were not well described by simple exponentials or sums of exponentials (FIG. 8). To parameterize the distributions, the mode of the logarithm of the deep blockade dwell times, $t_D$, corresponding in FIG. 6 to the dwell time with the highest density of blockades was used (FIG. 8). For all voltages, hp08 had the shortest $t_D$. Below 160 mV, hp10 and hp12 had similar $t_D$. However, above 160 mV hp10 had consistently longer $t_D$ than hp12. These observations are somewhat different than those from αHL, where hairpin blockade dwell time distributions were modeled with single exponentials and hairpins with larger standard free energies of formation consistently produced longer deep blockades (Vercoutere et al., *Nat. Biotechnol.* 19:248 (2001); Mathe et al., *Biophys. J* 87:3205 (2004)). Assuming the deep blockades are produced by translocation with duplex dissociation as the rate-limiting step, then this process is 10-100 times slower in the M1MspA porin than in αHL (Mathe et al., *Biophys. J.* 87:3205 (2004)). Interestingly, the hp10 blockades persisted longer than hp12 blockades. In six repeated experiments with hp10 at 180 mV, an average unblocked current level of 340±7 pA and an average $t_D$ of 9±1 ms (mean±SEM) were each observed.

Example 4: Transbilayer Detection with the M1MspA Porin

Theory.

To obtain direct proof that DNA translocates through MspA, the transbilayer detection technique illustrated in FIG. 9 and pioneered by Nakane et al. was employed (Nakane et al., Biophys. J. 87:615 (2004)). An ssDNA probe molecule with a bulky anchor complex at one end is electrophoretically driven into the nanopore. The free ssDNA end threads through the pore into the trans compartment until the anchor halts translocation. If the trans compartment contains short ssDNA target molecules that are complementary to the end of the ssDNA probe, then the probe and target can hybridize. If hybridization occurs, the probe is locked in a threaded configuration until the application of a sufficiently negative voltage causes the probe to dissociate from the target and exit into the cis compartment. If hybridization does not occur for stochastic reasons or because the probe end is not complementary to the target, or if there are no target molecules in the trans compartment, then a negative voltage is not needed for the probe to exit back into the cis compartment. The appearance of blockades that are only cleared by sufficiently negative voltage is evidence that the ssDNA probe has threaded through the nanopore to the trans compartment and hybridized to the target DNA.

Experimental.

Probe molecules were constructed comprising 75-nt-long ssDNA molecules that were attached to a neutravidin (nA) anchor on their biotinylated 5' end and had a heterogeneous 15-nt-long complementary sequence on their 3' end. nA was obtained from Invitrogen (Carlsbad, Calif.). Two different 5'-biotinylated ssDNA constructs, 5'-bt-dC$_6$dA$_{54}$ d(CTCT-ATTCTTATCTC)-3' (SEQ ID NO:7) and 5'-bt-dC$_6$dA$_{54}$ d(CACACACACACAC)-3' (SEQ ID NO:8), were synthesized by IDT. nA and the ssDNA constructs were mixed at a concentration of 50 μM in a 1:1 ratio in the experimental 1M KCl buffer and stored at −20° C. until immediately before use. The 15-nt-long target DNA, 3 '-GAGA-TAAGAATAGAG-5' (SEQ ID NO:9) was synthesized by IDT, suspended in the experimental buffer, and stored at −20° C. until immediately before use. The trans compartment was preloaded with ~100 μM target DNA and the cis compartment was filled with DNA-free buffer. After a bilayer was formed, the cis compartment was perfused to remove any target DNA that diffused through the aperture. Once a stable M1MspA porin was established, the nA-ssDNA complexes were added to the trans compartment to a final concentration of ~1 μM. Custom experimental control software written in LabWindows was used to continuously monitor the current and apply the appropriate voltages.

Figures 9A, 9B, 9C, 9D:
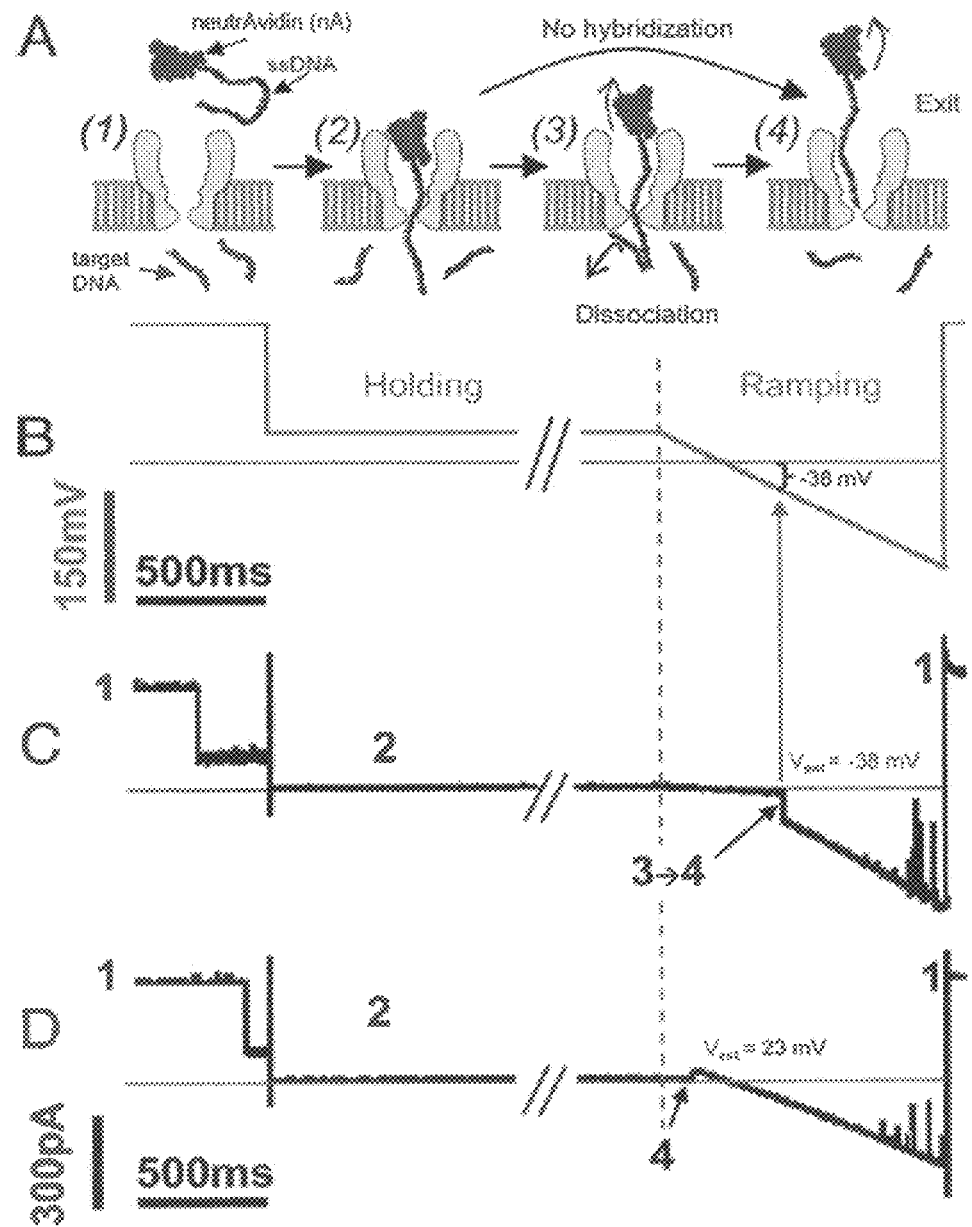
FIGS. 9A-9G show data acquired from transbilayer probe experiments.

Indefinite deep current blockades were observed when the probe molecules were driven into the pore from the cis compartment with 180 mV. For the transbilayer experiments, probe molecules were captured with 180 mV. After a brief delay to ensure that the ssDNA was threaded as far as possible through the M1MspA porin, the voltage was reduced to 40 mV and held at that level for 5 s to allow one of the 15-nt-long target ssDNA to anneal to the probe's complementary end. The voltage was then ramped down at a rate of 130 mV/s. For each event, the probe exit voltage, $V_{exit}$, was identified as the voltage at which a large and abrupt increase in the conductance was observed while ramping (FIGS. 9C and 9D).

Transbilayer data were analyzed by detecting abrupt changes in the conductance from <1 to >1 nS. The voltage at which these changes occurred was recorded and then summarized in the histograms shown in FIGS. 9E-9G. See Materials and Methods in Example 1 for further information regarding data analysis.

Analysis.

Figures 9E, 9F, 9G:
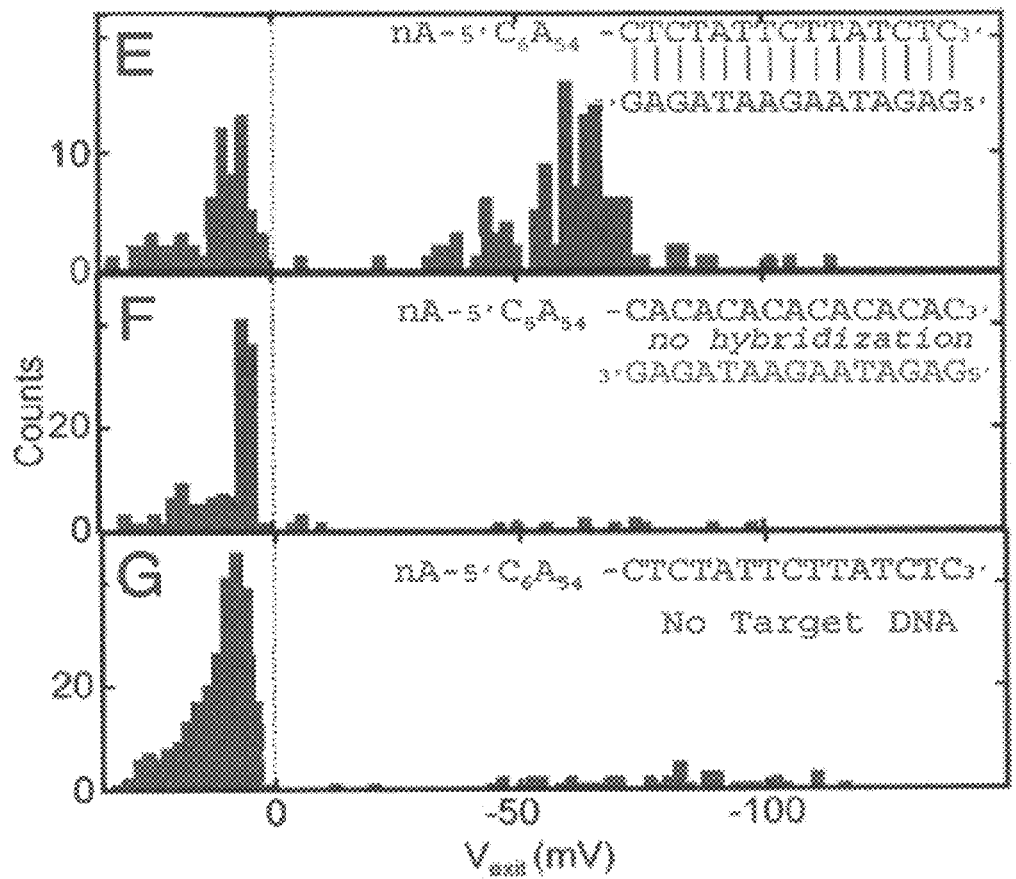

Histograms of $V_{exit}$ from experiments with three different probe/target combinations are shown in FIG. 9. When the probe DNA is complementary to the target DNA (FIG. 9E) a significant number of $V_{exit}$ are negative, indicating probe/target hybridization. In six repeated experiments with complementary probe/target molecules, similar populations of negative $V_{exit}$ were observed. In five repeated experiments where the ssDNA 3' end was not complementary to the target molecules (FIG. 9F) and in one experiment without target DNA (FIG. 9G), negative $V_{exit}$ values were rarely observed. On two different nanopores both complementary and noncomplementary probe/target combinations were used. The data of one of those pores is shown in FIGS. 9E and 9F. These data provide clear and direct evidence that ssDNA can thread through the M1MspA porin, confirming the hypothesis that the deep blockades observed in FIG. 5 are indeed caused by translocation of ssDNA through the M1MspA porin.

Example 5: The MspA Mutant M1MspA Porin and Linear, Homogeneous ssDNA

The interaction between the M1MspA porin and linear, homogeneous ssDNA 50-mers were also investigated. At 180 mV, the addition of ~8 μM dT50 into the cis compartment caused ~5 blockades per second (FIG. 10), a factor of ~20 increase over the blockade rate in the absence of dT$_{50}$ (SEQ ID NO:32). Most of these blockades were shorter than 30 μs, which is too brief to resolve internal structure or estimate the depth of the blockade. Experiments with dA$_{50}$ (SEQ ID NO:49) and dC$_{50}$ (SEQ ID NO:48) gave similar results. The short duration of the observed blockades suggests that translocation of these linear, homogeneous ssDNA 50-mers is typically shorter than 30 μs. The blockades are also consistent with brief excursions of the polymers into the vestibule that end with escape back into the cis compartment. Although both translocation and escape likely occur in experiments with linear ssDNA 50-mers, estimates of the relative frequency of the two processes were not possible.

Example 6: Blockade Characteristics of the MspA Mutant M2MspA Porin with and without Analyte To further examine the effect of charges in the MspA porin on its DNA analysis capabilities, three additional mutations to the M1MspA porin were made and replaced negatively-charged residues in the vestibule and around the entrance with positively charged residues (FIG. 1). The resulting mutant D90N/D91N/D93N/D118R/D134R/E139K (M2MspA) porin demonstrated expression levels (FIG. 4) and tunnel-forming activity similar to WTMspA (FIG. 2) porin.

Figures 10A, 10B, 10C:
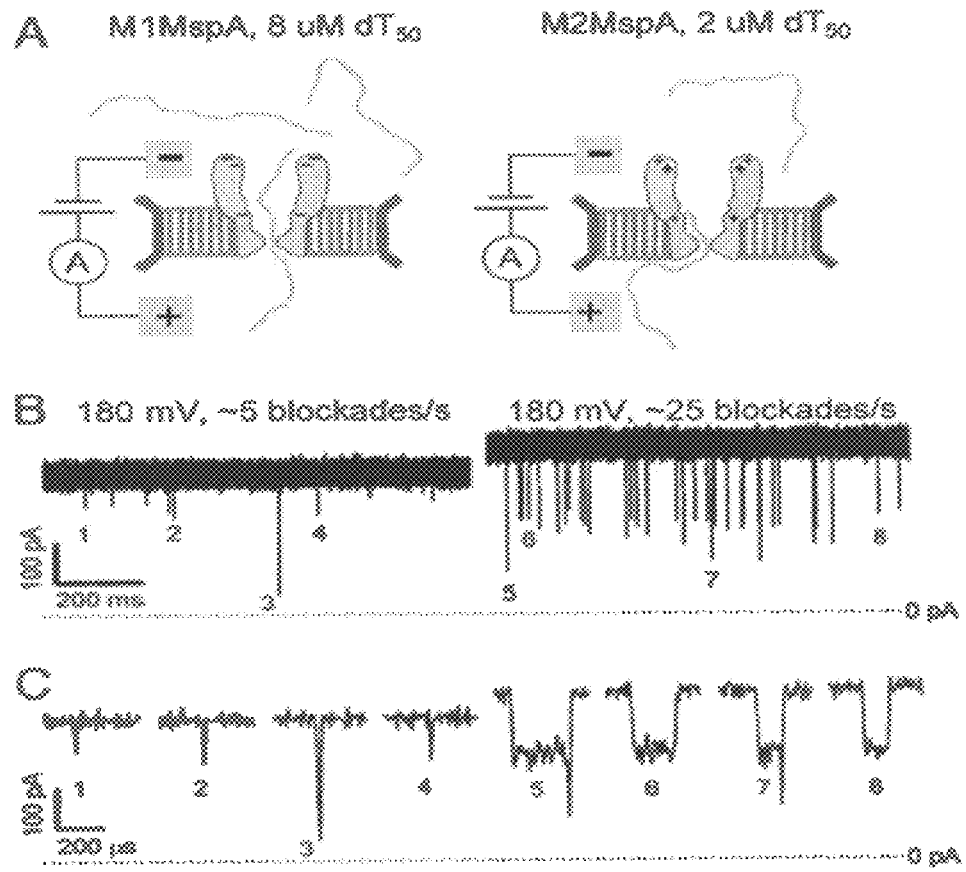
FIGS. 10A-10C compare $dT_{50}$ (SEQ ID NO:32) homopolymer blockades for M1MspA and M2MspA porins.
Figure 11:
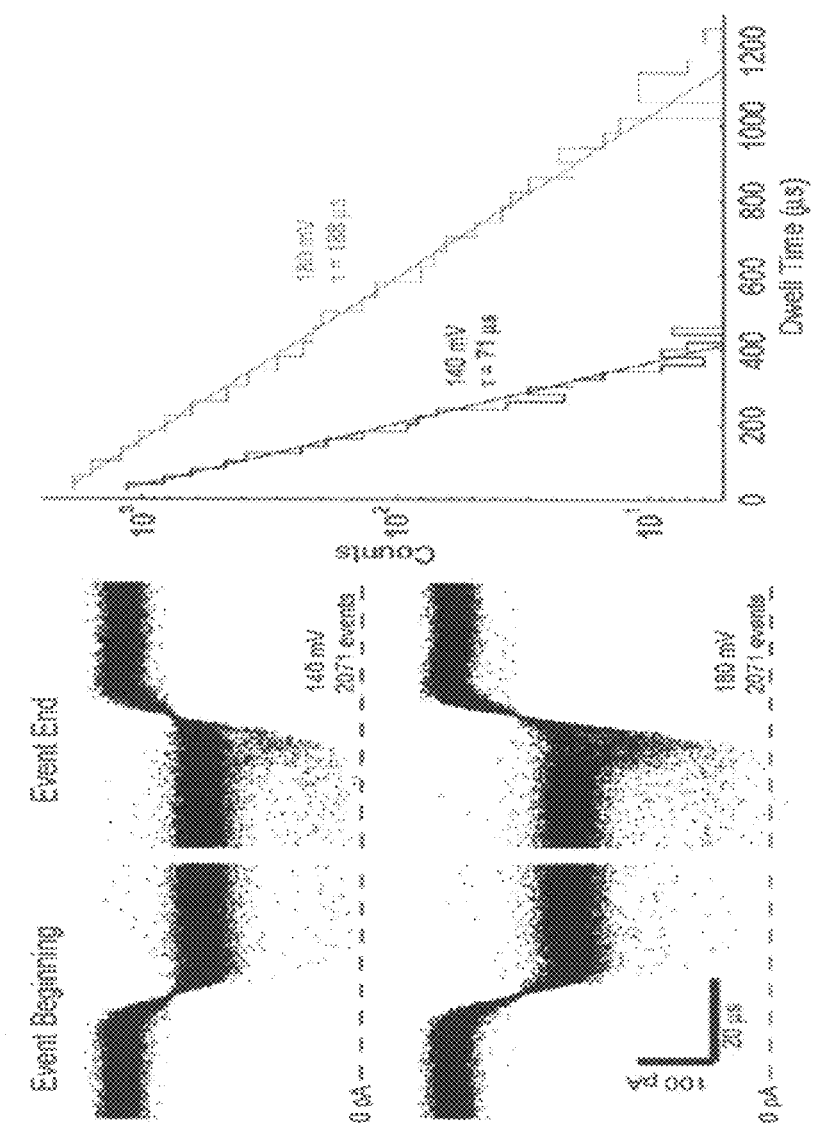
FIG. 11 shows statistical characteristics of $dT_{50}$ (SEQ ID NO:32) blockades in the M2MspA porin. Comparison of the average structure at the beginning and end of the blockades. The figure was created by overlaying the events in a data file aligned at the beginning of the event (Left) and at the end of the event (Right). Shown is the tendency of blockades to terminate with a brief downward deflection of the ionic current, along with the increase in this tendency with voltage.

Like the M1MspA porin, the M2MspA porin had smaller conductance than the WTMspA porin (FIG. 2) and exhibited minimal spontaneous blockades for voltages up to and above 180 mV. At 180 mV, the addition of 2 µM $dT_{50}$ (SEQ ID NO:32) to the cis compartment led to blockade rates of ~25 blockades per second (FIG. 10B). A ~100 µs partial blockade ending with a clear downward spike was a common blockade pattern (FIG. 10C). The partial blockade durations and their tendency to end with a downward spike both increased with voltage (FIG. 11). These trends are consistent with a process where a polymer enters the vestibule and is held there, producing a partial blockade until one end enters the high-field constriction and initiates translocation. This mechanism has accurately explained a similar partial-to-deep blockade pattern observed with αHL (Butler et al., *Biophys. J.* 93:3229 (2007)). The short duration of the downward spikes suggests that translocation of linear ssDNA 50-mers through the M2MspA porin is shorter than ~30 µs. Partial blockades that do not end with downward spikes are interpreted as either escape back into the cis compartment or as translocation that is shorter than ~10 µs, which is too brief to be observed in these experiments.

Example 7: Comparison of the M1 and M2 MspA Mutant Porins and αHL Properties An important similarity between the M1MspA and M2MspA porins is that translocation of linear ssDNA 50mers appears to be too fast to produce deep blockades with resolvable structure. Without being bound by theory, this observation suggests that the constriction, which is the same for both mutants, is the region which primarily determines the speed of a linear ssDNA molecule translocating through the MspA porin. Comparing the ~2-10 base/µs MspA translocation speeds of the M1MspA and M2MspA porins to the ~0.5-1 base/µs translocation speeds observed with αHL (Meller et al., *Proc. Natl Acad. Sci. USA* 97:1079 (2000); Butler et al., *Biophys. J.* 93:3229 (2007)) supports the notion that the details of the tunnel geometry and composition play a leading role in determining translocation speed.

In the case of the MspA porin and αHL, the large difference in translocation speed could result from the width of the tunnel regions flanking the constrictions. If interaction between DNA and the tunnel walls slows DNA passage (Slonkina and Kolomeisky, *J. Chem. Phys.* 118:7112-8 (2003)), then slower translocation would be expected in αHL where the 10-20 bases that are highly confined in the constriction and transmembrane region are forced to interact with the tunnel walls. In the MspA porin, only the 2-4 bases in the constriction are forced to be in contact with the protein. The charge distribution within the constriction is another significant difference between αHL and the M1 and M2 MspA mutant porins. The αHL constriction is formed by the side chains of E111, K147, and M113 (Song et al., *Science* 274:1859 (1996)), forcing the negatively charged ssDNA backbone into extremely close proximity with seven positively-charged and seven negatively-charged residues. The lack of charged residues in the constriction of the M1 and M2 MspA mutant porins could also be responsible for the faster translocation speeds compared with αHL.

Further comparison of the homopolymer blockade characteristics between the two MspA mutant porins gives insight into how the arrangement of charged residues in the tunnel influences its interactions with DNA. Blockade rates for the M2MspA porin were ~20 times higher than the M1MspA porin rates for a given ssDNA concentration (FIG. 10B). The M2MspA porin also demonstrated easily observable blockades down to ~80 mV, whereas almost no blockades were visible for the M1MspA porin below ~140 mV. Finally, partial blockades for the M2MspA porin were at least ~100 times longer than for the M1MspA porin (FIG. 9C). These trends are consistent with a simple electrostatic model wherein the positively-charged residues in the M2MspA porin both facilitate ssDNA entry into the vestibule and inhibit the escape of ssDNA molecules from the vestibule back into the cis compartment. These observations demonstrate that the appropriate placement of charged residues offers a simple means to substantially tailor the interaction between the MspA porin and DNA.

Example 8: The M1MspA Porin Recognizes a Single Nucleotide in a DNA Held in the Pore by a Hairpin (hp) Section Experiments with the M1MspA porin and (i) a poly-A DNA strand with a single C embedded within and (ii) a single T embedded in a poly-A background) proceeded as described in Example 3. As noted above, the hairpin holds the DNA construct in the MspA porin constriction zone for long enough to obtain very well defined current signatures.

Figure 12A:
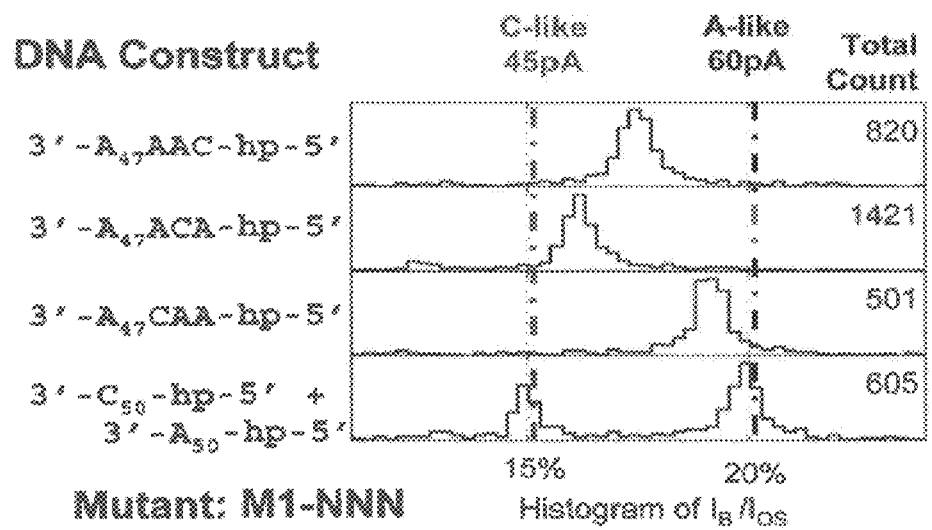
FIG. 12A shows histograms of blockade current levels in the M1MspA porin blocked by DNA constructs. The DNA constructs from top to bottom: 3'-$A_{47}$AAC-hp-5' (SEQ ID NO:14); 3'-$A_{47}$ACA-hp-5' (SEQ ID NO:33); 3'-$A_{47}$CAA-hp-5' (SEQ ID NO:13); 3'-$C_{50}$-hp-5' (SEQ ID NO:16); 3'-$A_{50}$-hp-5' (SEQ ID NO:10).
Figure 12B:
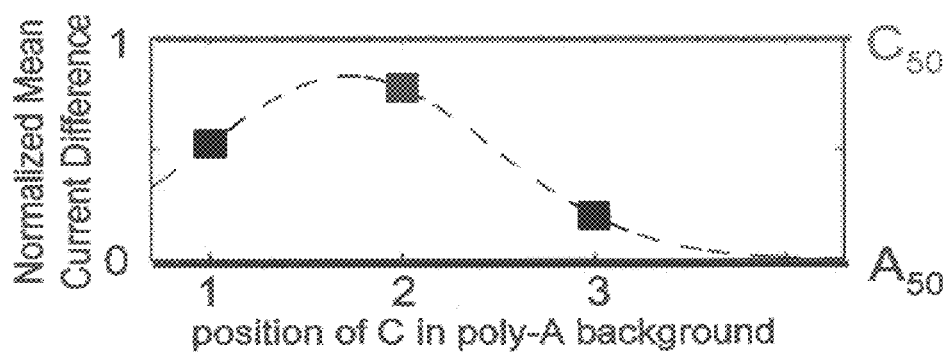
FIG. 12B shows a plot of the current levels scaled to the difference between poly-C (=1.0) and poly-A (=0.0) levels versus position of the single C. A Gaussian fit suggests that the recognition position for a single C is 1.7±0.8 nucleotides (nt) away from the end of the hairpin.

A single C embedded in a poly-A DNA hairpin construct. FIG. 12A displays the current histogram due to a single C at position 1, 2, and 3 following the hairpin as well as a mixture of poly-A and poly-C. The current histograms for each site are very distinct and show that the "recognition site" is near position 2. For a more quantitative description, the peak of the current distributions was scaled by the current difference found for poly-C and poly-A (FIG. 12B). A Gaussian fit reveals that the MspA porin's recognition position for a single C is 1.7 nucleotides (nt) away from where the hairpin rests. The length of the recognition site (constriction zone length) is comparable to the width of the Gaussian (1.6 nt) ~5-6 Å long.

Figure 13:
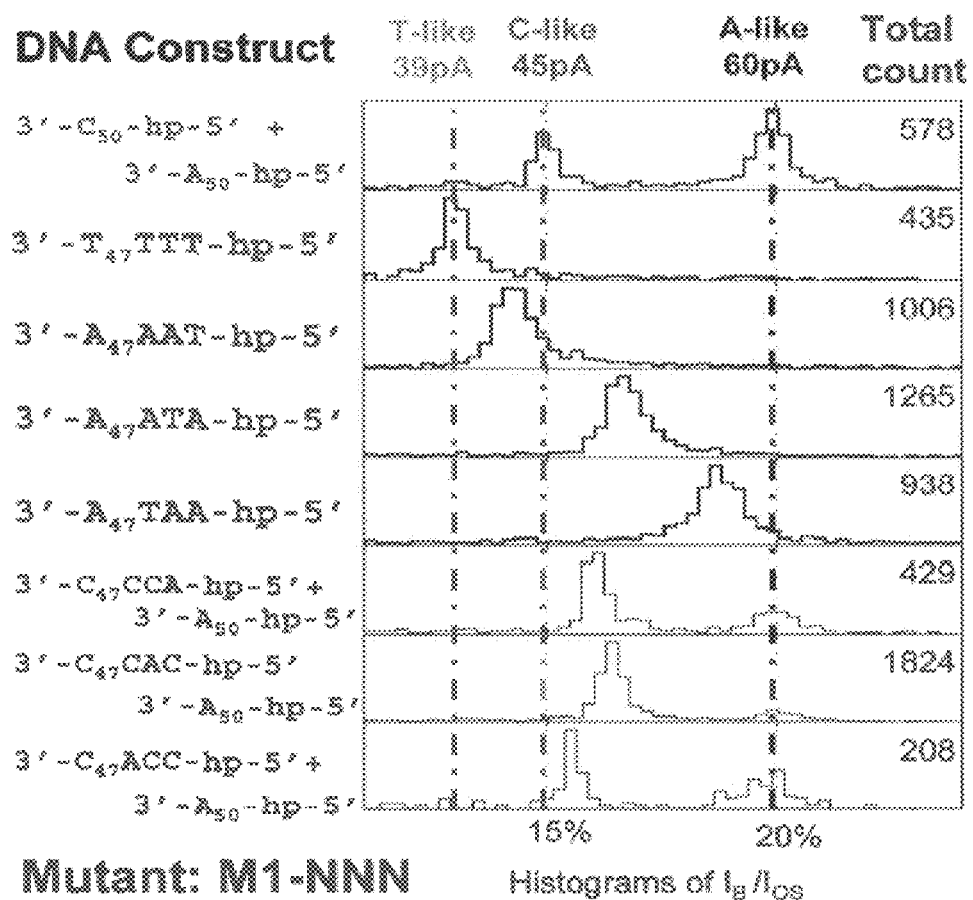
FIG. 13 shows a number of current histograms of DNA blocking the M1-NNN MspA (also called M1MspA) porin. The DNA constructs from top to bottom: 3'-$C_{50}$-hp-5' (SEQ ID NO:16); (SEQ ID NO:10); 3'-$T_{47}$TTT-hp-5' (SEQ ID NO:17); 3'-$A_{47}$AAT-hp-5' (SEQ ID NO:34); 3'-$A_{47}$ATA-hp-5' (SEQ ID NO:35); 3'-$A_{47}$TAA-hp-5' (SEQ ID NO:36); 3'-$C_{47}$CCA-hp-5' (SEQ ID NO:37); 3'-$C_{47}$CAC-hp-5' (SEQ ID NO:38); 3'-$C_{47}$ACC-hp-5' (SEQ ID NO:39). Each construct or mixture is shown at left. The numbers of events in each histogram are shown at right. Top panel: "Calibration mixture" (poly-A-hp and poly-C-hp). Panels 2-5: Poly-T-hp and single T bases in poly-A background. Bottom three panels: Single A bases in poly-A background. Poly-A-hp is included in the mixture for reference (small peak at 19.5%). All data are with 180 mV applied.

A single T embedded in a poly-A DNA hairpin construct. Experiments using a single T in poly-A DNA were conducted in a similar fashion, focusing only on the first three positions adjacent to the hairpin (FIG. 13, panels 2-4). The specificity is equally impressive but in this case exhibits the largest sensitivity near position 1. The location of the single T can be resolved to much better than one position. Without being bound by theory, the inventors speculate that the difference in the position recognition compared to a C in poly-A is in fact caused by the DNA itself contributing to the electrostatic environment forming the constriction. Data with a single A in a C background is shown in the lowest three panels of FIG. 13. While the single A produces current blockade signatures that are only weakly separated from the poly-C background, the current distributions are narrow enough to resolve the single A. The optimum position of A in the poly-C chain appears to be near position 2, i.e. similar to a single C in an A chain.

Figure 14:
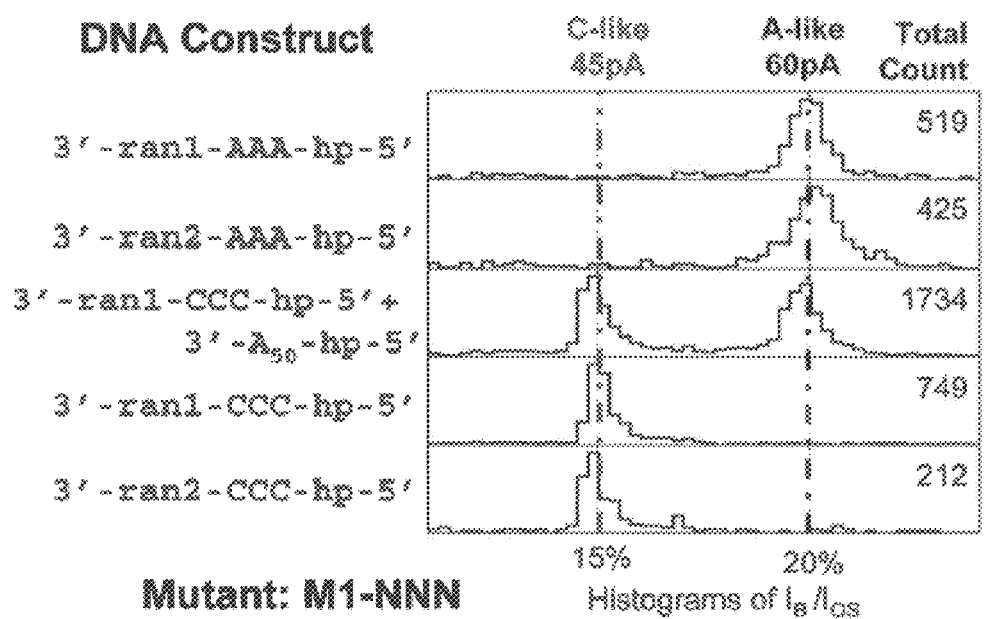
FIG. 14 demonstrates that the DNA tail does not affect recognition properties. Legend is as for FIG. 13. Two heterogeneous tails ('ran1' (SEQ ID NO:51), 'ran2' (SEQ ID NO:52), each 47 bases) are attached to tri-nucleotides and the hairpin. The middle panel shows the current histogram resulting when a mixture of $A_{50}$-hp DNA (SEQ ID NO:10) and ran1-$C_3$-hp DNA is applied to the pore, a reference point for the other panels. The current levels are identical to those of $A_{50}$ or $C_{50}$ tails. All data are with 180 mV applied.

The composition of the DNA tail beyond position 3 does not affect the base recognition properties. Poly-A DNA forms secondary structure, and the differences between the C-in-poly-A background and A-in-poly-C background data could be due to the interruption of the secondary structure (stiffness) of the poly-A tail. Measurements were conducted with a 47 base-long heterogeneous sequence following the first three positions occupied by A or C tri-nucleotides. Current levels were found to be indistinguishable from pure $A_{50}$ and $C_{50}$ tail current levels, indicating that the tails secondary structure or composition does not affect the current blockade (FIG. 14).

Another series of experiments were conducted (1) to assess the ability of the M1MspA porin to distinguish different nucleotides and (2) to evaluate the location and length of the region to which porin is sensitive (spatial resolution). In these experiments, various DNA constructs with a 50 nucleotide strand of ssDNA attached to a 14 base pair hairpin section to prevent immediate translocation were used. The data are summarized in FIG. 31. $dA_{50}$ (SEQ ID NO:49) and $dC_{50}$ (SEQ ID NO:48) produced significantly different blockade currents. Next, a series of constructs were tested, and the recognition site was isolated to within the first four bases following the hairpin. These constructs had ssDNA sequences of $dC_4dA_{46}$ (SEQ ID NO:15), $dA_3dC_4dA_{43}$ (SEQ ID NO:12), and $dA_6dC_4dA_{40}$ (SEQ ID NO:11) following the hairpin. $dC_4dA_{46}$ displays a blockade current distribution nearly identical to $dC_{50}$, while $dA_3dC_4dA_{43}$ and $dA_6dC_4dA_{40}$ block like $dA_{50}$. This narrowed the recognition site to be with the first 3 nucleotide following the hairpin. Next, the constructs were tested with a single dC at various positions in a poly-dA background. Hp-$dC_1dA_{49}$ (dC at position 1) (SEQ ID NO:14) blocked the current at a level intermediate between the poly-dA and poly-dC values. The construct $dA_2dC_3dA_{47}$ (dC at position 3) (SEQ ID NO:50) blocked the current intermediate between poly-dA and poly-dC, but closed to poly-dA. Poly-$dT_{50}$ (SEQ ID NO:32) blocked with the smallest current, and hp-$dG_3dA_{47}$ (SEQ ID NO:18) yields a current intermediate between poly-dC and poly-dA. In a different mutant (D90/91Q+D93N+D118/134R+E139K), the blockade currents for poly-dC, poly-dA, and poly-dT were measured and were distinguishable from each other. These data demonstrate that the M1MspA porin has recognition capabilities and that the recognition site is short. Furthermore, the recognition site appears to be located at the constriction zone, assuming the hairpin is arrested right at the cis side of the constriction zone.

Example 9: Construction and Characterization of Mutant MspA M1-QQN and M2-QQN Porins In another set of experiments designed to slow DNA translocation through the MspA porin tunnel, two additional mutants were made. One, called M1-QQN, was made in a similar fashion as M1-NNN (or M1MspA) above by replacing the amino acids in positions 90 and 91 of the wild-type MspA monomer with glutamine and the amino acid in position 90 with asparagine. With M2-QQN, the pore constriction size was reduced by introducing the bulkier glutamine at positions 90 and 91 in the background of the M2MspA mutant (see Example 6; D90Q+D91Q+D93N+ D118R+E139K+D134R). It was expressed in the *M. smegmatis* ML16 mutant described in Examples 1 and 3 above.

Figures 15A, 15B:
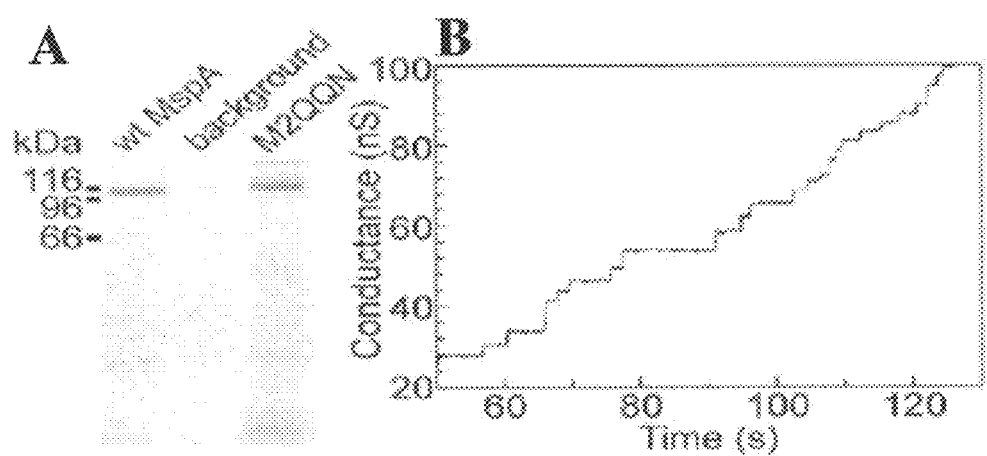
FIGS. 15A and 15B show characterization data of the M2-QQN porin, another mutant MspA porin.

The amount of the M2-QQN porin in detergent extracts was as high as that of the WTMspA porin (FIG. 15A) indicating that the new mutations did not affect pore expression. Lipid bilayer experiments showed that the M2-QQN porin forms stable open pores as the WTMspA porin (FIG. 15B). The pore forming activity is similar to that of the WTMspA porin. The M2-QQN porin's single-tunnel conductance (2.4 nS) was higher than that of its parent M2 (1.4 nS).

Figure 16:
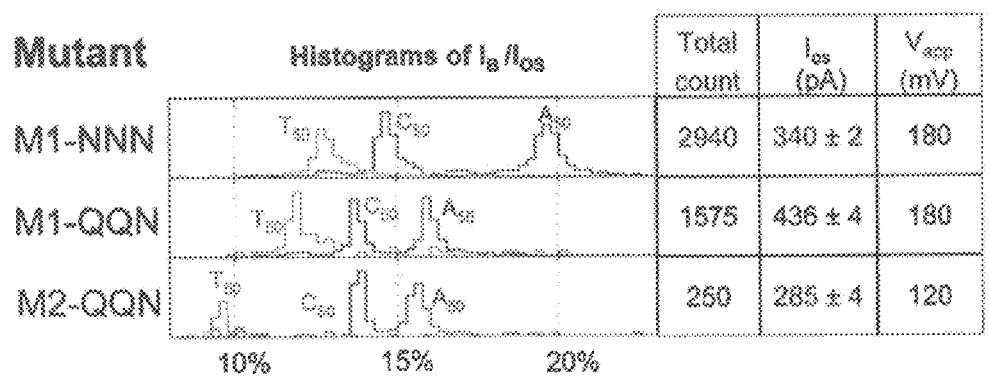
FIG. 16 shows blockade current histograms with three different mutant MspA porins exposed to hairpin DNA mixtures of hp-$T_{50}$ (SEQ ID NO:17), hp-$C_{50}$ (SEQ ID NO:16), and hp-$A_{50}$ (SEQ ID NO:10). In each case currents are normalized to the open state current, shown at right for each mutant. hp-$C_{50}$ and hp-$A_{50}$ were run as a mixture, and $T_{50}$ was run separately.

QQN mutants also distinguish between A, C, and T bases. Qualitatively similar to the M1MspA mutant porins (also called M1-NNN mutants), the QQN mutants exhibit well-resolved current levels using homopolymer-hp strands but the relative spacings between the levels are different in the M1-QQN porin. For each pore, data was collected with hairpin DNA with $A_{50}$, $T_{50}$ and $C_{50}$ tails (SEQ ID NO:49, SEQ ID NO:32, SEQ ID NO:48, respectively). The blockage currents were plotted as a fraction of the unblocked, open pore current (FIG. 16). In each case poly-T blocks more than poly-C, and poly-C blocks more than poly-A. Each peak is well resolved from the others. In the QQN porin, mean poly-A and poly-C current levels are less separated than in the M1-NNN porin, but poly-T is more separated from poly-C than in the M1-NNN porin. Surprisingly, the relative level of poly-T blockage in the two QQN mutant porins is distinctly different. These two mutants differ only in rim domain substitutions far from the constriction. Without being bound by theory, this may be due to interactions between the rim domain and the anchoring hairpin.

Figure 17:
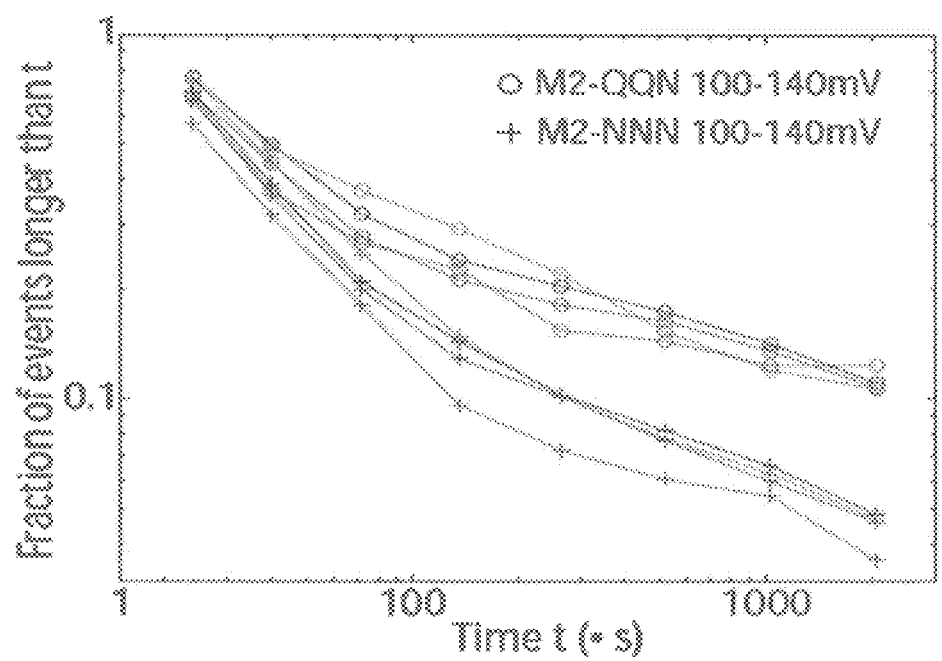
FIG. 17 is a graph showing the survival probability of deep current blockades of two mutant MspA porins. Shown is the probability of events lasting longer than t. Circles indicate the M2-QQN porin, and crosses indicate the M2-NNN porin. Voltages applied across the bilayers were 100, 120, and 140 mV. Data are normalized to the total number of events in each record.

The QQN mutant porins appear to slow DNA translocation through MspA. The primary motivation to construct the QQN mutants was to slow the DNA passage. The translocation of a heterogeneous 100 nt ssDNA segment (with no anchoring hairpin) was recorded along with the duration of deep blockade states. The survival plot (FIG. 17) shows the fraction of blockage events that last longer than time t. During the first ~100 μs the NNN mutant decays significantly faster than for the mutants with the QQN constriction zone. These data are consistent with an increased barrier to translocation through QQN.

Example 10: Construction of an *M. smegmatis* Quadruple Msp Deletion Mutant

For preparation of the MspA porin, protein from the mutant strain *M. smegmatis* ML16, which contains only one (MspB) of the four Msp genes (the others are MspA, MspC, and MspD) was selectively extracted. The procedure exploits the extreme thermal stability of MspA by boiling *M. smegmatis* cells in 0.5% n-octylpolyoxyethylene (OPOE), a non-ionic detergent, and yields the MspA porin with very little contamination by other proteins (Heinz and Niederweis, *Anal. Biochem.* 285:113-20 (2000)). However, background expression of MspB is still detectable in immunoblots using an Msp-specific antiserum (Stephan et al., *Mol. Microbiol.* 58:714-30 (2005)), indicating that mixed MspA/MspB oligomers could form and contribute to the pore heterogeneity observed in pore reconstitution experiments. Therefore, one of the goals was to construct an *M. smegmatis* strain free of endogenous porins. Since *M. smegmatis* requires porin activity for survival, a loxP-flanked MspA expression cassette was integrated into the chromosomal attB site for the mycobacteriophage L5 of the porin triple mutant ML16.

Figure 19:
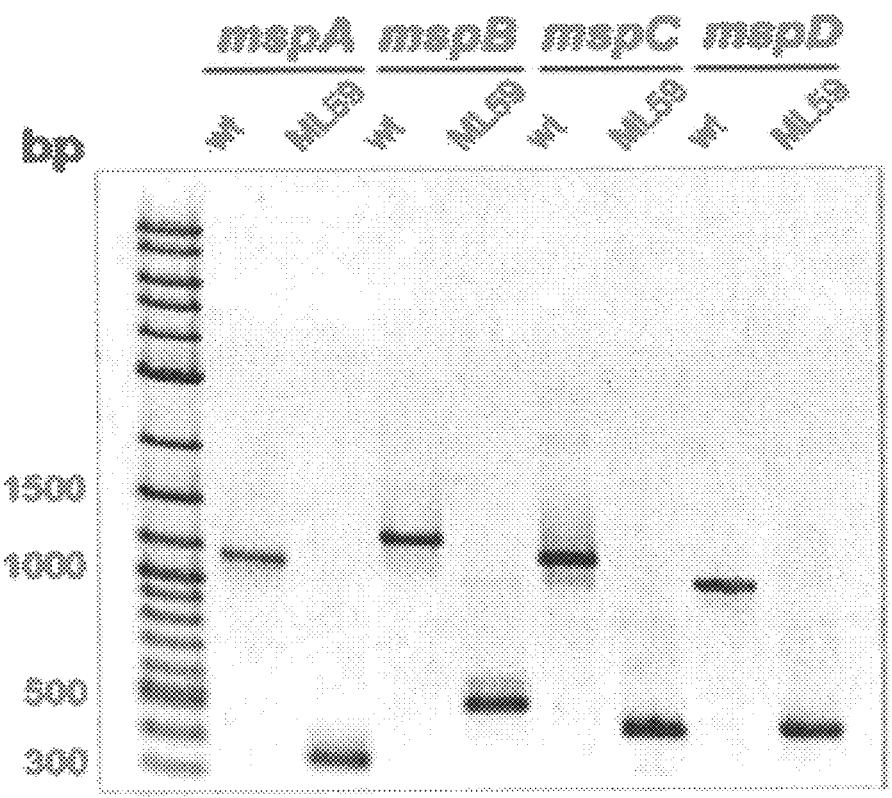
FIG. 19 is an image of a gel showing deletion of each of the porin genes in the M. smegmatis porin-quadruple mutant ML59.
Figure 20:
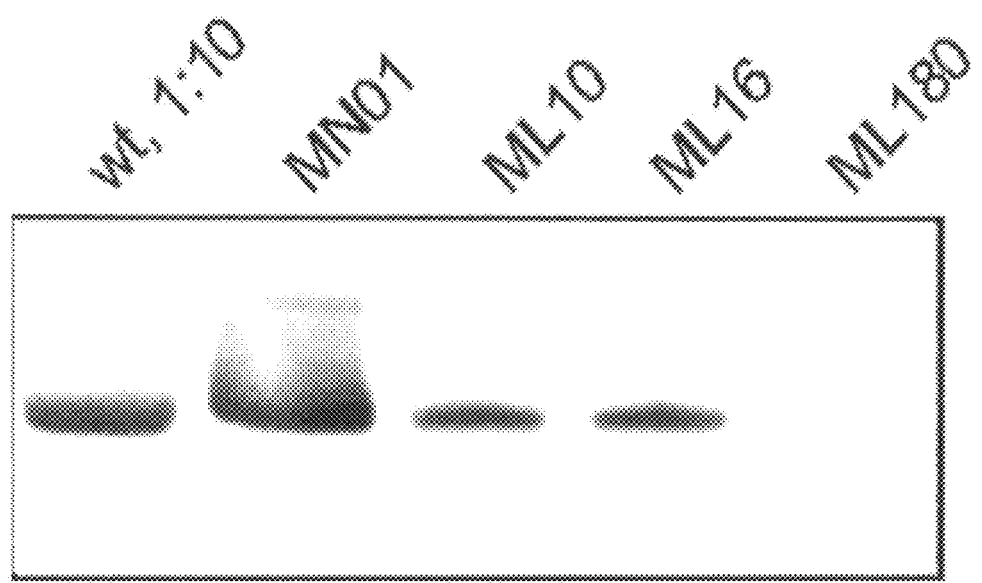
FIG. 20 shows a Western blot demonstrating Msp porin expression in M. smegmatis and M. smegmatis porin mutants. Lane 1 is a 1:10 dilution of protein extract for the wild-type M. smegmatis, lane 2 is mutant MN01 (ΔmspA), lane 3 is mutant ML10 (ΔmspAC), lane 4 is mutant ML16 (ΔmspACD), and lane 5 is mutant ML180 (ΔmspABCD).

This restored MspA monomer expression in the strain ML56 to half of the wild-type level. Then, the MspB gene was replaced by a FRT-flanked hyg gene using the suicide vector pMN247 in a two-step strategy as described (Stephan et al., *Gene* 343:181-190 (2004)). After excision of the hyg gene by the Flp recombinase, the porin quadruple mutant strain ML59 (ΔMspA ΔMspB ΔMspC ΔMspD attB::loxP-MspA-loxP) was obtained. The deletion of the MspB gene was confirmed by Southern blot hybridization. PCR demonstrated the absence of each of the four original Msp genes (FIG. 19). Excision of the loxP-MspA-loxP cassette resulted in small, viable clones, one of which (ML180) was examined in more detail. Proteins were extracted from ML180 cells using the same high-temperature method and Western analysis demonstrated that ML180 cells did not express Msp porin proteins nor were there any reconstitution events in lipid bilayer experiments after addition of 20 µg protein (FIG. 20). Together these results demonstrate that an *M. smegmatis* porin mutant lacking all four Msp porins has been created. However, it was not possible to detect MspA monomer expression using MspA expression vectors, most likely because of unknown secondary mutations. Therefore, this *M. smegmatis* strain cannot be used for expression of MspA pores engineered for DNA translocation.

Example 11: Construction of *M. smegmatis* Quadruple Msp Deletion Mutant ML705

Utilizing Inducible Expression of MspA

For isolation of wild-type and mutant MspA porins, the *M. smegmatis* ML16 strain (ΔMspA, ΔMspC, ΔMspD) is currently used. However, background expression of MspB complicates the interpretation of translocation experiments. Therefore, construction of a *M. smegmatis* strain lacking all four Msp genes is needed to improve single-pore experiments. To do this, the MspA gene, under control of the acetamide-inducible promoter, was integrated into the L5 attB site of *M. smegmatis* ML16 resulting in the removal of the MspB gene by allelic exchange. Therefore, in the presence of acetamide, MspA was expressed to rescue growth of the *M. smegmatis* quadruple mutant.

Figure 21A:
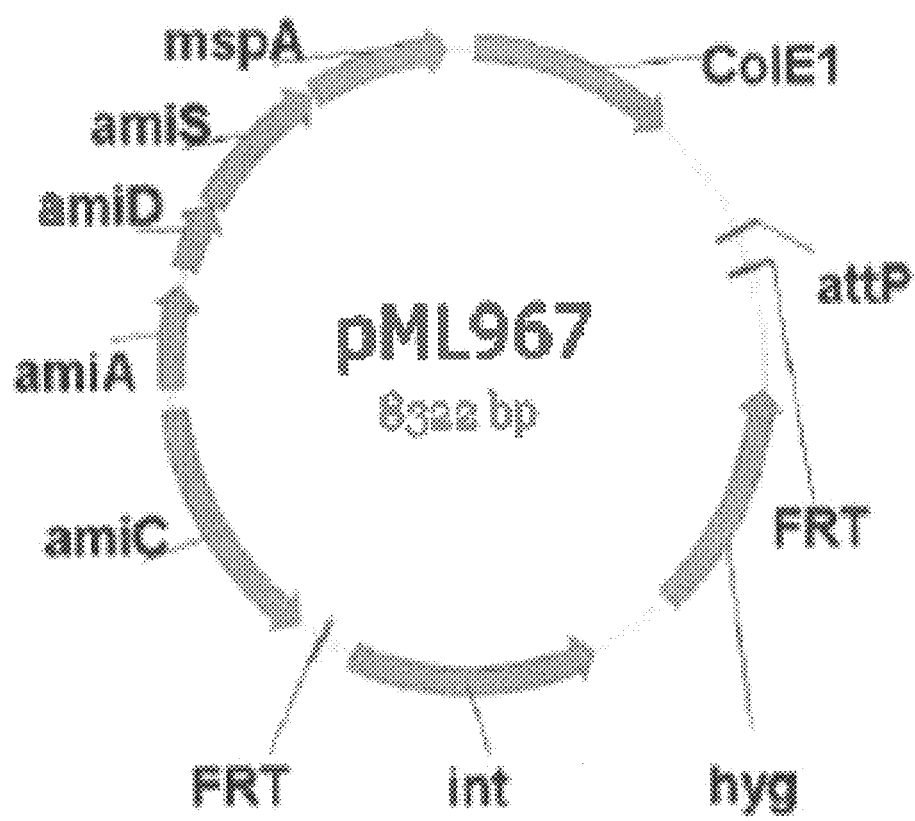
FIGS. 21A and 21B show plasmid maps for the construction of a quadruple porin mutant. Hyg: hydromycin resistance gene; ColE1: E. coli origin of replication.
Figure 21B:
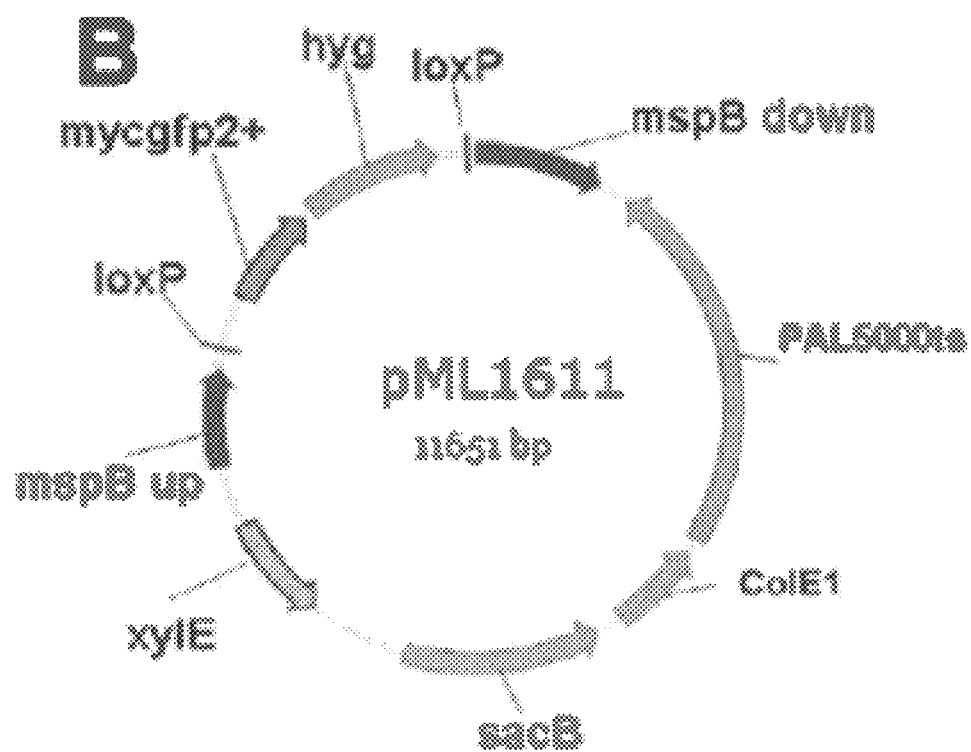

To achieve this, the integration plasmid pML967 was constructed, which contains the MspA gene under control of the acetamide-inducible promoter (FIG. 21A). The MspB deletion vector, pML1611 (FIG. 21B), was also constructed and contains the two reporter genes gfp and xylE as markers for integration and allelic replacement.

Figure 22:
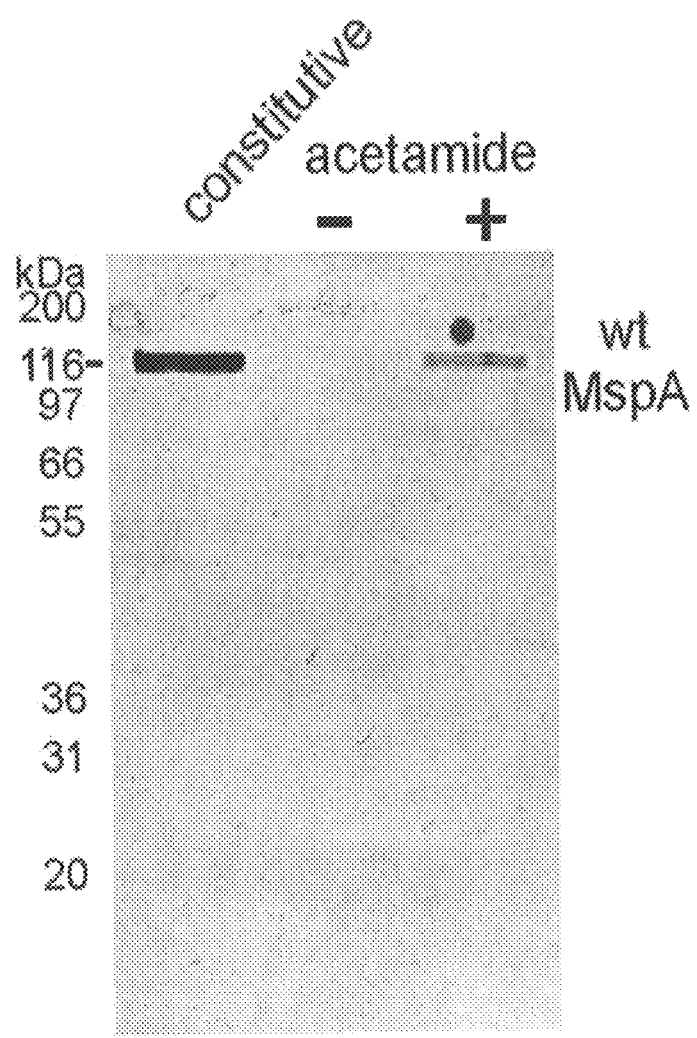
FIG. 22 is an image of a Coomassie blue stained gel showing the inducible expression of MspA monomers in *M. smegmatis*.

The strain ML341 (ML16, attP::pML967) was obtained after integration of the MspA monomer expression plasmid pML967 into *M. smegmatis* ML16. The hygromicin resistance gene was removed from this strain by a temporary expression of the Flp recombinase from the plasmid pML2005 as described previously (Song et al., Mycobacteria protocols (2008)) resulting in the strain ML343 (ML341, attP::p$_{acet}$-MspA). To examine the functionality of the integrated MspA gene monomer, MspA was extracted with a detergent from uninduced and induced cells. FIG. 22 shows that MspA is expressed at 20% of wild-type levels from the integrated construct after addition of 2% acetamide. This MspA monomer level is sufficient to enable the survival of *M. smegmatis*. There was little background expression of Msp porins in uninduced cells (FIG. 22) demonstrating that the expression system is regulated.

Then, the MspB deletion vector pML1611 was transformed into ML343. Transformants were plated on Middlebrook 7H10 agar plates containing 10% sucrose for direct selection of double cross-over candidates. Several colonies were obtained, which showed the presence of GFP by green fluorescence upon irradiation with blue light and the absence of XylE. Colony PCR from one of the clones confirmed the absence of the MspB gene and the construction of a viable Msp quadruple mutant. This strain was named ML378. The ML378 strain was transformed with the pCreSacB1 plasmid to remove the gfp-hyg expression cassette. Upon subsequent counter selection, several clones were obtained and examined by colony PCR. One of the eight unmarked porin quadruple mutants of *M. smegmatis* was named ML705 and further characterized.

Figure 24:
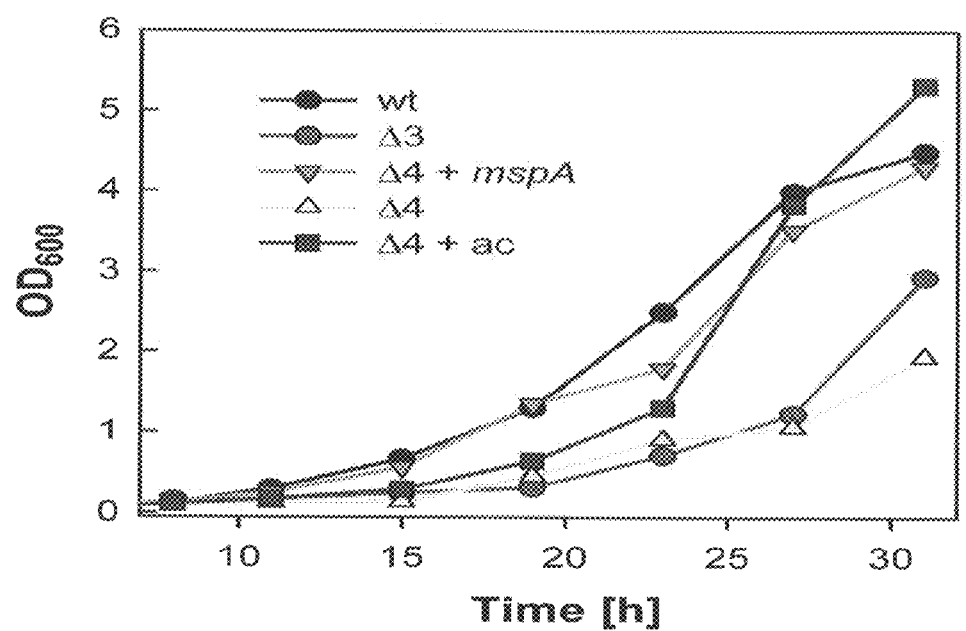
FIG. 24 is a graph showing the rate of growth of ML705 in rich liquid medium.

To examine whether MspA monomers complement the phenotype of the quadruple mutant, the MspA expression plasmid pMN016 was transformed into ML705. FIG. 24 shows the growth of ML705 on 7H10 agar plates was drastically reduced; however, expression of MspA from pMN016 completely restored growth of ML705 to wild-type levels (FIG. 23). These results demonstrated that no secondary mutations caused the growth defect and that MspA monomers can be expressed to produce MspA porins in the Msp quadruple mutant ML705.

Figure 25:
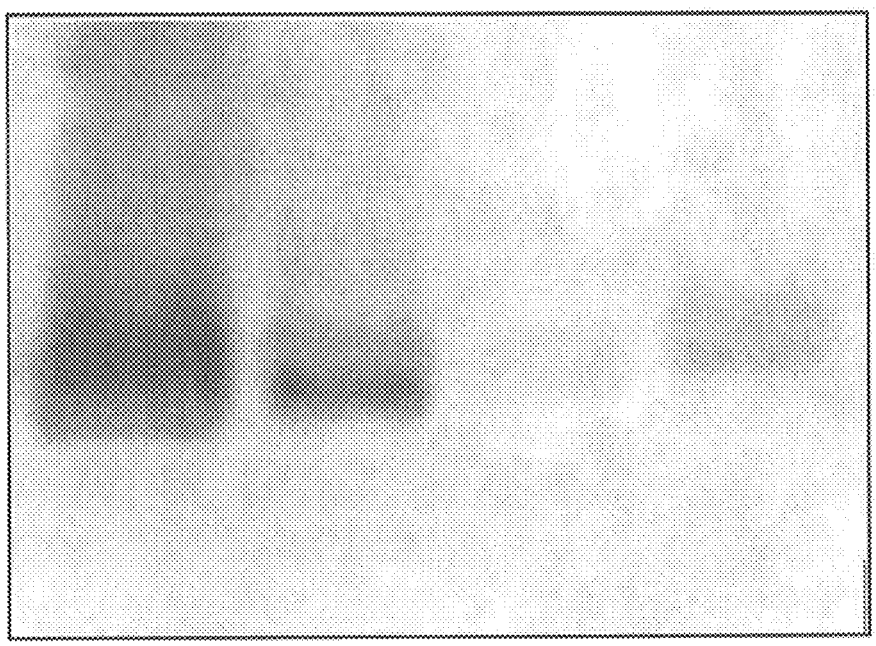
FIG. 25 is an image of a Western blot demonstrating expression of MspA monomers in the quadruple mutant ML705 upon induction with acetamide. Lane 1 is wild-type *M. smegmatis*, lane 2 is the quadruple mutant strain ML705 with acetamide, lane 3 is the quadruple msp mutant strain ML705 without acetamide, and lane 4 is the triple mutant strain ML16. Proteins were detected using a polyclonal antibody to MspA.

Growth of the porin quadruple mutant ML705 in Middlebrook 7H9 medium was much slower than that of wildtype *M. smegmatis* and significantly slower than that of the porin triple mutant ML16 (FIG. 24). Addition of 2% acetamide to induce expression of the MspA gene monomer at the L5 site and expression of MspA on the plasmid pMN016 restored the growth rate to wild-type levels (FIG. 24). Growth of ML705 both on plates and in liquid cultures was slower than that of the triple mutant indicating that ML705 had fewer porins in the outer membrane than the Msp triple mutant ML16. This assumption was confirmed in a Western blot (FIG. 25). The amount of the MspA monomer is less than 5% of that compared to wild-type (wt) *M. smegmatis*, and 50% less than that of the triple mutant. FIG. 25 also demonstrates that we can induce MspA up to 25% of wild-type when 2% acetamide is added.

The experiments described above demonstrate that an Msp quadruple mutant (M1705) has been constructed, which can be grown in the presence of acetamide to temporarily produce wild-type MspA monomers. The ML705 strain can then be transformed with a plasmid containing an expression cassette for a wild-type or mutant MspA monomers, or wild-type or mutant single-chain Msp porins. Wild-type MspA monomer production can be shut off by washing off and transferring cells to a medium without acetamide. This gives rise to the production of wild-type or mutant MspA monomers or wild-type of mutant single-chain Msp porins with less contamination by wild-type MspA. Thus, ML705 is suited for the production of wild-type and mutated MspA porins for all purposes.

Example 12: Construction of a Single-Chain MspA Porin Dimer

Figure 26A:
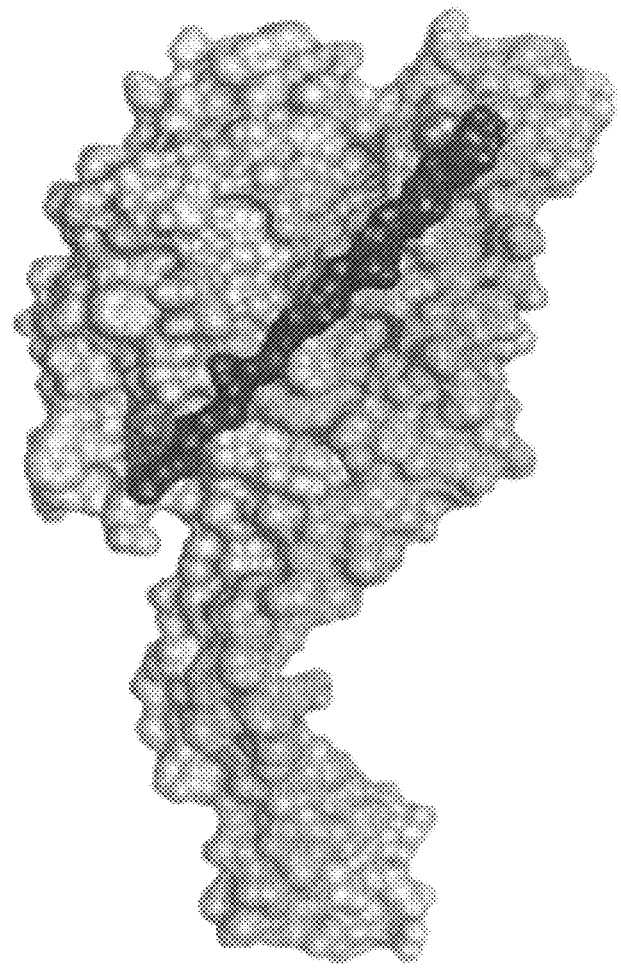
Figure 26D:
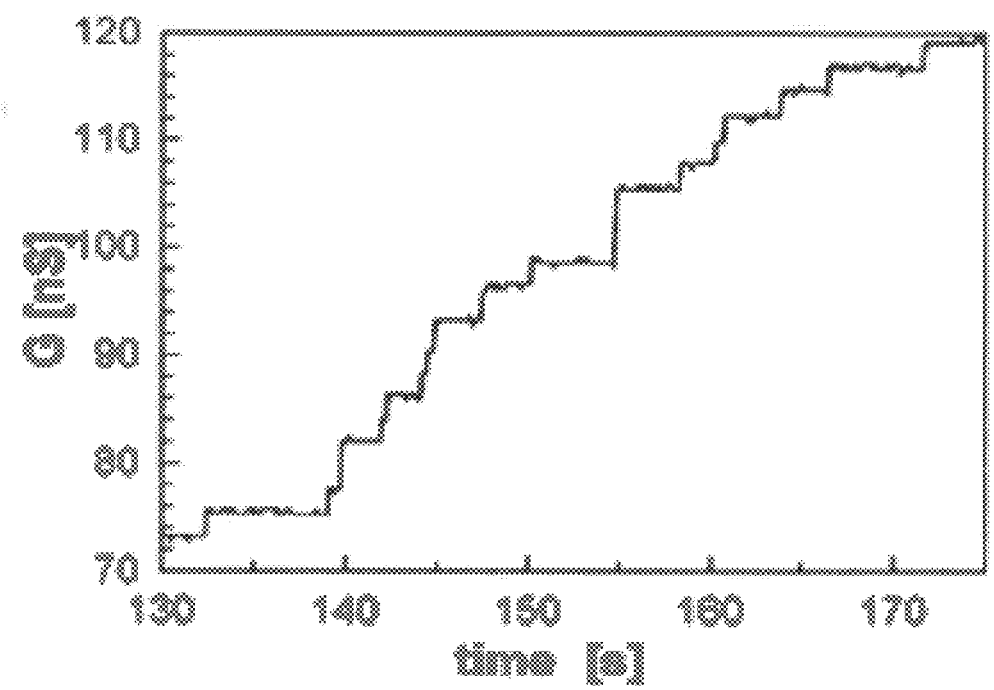
Figure 27:
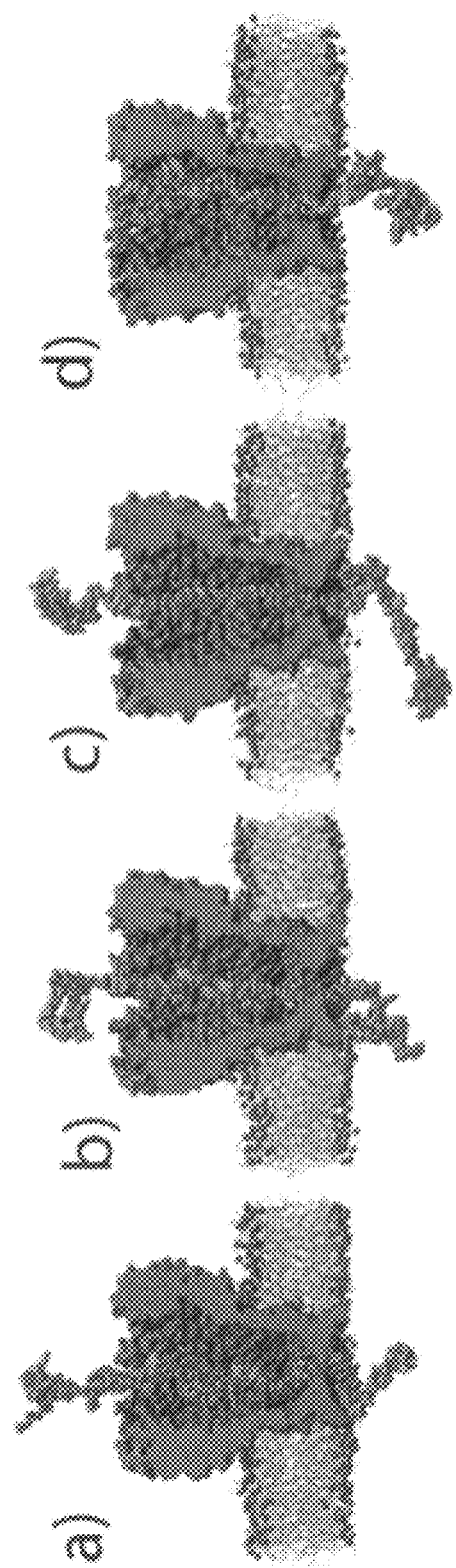
FIG. 27 shows a schematic of $dC_{58}$ (SEQ ID NO:40) ssDNA transport through the wild-type MspA porin. The DNA transport is composed of the following steps: a) beginning of the simulation; b) and c) DNA conformations before and after the rapid advancement; and d) DNA adheres to the surface of the MspA porin.
Figure 28:
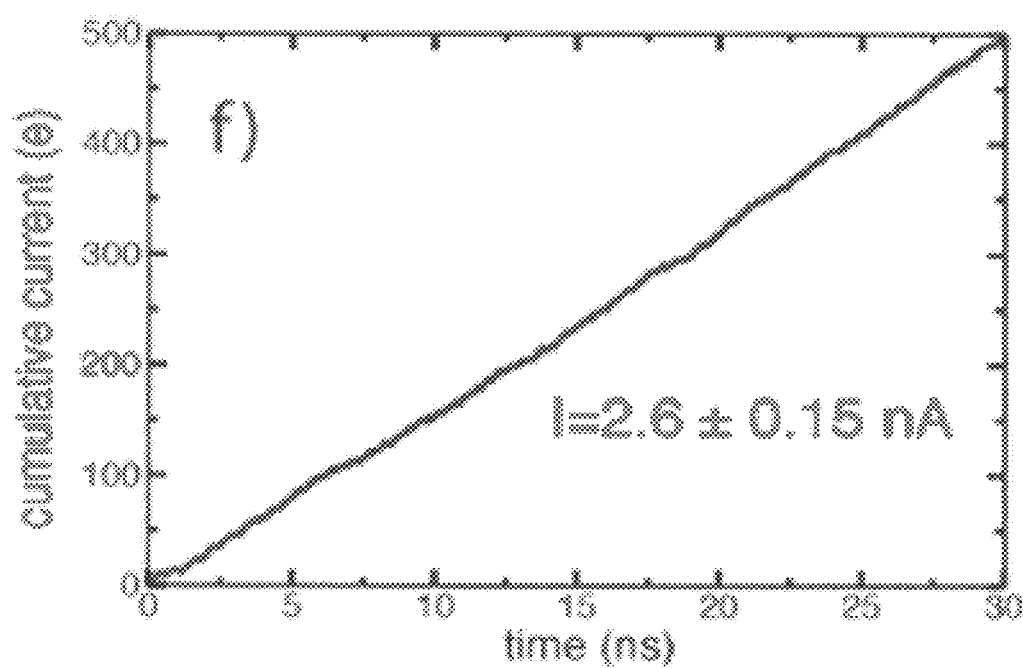
FIG. 28 is a graph showing the cumulative ionic current of the $dC_{58}$ (SEQ ID NO:40) ssDNA transport of FIG. 27. The transport was performed under a transmembrane bias of 1.2V.
Figure 29:
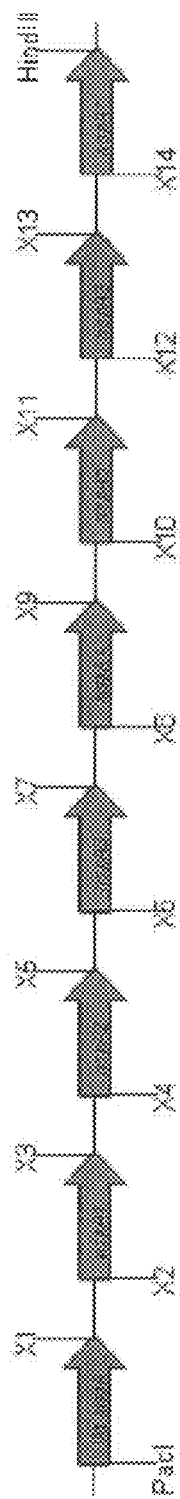
FIG. 29 shows the design of the single-chain MspA (scMspA) nanopore octamer sequence. The scMspA octamer consists of: a wild-type MspA gene monomer, a MspA1 monomer, a MspA2 monomer, a MspA3 monomer, a MspA4 monomer, a MspA5 monomer, a MspA6 monomer, and a MspA7 monomer. PadI and HindIII restriction sites flank the scMspA nanopore octamer sequence. X1-X14 are unique restriction sites flanking the individual monomeric sequences. Black lines connecting each monomer represent the $(GGGGS)_3$ (SEQ ID NO:3) linker.

Single-stranded DNA is not rotationally symmetric. Thus, it would be beneficial to have an asymmetric pore for sequencing purposes. To combine the superior sequencing capabilities of MspA porins with an increased ability to adapt vestibule and constriction properties to DNA sequencing, a single-chain MspA nanopore is to be constructed. The MspA chain termini are close together in the MspA porin dimer (FIG. 26A) and could be connected by a short peptide linker. To test this idea, the MspA gene monomer was fused together with the MspB gene monomer, which encodes for a protein with only two alterations (A138P, E139A) compared to the wild-type MspA monomer (Stahl et al., *Mol. Microbiol.* 40:451 (2001)). The (GGGGS)$_3$ (SEQ ID NO:3) peptide, often used to link proteins (Huston et al., *Proc. Natl. Acad. Sci. USA* 85:5879 (1988)), was used to connect the C-terminus of MspA monomer to the N-terminus of MspB monomer which lacks signal peptide (FIG. 26B). The resulting MspA-MspB porin dimer was placed under the control of the constitutive p$_{smyc}$ promoter in plasmid pML870 and was then expressed in *M. smegmatis* ML16. The protein was purified using the standard heat extraction procedure. Although the expression level of the single-chain MspA porin dimer was less than that of the wild-type MspA porin (FIG. 26C), the tunnel activity of both porins was similar (FIG. 26D). Analysis of the current recordings showed that the single tunnel conductance of the pore formed by the MspA dimer was 2.6 nS. This result shows that the linker segment does not impair Msp pore folding or function.

Example 13: Construction of a Single-Chain MspA Porin

To combine the superior sequencing capabilities of MspA with an increased ability to adapt vestibule and constriction properties to DNA sequencing, a single-chain MspA porin octamer is to be constructed that allows for the optimal properties of the vestibule and the constriction zone for DNA sequencing. The MspA chain termini are close together in the MspA porin and are connected by a short peptide linker. The (GGGGS)$_3$ (SEQ ID NO:3) peptide is used to connect the carboxy-terminus of the preceding MspA monomer to the amino-terminus of the following MspA monomer, which lacks signal peptide.

Figure 31:
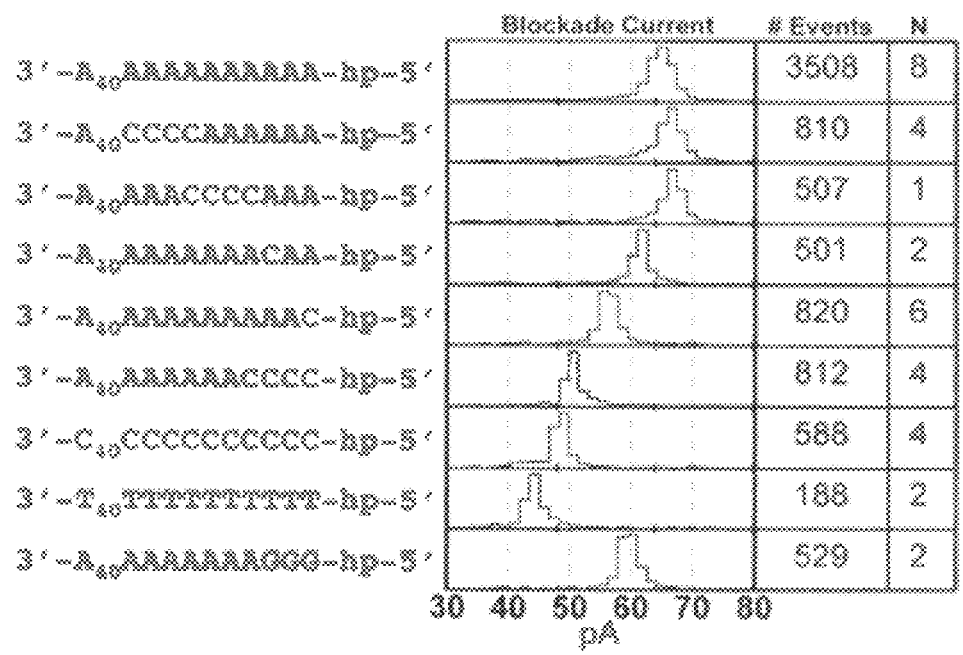
FIG. 31 shows histograms of blockade current levels in M1MspA blocked by DNA constructs. The DNA constructs from top to bottom: 3'-$A_{40}$AAAAAAAAAA-hp-5' (SEQ ID NO:10); 3'-$A_{40}$CCCCAAAAAA-hp-5' (SEQ ID NO:11); 3'-$A_{40}$AAACCCCAAA-hp-5' (SEQ ID NO:12); 3'-$A_{40}$AAAAAACAA-hp-5' (SEQ ID NO:13); 3'-$A_{40}$AAAAAAAAAC-hp-5' (SEQ ID NO:14); 3'-$A_{40}$AAAAAACCCC-hp-5' (SEQ ID NO:15); 3'-$C_{40}$CCCCCCCCCC-hp-5' (SEQ ID NO:16); 3'-$T_{40}$TTTTTTTTTT-hp-5' (SEQ ID NO:17); 3'-$A_{40}$AAAAAAGGG-hp-5' (SEQ ID NO:18).

To create a vector comprising the MspA porin sequence, each MspA monomer sequence is flanked by a unique restriction site, which allows the capability to mutate any individual monomer. The entire MspA porin sequence is flanked by PacI and HindIII restriction sites. Restriction sites between MspA monomer sequences comprise: BamHI, ClaI, EcoRV, HpaI, KpnI, MluI, NdeI, NheI, PstI, ScaI, SpeI, XbaI, NotI, and SphI (FIG. 31). To create the MspA porin sequence, each MspA sequence is assembled stepwise to form a dimeric, tetrameric, and octameric single-chain MspA utilizing the unique restriction sites. To avoid problems of recombination in creating the single-chain MspA multimer, seven MspA genes are synthesized with different codon usages (SEQ ID NO:21, SEQ ID NO:22, SEQ ID NO:23, SEQ ID NO:24, SEQ ID NO:25, SEQ ID NO:26, SEQ ID NO:27), i.e., the genes encode the exact same amino acid sequence, however, the DNA sequence has been altered from the native MspA gene nucleotide sequence (SEQ ID NO:20). To create the MspA porin sequence, the first Msp monomer must contain the leader sequence as shown in FIG. 18 (e.g., amino acids 1 to 27 of SEQ ID NO:28)). Each of the seven Msp monomer sequences following the first Msp monomer sequence can comprise SEQ ID NO:1 or a mutation of SEQ ID NO:1 chosen from any of the mutations listed in Table 7. The expression vector pML2604 is the parent vector comprising the MspA porin sequence cloned into the PacI and HindIII restriction sites. pML2604 is transformed into the quadruple porin mutant and expression levels and oligomeric status of the MspA porin are checked by Western blot of native and denatured proteins. The tunnel activity of the MspA porin is checked by lipid bilayer experiments.

TABLE 7

| MspA mutants | |
| --- | --- |
| Row 1 | Row 2 |
| MspA D90A | MspA T84C |
| MspA D91A | MspA I87C |
| MspA D90A/D91A | MspA D91C |
| MspA D90E | MspA D93C |
| MspA D91E | MspA A96C |
| MspA D90E/D91E | MspA P97C |
| MspA D90F | MspA G100C |
| MspA D91F | MspA N102C |
| MspA D90F/D91F | MspA P107C |
| MspA D90G | MspA G112C |
| MspA D91G | MspA V113C |
| MspA D90G/D91G | MspA S114C |
| MspA D90H | MspA D118C |
| MspA D91H | MspA N121C |

TABLE 7-continued

| MspA mutants | |
| --- | --- |
| Row 1 | Row 2 |
| MspA D90H/D91H | MspA E127C |
| MspA D90K | MspA F131C |
| MspA D91K | MspA D134C |
| MspA D90K/D91K | MspA S136C |
| MspA D90L | MspA A138C |
| MspA D91L | MspA E139C |
| MspA D90L/D91L | MspA G141C |
| MspA D90R | MspA V144C |
| MspA D91R | MspA H148C |
| MspA D90R/D91R | MspA T150C |
| MspA D90S | MspA A155C |
| MspA D91S | MspA R161C |
| MspA D90S/D91S | MspA R165C |
| MspA D90W | MspA S173C |
| MspA D91W | MspA T175C |
| MspA D90W/D91W | MspA E179C |
| MspA D90Y | MspA V184C |
| MspA D91Y | MspA N79C/D90K/D91N/P97C |
| MspA D90Y/D91Y | MspA K47S/D90K/D91N/P97C/D134C |
| MspA Q126C | MspA ΔA96-P98 |
| MspA D90N | MspA ΔT95-F99 |
| MspA D91N | MspA ΔI94-G100 |
| MspA D93N | MspA ΔD93-L101 |
| MspA D90N/D91N | MspA ΔG92-N102 |
| MspA D90N/D91N/D93N | MspA N79R/D90N/D91N/D93N |
| MspA D90Q/D91N/D93N | MspA N79W/D90N/D91N/D93N |
| MspA D90Q/D91Q/D93N | MspA D90N/D91N/D93N/Q126R |
| MspA D90T/D91N/D93N | MspA D90N/D91N/D93N/T130R |
| MspA D90T/D91T/D93N | MspA D90N/D91N/D93N/D134R |
| MspA D91E | MspA D90N/D91N/D93N/Q126W |
| MspA D90E | MspA D90N/D91N/D93N/T130W |
| MspA D90E/D91E | MspA D90N/D91N/D93N/D134W |
| MspA D90N/D91N/D93Q | MspA D90N/D91N/D93N/D118W/D134R/E139K |
| MspA D90N/D91N/G92Q/D93N | MspA D90N/D91N/D93N/D118F/D134R/E139K |
| MspA G1C | MspA D90N/D91N/D93N/D118H/D134R/E139K |
| MspA D3C | MspA D90N/D91N/D93N/D118Y/D134R/E139K |
| MspA E5C | MspA N79W/D90N/D91N/D93N/D118R/E139K |
| MspA D10C | MspA N79F/D90N/D91N/D93N/D118R/E139K |
| MspA D13C | MspA N79H/D90N/D91N/D93N/D118R/E139K |
| MspA R14C | MspA N79Y/D90N/D91N/D93N/D118R/E139K |
| MspA T17C | MspA D90N/D91K/D93N |
| MspA W21C | MspA D90N/D91R/D93N |
| MspA D22C | MspA D90N/D91W/D93N |
| MspA G27C | MspA D90N/D91W/D93N |
| MspA R33C | MspA D90N/D91T/D93N |
| MspA R38C | MspA D90N/D91L/D93N |
| MspA G44C | MspA D90N/D91H/D93N |
| MspA K47C | MspA D90N/D91S/D93N |
| MspA I49C | MspA D90N/D91N/D93N/D118R |
| MspA E57C | MspA D90N/D91N/D93N/D118R/E139R |
| MspA G60C | MspA D90N/D91N/D93N/D118R/E139K |
| MspA E63C | MspA D90N/D91N/D93N/D118R/D134R/E139K |
| MspA G69C | MspA D90Q/D91N/D93N/D118R/D134R/E139K |
| MspA S73C | MspA D90Q/D91Q/D93N/D118R/D134R/E139K |
| MspA L74C | MspA D90T/D91N/D93N/D118R/D134R/E139K |
| MspA V76C | MspA D90T/D91T/D93N/D118R/D134R/E139K |

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of detecting a nucleic acid, the method comprising:
   translocating a nucleic acid from a first conductive liquid medium to a second conductive liquid medium in liquid communication through a mutant *Mycobacterium smegmatis* porin A (MspA), wherein the mutant MspA comprises a mutant MspA monomer with at least one mutation with respect to SEQ ID NO:1, and wherein the mutant MspA has a neutral constriction zone;
   measuring an ion current between the first conductive liquid medium and the second conductive liquid medium, wherein a 5% or more reduction in the ion current for at least 1.0 µs compared to an ion current level for the mutant MspA without the nucleic acid indicates the presence of the nucleic acid in the first medium.

2. The method of claim 1, wherein the mutant MspA comprises a mutant MspA monomer, wherein the mutant MspA monomer comprises the following mutations of SEQ ID NO:1: D90N, D91N, and D93N.

3. The method of claim 1, wherein the mutant MspA comprises a mutant MspA monomer, wherein the mutant MspA monomer comprises the following mutations of SEQ ID NO:1: D90N, D91N, D93N, D118R, D134R, and E139K.

4. The method of claim 1, wherein the mutant MspA comprises a mutant MspA monomer, wherein the mutant MspA monomer comprises the following mutations of SEQ ID NO:1: D90N/Q/Y, D91N/Q/Y, and D93N/Q.

5. The method of claim 1, wherein the mutant MspA comprises a mutant MspA monomer, wherein the mutant MspA monomer comprises one or more of the following mutations of SEQ ID NO:1: L88W, I105W, N108W, D118R, D134R, A138P, and E139A/K.

6. The method of claim 1, wherein the mutant MspA comprises a mutant MspA monomer, wherein the mutant MspA monomer comprises one or more of the following mutations of SEQ ID NO:1: D90N/Q/Y, D91N/Q/Y, and D93N/Q.

7. The method of claim 1, wherein the mutant MspA comprises a mutant MspA monomer, wherein the mutant MspA monomer comprises one or more mutations at the following amino acid positions of SEQ ID NO:1: 88, 105, 108, 118, 134, or 139.

8. The method of claim 1, wherein translocating the nucleic acid from the first conductive liquid medium to the second conductive liquid medium in liquid communication through the mutant MspA comprises using a molecular motor to regulate a rate of translocation for the nucleic acid translocating through the mutant MspA.

9. The method of claim 8, wherein the molecular motor is a helicase.

10. The method of claim 8, wherein the molecular motor is a polymerase.

11. The method of claim 8, wherein the nucleic acid has an average translocation velocity through the mutant MspA of less than 1 nucleotide/µs.

12. The method of claim 1, wherein the mutant MspA comprises a mutant MspA monomer, wherein the mutant MspA monomer comprises a mutation of SEQ ID NO:1 at amino acid position 88.

13. The method of claim 1, wherein the mutant MspA comprises a mutant MspA monomer, wherein the mutant MspA monomer comprises a mutation of SEQ ID NO:1 at amino acid position 126.

14. The method of claim 1, wherein the mutant MspA comprises a first mutant MspA monomer comprising a mutant MspA monomer with at least one mutation with respect to SEQ ID NO:1 and a second mutant MspA monomer comprising a mutant MspA monomer with at least one mutation with respect to SEQ ID NO:1, wherein the first mutant MspA monomer has a different amino acid sequence than the second mutant MspA monomer.

15. The method of claim 1, wherein the mutant MspA comprises a first mutant MspA monomer comprising a mutant MspA monomer with at least one mutation with respect to SEQ ID NO:1 and a second mutant MspA monomer comprising a mutant MspA monomer with at least one mutation with respect to SEQ ID NO:1, wherein the first mutant MspA monomer is connected to the second mutant MspA monomer by one or more amino acid linkers.

\* \* \* \* \*

SEQUENCE LISTING

<160> NUMBER OF SEQ ID NOS: 94

<210> SEQ ID NO 1
<211> LENGTH: 184
<212> TYPE: PRT
<213> ORGANISM: Mycobacteria Smegmatis

<400> SEQUENCE: 1

Gly Leu Asp Asn Glu Leu Ser Leu Val Asp Gly Gln Asp Arg Thr Leu
 1               5                  10                  15

Thr Val Gln Gln Trp Asp Thr Phe Leu Asn Gly Val Phe Pro Leu Asp
             20                  25                  30

Arg Asn Arg Leu Thr Arg Glu Trp Phe His Ser Gly Arg Ala Lys Tyr
         35                  40                  45

Ile Val Ala Gly Pro Gly Ala Asp Glu Phe Glu Gly Thr Leu Glu Leu
     50                  55                  60

Gly Tyr Gln Ile Gly Phe Pro Trp Ser Leu Gly Val Gly Ile Asn Phe
 65                  70                  75                  80

Ser Tyr Thr Thr Pro Asn Ile Leu Ile Asp Asp Gly Asp Ile Thr Ala
                 85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Ala Glu Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 2
<211> LENGTH: 184
<212> TYPE: PRT
<213> ORGANISM: Mycobacteria Smegmatis

<400> SEQUENCE: 2

Gly Leu Asp Asn Glu Leu Ser Leu Val Asp Gly Gln Asp Arg Thr Leu
 1               5                  10                  15

Thr Val Gln Gln Trp Asp Thr Phe Leu Asn Gly Val Phe Pro Leu Asp
             20                  25                  30

Arg Asn Arg Leu Thr Arg Glu Trp Phe His Ser Gly Arg Ala Lys Tyr
         35                  40                  45

Ile Val Ala Gly Pro Gly Ala Asp Glu Phe Glu Gly Thr Leu Glu Leu
     50                  55                  60

Gly Tyr Gln Ile Gly Phe Pro Trp Ser Leu Gly Val Gly Ile Asn Phe
 65                  70                  75                  80

Ser Tyr Thr Thr Pro Asn Ile Leu Ile Asp Asp Gly Asp Ile Thr Ala
                 85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val

```
                130                 135                 140
Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 3
<211> LENGTH: 15
<212> TYPE: PRT
<213> ORGANISM: Artificial Sequence
<220> FEATURE:
<223> OTHER INFORMATION: Linker Peptide between MspA Peptides

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 72
<212> TYPE: DNA
<213> ORGANISM: Artificial Sequence
<220> FEATURE:
<223> OTHER INFORMATION: Oligonucleotides

<400> SEQUENCE: 4
gctgttgctc tctcgcaaca gcaaaaaaaa aaaaaaaaaa aaaaaaaaaa aaaaaaaaaa    60
aaaaaaaaaa aa                                                        72

<210> SEQ ID NO 5
<211> LENGTH: 76
<212> TYPE: DNA
<213> ORGANISM: Artificial Sequence
<220> FEATURE:
<223> OTHER INFORMATION: Oligonucleotides

<400> SEQUENCE: 5
gctctgttgc tctctcgcaa cagagcaaaa aaaaaaaaaa aaaaaaaaaa aaaaaaaaaa    60
aaaaaaaaaa aaaaaa                                                    76

<210> SEQ ID NO 6
<211> LENGTH: 80
<212> TYPE: DNA
<213> ORGANISM: Artificial Sequence
<220> FEATURE:
<223> OTHER INFORMATION: Oligonucleotides

<400> SEQUENCE: 6
gctgtctgtt gctctctcgc aacagacagc aaaaaaaaaa aaaaaaaaaa aaaaaaaaaa    60
aaaaaaaaaa aaaaaaaaaa                                                80

<210> SEQ ID NO 7
<211> LENGTH: 75
<212> TYPE: DNA
<213> ORGANISM: Artificial Sequence
<220> FEATURE:
<223> OTHER INFORMATION: Oligonucleotides

<400> SEQUENCE: 7 cccccaaaa aaaaaaaaaa aaaaaaaaaa aaaaaaaaaa aaaaaaaaaa aaaaaaaaaa    60
ctctattctt atctc                                                     75
```

<210> SEQ ID NO 8
<211> LENGTH: 75
<212> TYPE: DNA
<213> ORGANISM: Artificial Sequence
<220> FEATURE:
<223> OTHER INFORMATION: Oligonucleotides

<400> SEQUENCE: 8 cccccaaaa aaaaaaaaaa aaaaaaaaaa aaaaaaaaaa aaaaaaaaaa aaaaaaaaaa    60
cacacacaca cacac                                                    75

<210> SEQ ID NO 9
<211> LENGTH: 15
<212> TYPE: DNA
<213> ORGANISM: Artificial Sequence
<220> FEATURE:
<223> OTHER INFORMATION: Oligonucleotides

<400> SEQUENCE: 9
gagataagaa tagag                                                    15

<210> SEQ ID NO 10
<211> LENGTH: 50
<212> TYPE: DNA
<213> ORGANISM: Artificial Sequence
<220> FEATURE:
<223> OTHER INFORMATION: Oligonucleotides

<400> SEQUENCE: 10
aaaaaaaaaa aaaaaaaaaa aaaaaaaaaa aaaaaaaaaa aaaaaaaaaa              50

<210> SEQ ID NO 11
<211> LENGTH: 50
<212> TYPE: DNA
<213> ORGANISM: Artificial Sequence
<220> FEATURE:
<223> OTHER INFORMATION: Oligonucleotides

<400> SEQUENCE: 11
aaaaaacccc aaaaaaaaaa aaaaaaaaaa aaaaaaaaaa aaaaaaaaaa              50

<210> SEQ ID NO 12
<211> LENGTH: 50
<212> TYPE: DNA
<213> ORGANISM: Artificial Sequence
<220> FEATURE:
<223> OTHER INFORMATION: Oligonucleotides

<400> SEQUENCE: 12 aaacccaaa aaaaaaaaaa aaaaaaaaaa aaaaaaaaaa aaaaaaaaaa               50

<210> SEQ ID NO 13
<211> LENGTH: 50
<212> TYPE: DNA
<213> ORGANISM: Artificial Sequence
<220> FEATURE:
<223> OTHER INFORMATION: Oligonucleotides

<400> SEQUENCE: 13
aacaaaaaaa aaaaaaaaaa aaaaaaaaaa aaaaaaaaaa aaaaaaaaaa              50

<210> SEQ ID NO 14
<211> LENGTH: 50
<212> TYPE: DNA

```
<213> ORGANISM: Artificial Sequence
<220> FEATURE:
<223> OTHER INFORMATION: Oligonucleotides

<400> SEQUENCE: 14
caaaaaaaaa aaaaaaaaaa aaaaaaaaaa aaaaaaaaaa aaaaaaaaaa          50

<210> SEQ ID NO 15
<211> LENGTH: 50
<212> TYPE: DNA
<213> ORGANISM: Artificial Sequence
<220> FEATURE:
<223> OTHER INFORMATION: Oligonucleotides

<400> SEQUENCE: 15
ccccaaaaaa aaaaaaaaaa aaaaaaaaaa aaaaaaaaaa aaaaaaaaaa          50

<210> SEQ ID NO 16
<211> LENGTH: 50
<212> TYPE: DNA
<213> ORGANISM: Artificial Sequence
<220> FEATURE:
<223> OTHER INFORMATION: Oligonucleotides

<400> SEQUENCE: 16
cccccccccc cccccccccc cccccccccc cccccccccc cccccccccc          50

<210> SEQ ID NO 17
<211> LENGTH: 50
<212> TYPE: DNA
<213> ORGANISM: Artificial Sequence
<220> FEATURE:
<223> OTHER INFORMATION: Oligonucleotides

<400> SEQUENCE: 17
tttttttttt tttttttttt tttttttttt tttttttttt tttttttttt          50

<210> SEQ ID NO 18
<211> LENGTH: 50
<212> TYPE: DNA
<213> ORGANISM: Artificial Sequence
<220> FEATURE:
<223> OTHER INFORMATION: Oligonucleotides

<400> SEQUENCE: 18
gggaaaaaaa aaaaaaaaaa aaaaaaaaaa aaaaaaaaaa aaaaaaaaaa          50

<210> SEQ ID NO 19
<211> LENGTH: 45
<212> TYPE: DNA
<213> ORGANISM: Artificial Sequence
<220> FEATURE:
<223> OTHER INFORMATION: Oligonucleotides

<400> SEQUENCE: 19
ggcggtggcg gtagcggcgg tggcggtagc ggcggtggcg gtagc              45

<210> SEQ ID NO 20
<211> LENGTH: 549
<212> TYPE: DNA
<213> ORGANISM: Mycobacteria Smegmatis

<400> SEQUENCE: 20
ggcctggaca acgagctgag cctcgttgat ggccaggacc gcaccctcac cgtgcagcag    60
tgggacacct tcctcaatgg tgtgttcccc ctggaccgca accgtcttac ccgtgagtgg   120
```

```
ttccactccg gtcgcgccaa gtacatcgtg gccggccccg gtgccgacga gttcgagggc    180
acgctggaac tcggctacca gatcggcttc cgtggtcgc tgggtgtggg catcaacttc     240
agctacacca ccccgaacat cctgatcgac gacggtgaca tcaccgctcc gccgttcggc    300
ctgaactcgg tcatcacccc gaacctgttc ccggtgtgt cgatctcggc agatctgggc     360
aacggccccg gcatccagga agtcgcaacg ttctcggtcg acgtctccgg cgccgagggt    420
ggcgtggccg tgtcgaacgc ccacggcacc gtgaccggtg cggccggcgg tgtgctgctg    480
cgtccgttcg cccgcctgat cgcctcgacc ggtgactcgg tcaccaccta cggcgaaccc    540
tggaacatg                                                           549

<210> SEQ ID NO 21
<211> LENGTH: 549
<212> TYPE: DNA
<213> ORGANISM: Mycobacteria Smegmatis
<220> FEATURE:
<223> OTHER INFORMATION: Mutant MspA Gene

<400> SEQUENCE: 21
ggcctagaca atgagcttag ccttgttgac ggccaagacc gaaccctgac cctccagcaa     60
tgggatacct ttctcaacgg tgtattcccg ctggatcgca atcgtctaac ccgcgagtgg    120
ttccattccg gccgcgctaa gtatatcgta gccggacccg gggccgatga gtttgaggga    180
acgctcgaac ttggctatca gataggcttt ccgtggtcgc taggtgtcgg cattaacttt    240
agctatacca caccgaatat cctcatcgat gacggcgaca taaccgcgcc gcctttcggt    300
ctgaattcgg taatcacgcc gaatctgttt ccggggtgt ctatctcagc agacctgggg    360
aacggtcccg gaatccaaga agtggcaact ttctccgtcg atgtctcggg cgcggagggc    420
ggcgtagccg tctcgaatgc ccatggcacg gtgacaggtg cagccggggg tgtactgcta    480
cgtccattcg cgcgcctaat cgcgtcgaca ggtgattcgg ttaccacata cggtgaacca    540
tggaatatg                                                           549

<210> SEQ ID NO 22
<211> LENGTH: 549
<212> TYPE: DNA
<213> ORGANISM: Mycobacteria Smegmatis
<220> FEATURE:
<223> OTHER INFORMATION: Mutant MspA Gene

<400> SEQUENCE: 22
ggactggata acgaactgag tctggtagat gttcaggatc gcaatctcac agtgcaacag     60
tgggacactt tcctgaatgg cgtgtttccc ctcgaccgga accgacttac gcgtgaatgg    120
tttcactcag gtcgtgccaa atacattgtg gcgggcccgg gtgcggacga attcgaaggc    180
accctggagc tcgggtacca aatcggtttc ccttggtccc tgggcgtggg tatcaatttc    240
agttacacga cccccaacat tctgatagac gatggtgata tcacggctcc cccgtttggc    300
ctcaactccg tcataacccc caacctcttc cctggtgtct cgatttcggc cgatctcggc    360
aatggccctg gcattcagga ggtcgctacg ttttcggtgg acgtgtccgg tgccgaaggt    420
ggtgtggcgg tgtccaacgc gcacggtacc gtcaccggcg cggcgggcgg cgtgctcctg    480
cggccgtttg cccggctgat tgcctccacc ggggactccg tcacgaccta tggcgagccc    540
tggaacatg                                                           549

<210> SEQ ID NO 23
```

```
<211> LENGTH: 549
<212> TYPE: DNA
<213> ORGANISM: Mycobacteria Smegmatis
<220> FEATURE:
<223> OTHER INFORMATION: Mutant MspA Gene

<400> SEQUENCE: 23
ggccttgaca acgagctaag cctagttgac ggccaggacc gtaccctaac cctacagcag      60
tgggatacct ttctcaatag cgtcttccca ctggaccgca atcgtctgac ccgagagtgg     120
ttccactccg ggcgcgcaaa gtatatcgtc gccggtcccg gtgccgacga gttcgagttc     180
acgcttgaac taggctacca gattggcttc ccgtggtcgc ttggtgttgg cataaacttc     240
agctacacca ctccgaacat cctaatcgac gacggggaca ttaccgcacc gccattcggg     300
ctgaactcgg tgatcacacc gaacctgttt cccggagtgt caatctccgc agatcagggt     360
aacggacccg ggatccagga agttgcaacc ttctcagtcg acgtctcagg cgcagagggg     420
ggcgtcgccg tatcgaacgc ccacggcact gtgacgggtg ccgccggtgg tgtcctgctc     480
cgtcccttcg cacgcctcat cgcatcgacg ggtgactcgg taaccacgta cggggaaccg     540
tggaacatg                                                             549

<210> SEQ ID NO 24
<211> LENGTH: 549
<212> TYPE: DNA
<213> ORGANISM: Mycobacteria Smegmatis
<220> FEATURE:
<223> OTHER INFORMATION: Mutant MspA Gene

<400> SEQUENCE: 24
gggctggata acgaactgag tctcctggat ggacaggatc gcaatctcac ggtgcagcag      60
tgggacacat tccttaatgg ggtgttcccc cttgaccgta accggcttac acgtgaatgg     120
ttccactcgg gtcgggccaa gtacatagtg gctggccctg gtgctgacga gttcgaaggc     180
acactggaac tcggttacca aatcgggttc ccctggtcac tggggggtggg aatcaacttc     240
agctacacaa cccctaacat actgatagac gacggtgaca tcactgctcc tccgtttggc     300
cttaactcag tcattacccc taacctattc cccggtgttt cgatatcggc ggatcttggc     360
aacggcccgg gcatacagga agtcgcgacg ttctcggttg acgtttccgg ggccgagggt     420
ggggtggcag tgtcaaacgc tcacgggacc gttaccgggg cggcaggcgg ggtgcttctg     480
cgcccgttcg cccgtctgat agcctcaacc ggcgactcag tcacaaccta cggcgagccc     540
tggaacatg                                                             549

<210> SEQ ID NO 25
<211> LENGTH: 549
<212> TYPE: DNA
<213> ORGANISM: Mycobacteria Smegmatis
<220> FEATURE:
<223> OTHER INFORMATION: Mutant MspA Gene

<400> SEQUENCE: 25
ggactcgata atgaactcag tctagtagac ggtcaagatc ggaatctgac agtccaacaa      60
tgggatactt ttctgaacgg cgtctttccg ctcgatcgga atcgactcac gcgcgaatgg     120
tttcattcag ggcgtgcgaa atatattgtc gcggggccgg gcgcggatga atttgaaggt     180
accctcgagc tggggtatca aattggtttt ccttggtccc ttggcgtcgg tattaatttt     240
agttatcgca cgcccaatat tctccatagat gatggcgata taacggcgcc cccatttggg     300
ctcaattccg tgataacgcc caatctcttt cctggcgtct ccatttccgc cgacctcggt     360
```

```
aatggtcctg gtattcaaga ggtggctacc ttttccgtgg atgtgtcggg tgcggaaggc    420
ggtgtagcgg tatccaatgc gcatggtaca gtcacaggcg ccgcgggtgg cgtcctcctc    480
cggccatttg cacggctaat tgcgtccacg ggggattccg tgacgacgta tggtcagccg    540
tggaacatg                                                            549

<210> SEQ ID NO 26
<211> LENGTH: 549
<212> TYPE: DNA
<213> ORGANISM: Mycobacteria Smegmatis
<220> FEATURE:
<223> OTHER INFORMATION: Mutant MspA Gene

<400> SEQUENCE: 26
gggctagata atcagcttag tcttgtggac gggcaagatc gaacgctgac gctccaacaa     60
tgggatacgt ttctaaacgg cgtatttccg ctcgatcgga atcgactaac gcgcgaatgg    120
tttcattcgg gccgagctaa atatatagta gcaggaccgg gggcagatga atttgaagga    180
acactcgagc ttgggtatca aataggtttt ccttggtccc taggagtcgg gattaatttt    240
agttatacaa cacccaatat actcattgat gatggcgata taacggcgcc tccttttggt    300
ctcaattccg taattacgcc taatctcttt ccggggtgt ctatatcagc cgacctcggg    360
aacggtccag gaattcaaga ggtggcgact ttttccgtgg atgtttcggg agcggaaggc    420
ggtgtagcag cgtccaatgc tcatggaacg gtcacaggcg cagcaacagg agtactccca    480
cggccatttg cgcggctaat tgcgtctaca ggcgattccg ttacgacata tggtgagcca    540
tggaatatg                                                            549

<210> SEQ ID NO 27
<211> LENGTH: 549
<212> TYPE: DNA
<213> ORGANISM: Mycobacteria Smegmatis
<220> FEATURE:
<223> OTHER INFORMATION: Mutant MspA Gene

<400> SEQUENCE: 27
ggacttgata acgaactaag tctggtagat ggtcaggatc gtaatcttac agttcaacag     60
tgggacactt tcctgaatgg cgttttttcct ctcgaccgga accgactgac gcgggaatgg    120
tttcactcag gccgtgcaaa atacaatgta gcgggtccgg gagcggacga attcgaaggg    180
accctagagc ttgggtacca aatgggtttc ccttggtccc tcggcgtagg tataaatttc    240
agttacacga cacccaacat tcttatagac gatggggata ttacggcacc ccccttggt    300 ctcaactccg taataacacc caacctcttc cctggagtct ctatttcagc cgatctcgga    360
aatggacctg gaattcagga ggttgctaca ttttctgtgg acgtgtcagg tgcagaagga    420
ggtgtcgcgg tctccaacgc gcacggtacg gtcacgggcg ctgcggggg cgttctcctt    480 cggccctttg cgcggctcat tgcttccaca ggggactccg taacgactta tggacagcct    540
tggaatatg                                                            549

<210> SEQ ID NO 28
<211> LENGTH: 211
<212> TYPE: PRT
<213> ORGANISM: Mycobacteria Smegmatis
<220> FEATURE:
<223> OTHER INFORMATION: MspA Protein

<400> SEQUENCE: 28
```

```
Met Lys Ala Ile Ser Arg Val Leu Ile Ala Met Val Ala Ala Ile Ala
1               5                   10                  15
Ala Leu Phe Thr Ser Thr Gly Thr Ser His Ala Gly Leu Asp Asn Glu
            20                  25                  30
Leu Ser Leu Val Asp Gly Gln Asp Arg Thr Leu Thr Val Gln Gln Trp
        35                  40                  45
Asp Thr Phe Leu Asn Gly Val Phe Pro Leu Asp Arg Asn Arg Leu Thr
    50                  55                  60
Arg Glu Trp Phe His Ser Gly Arg Ala Lys Tyr Ile Val Ala Gly Pro
65                  70                  75                  80
Gly Ala Asp Glu Phe Glu Gly Thr Leu Glu Leu Gly Tyr Gln Ile Gly
                85                  90                  95
Phe Pro Trp Ser Leu Gly Val Gly Ile Asn Phe Ser Tyr Thr Thr Pro
            100                 105                 110
Asn Ile Leu Ile Asp Asp Gly Asp Ile Thr Ala Pro Pro Phe Gly Leu
        115                 120                 125
Asn Ser Val Ile Thr Pro Asn Leu Phe Pro Gly Val Ser Ile Ser Ala
    130                 135                 140
Asp Leu Gly Asn Gly Pro Gly Ile Gln Glu Val Ala Thr Phe Ser Val
145                 150                 155                 160
Asp Val Ser Gly Ala Glu Gly Val Ala Val Ser Asn Ala His Gly Thr
                165                 170                 175
Thr Val Thr Gly Ala Ala Gly Val Leu Leu Arg Pro Phe Ala Arg
            180                 185                 190
Leu Ile Ala Ser Thr Gly Asp Ser Val Thr Thr Tyr Gly Glu Pro Trp
        195                 200                 205
Asn Met Asn
    210

<210> SEQ ID NO 29
<211> LENGTH: 215
<212> TYPE: PRT
<213> ORGANISM: Mycobacteria Smegmatis
<220> FEATURE:
<223> OTHER INFORMATION: MspB Protein

<400> SEQUENCE: 29

Met Thr Ala Phe Lys Arg Val Leu Ile Ala Met Ile Ser Ala Leu Leu
1               5                   10                  15
Ala Gly Thr Thr Gly Met Phe Val Ser Ala Gly Ala His Ala Gly
            20                  25                  30
Leu Asp Asn Glu Leu Ser Leu Val Asp Gly Gln Asp Arg Thr Leu Thr
        35                  40                  45
Val Gln Gln Trp Asp Thr Phe Leu Asn Gly Val Phe Pro Leu Asp Arg
    50                  55                  60
Asn Arg Leu Thr Arg Glu Trp Phe His Ser Gly Arg Ala Lys Tyr Ile
65                  70                  75                  80
Val Ala Gly Pro Gly Ala Asp Glu Phe Glu Gly Thr Leu Glu Leu Gly
                85                  90                  95
Tyr Gln Ile Gly Phe Pro Trp Ser Leu Gly Val Gly Ile Asn Phe Ser
            100                 105                 110
Tyr Thr Thr Pro Asn Ile Leu Ile Asp Asp Gly Asp Ile Thr Ala Pro
        115                 120                 125
Pro Phe Gly Leu Asn Ser Val Ile Thr Pro Asn Leu Phe Pro Gly Val
    130                 135                 140
```

```
Ser Ile Ser Ala Asp Leu Gly Asn Gly Pro Gly Ile Gln Glu Val Ala
145                 150                 155                 160

Thr Phe Ser Val Asp Val Ser Gly Pro Ala Gly Gly Val Ala Val Ser
                165                 170                 175

Asn Ala His Gly Thr Val Thr Gly Ala Ala Gly Gly Val Leu Leu Arg
                180                 185                 190

Pro Phe Ala Arg Leu Ile Ala Ser Thr Gly Asp Ser Val Thr Thr Tyr
                195                 200                 205

Gly Glu Pro Trp Asn Met Asn
        210                 215

<210> SEQ ID NO 30
<211> LENGTH: 215
<212> TYPE: PRT
<213> ORGANISM: Mycobacteria Smegmatis
<220> FEATURE:
<223> OTHER INFORMATION: MspC Protein

<400> SEQUENCE: 30

Met Lys Ala Ile Ser Arg Val Leu Ile Ala Met Ile Ser Ala Leu Ala
1               5                   10                  15

Ala Ala Val Ala Gly Leu Phe Val Ser Ala Gly Thr Ser His Ala Gly
                20                  25                  30

Leu Asp Asn Glu Leu Ser Leu Val Asp Gly Gln Asp Arg Thr Leu Thr
            35                  40                  45

Val Gln Gln Trp Asp Thr Phe Leu Asn Gly Val Phe Pro Leu Asp Arg
    50                  55                  60

Asn Arg Leu Thr Arg Glu Trp Phe His Ser Arg Ala Lys Tyr Ile
65                  70                  75                  80

Val Ala Gly Pro Gly Ala Asp Glu Phe Glu Gly Thr Leu Glu Leu Gly
                85                  90                  95

Tyr Gln Ile Gly Phe Pro Trp Ser Leu Gly Val Gly Ile Asn Phe Ser
                100                 105                 110

Tyr Thr Thr Pro Asn Ile Leu Ile Asp Asp Gly Asp Ile Thr Gly Pro
                115                 120                 125

Pro Phe Gly Leu Glu Ser Val Ile Thr Pro Asn Leu Phe Pro Gly Val
                130                 135                 140

Ser Ile Ser Ala Asp Leu Gly Asn Gly Pro Gly Ile Gln Glu Val Ala
145                 150                 155                 160

Thr Phe Ser Val Asp Val Ser Gly Pro Ala Gly Gly Val Ala Val Ser
                165                 170                 175

Asn Ala His Gly Thr Val Thr Gly Ala Ala Gly Gly Val Leu Leu Arg
                180                 185                 190

Pro Phe Ala Arg Leu Ile Ala Ser Thr Gly Asp Ser Val Thr Thr Tyr
                195                 200                 205

Gly Glu Pro Trp Asn Met Asn
        210                 215

<210> SEQ ID NO 31
<211> LENGTH: 207
<212> TYPE: PRT
<213> ORGANISM: Mycobacteria Smegmatis
<220> FEATURE:
<223> OTHER INFORMATION: MspD Protein

<400> SEQUENCE: 31

Met Arg Tyr Leu Val Met Met Phe Ala Leu Leu Val Ser Val Thr Leu
1               5                   10                  15
```

```
Val Ser Pro Arg Pro Ala Asn Ala Val Asp Asn Gln Leu Ser Val Val
         20                  25                  30

Asp Gly Gln Gly Arg Thr Leu Thr Val Gln Gln Ala Glu Thr Phe Leu
         35                  40                  45

Asn Gly Val Phe Pro Leu Asp Arg Asn Arg Leu Thr Arg Glu Trp Phe
 50                  55                  60

His Ser Arg Ala Thr Tyr His Val Ala Gly Pro Gly Ala Asp Glu
 65                  70                  75                  80

Phe Glu Gly Thr Leu Glu Leu Gly Tyr Gln Val Gly Phe Pro Trp Ser
                 85                  90                  95

Leu Gly Val Gly Ile Asn Phe Ser Tyr Thr Thr Pro Asn Ile Leu Ile
                100                 105                 110

Asp Gly Gly Asp Ile Thr Gln Pro Pro Phe Gly Leu Asp Thr Ile Ile
                115                 120                 125

Thr Pro Asn Leu Phe Pro Gly Val Ser Ile Ser Ala Asp Leu Gly Asn
130                 135                 140

Gly Pro Gly Ile Gln Glu Val Ala Thr Phe Ser Val Asp Val Lys Gly
145                 150                 155                 160

Ala Lys Gly Ala Val Ala Val Ser Asn Ala His Gly Thr Val Thr Gly
                165                 170                 175

Ala Ala Gly Gly Val Leu Leu Arg Pro Phe Ala Arg Leu Ile Ala Ser
                180                 185                 190

Thr Gly Asp Ser Val Thr Thr Tyr Gly Glu Pro Trp Asn Met Asn
                195                 200                 205

<210> SEQ ID NO 32
<211> LENGTH: 50
<212> TYPE: DNA
<213> ORGANISM: Artificial Sequence
<220> FEATURE:
<223> OTHER INFORMATION: Oligonucleotides

<400> SEQUENCE: 32
tttttttttt tttttttttt tttttttttt tttttttttt tttttttttt          50

<210> SEQ ID NO 33
<211> LENGTH: 50
<212> TYPE: DNA
<213> ORGANISM: Artificial Sequence
<220> FEATURE:
<223> OTHER INFORMATION: Oligonucleotides

<400> SEQUENCE: 33
aaaaaaaaaa aaaaaaaaaa aaaaaaaaaa aaaaaaaaaa aaaaaaaaca          50

<210> SEQ ID NO 34
<211> LENGTH: 50
<212> TYPE: DNA
<213> ORGANISM: Artificial Sequence
<220> FEATURE:
<223> OTHER INFORMATION: Oligonucleotides

<400> SEQUENCE: 34
aaaaaaaaaa aaaaaaaaaa aaaaaaaaaa aaaaaaaaaa aaaaaaaaat          50

<210> SEQ ID NO 35
<211> LENGTH: 50
<212> TYPE: DNA
<213> ORGANISM: Artificial Sequence
<220> FEATURE:
```

<223> OTHER INFORMATION: Oligonucleotides

<400> SEQUENCE: 35
aaaaaaaaaa aaaaaaaaaa aaaaaaaaaa aaaaaaaaaa aaaaaaaata         50

<210> SEQ ID NO 36
<211> LENGTH: 50
<212> TYPE: DNA
<213> ORGANISM: Artificial Sequence
<220> FEATURE:
<223> OTHER INFORMATION: Oligonucleotides

<400> SEQUENCE: 36
aaaaaaaaaa aaaaaaaaaa aaaaaaaaaa aaaaaaaaaa aaaaaaataa         50

<210> SEQ ID NO 37
<211> LENGTH: 50
<212> TYPE: DNA
<213> ORGANISM: Artificial Sequence
<220> FEATURE:
<223> OTHER INFORMATION: Oligonucleotides

<400> SEQUENCE: 37
cccccccccc cccccccccc cccccccccc cccccccccc ccccccccca         50

<210> SEQ ID NO 38
<211> LENGTH: 50
<212> TYPE: DNA
<213> ORGANISM: Artificial Sequence
<220> FEATURE:
<223> OTHER INFORMATION: Oligonucleotides

<400> SEQUENCE: 38
cccccccccc cccccccccc cccccccccc cccccccccc ccccccccac         50

<210> SEQ ID NO 39
<211> LENGTH: 50
<212> TYPE: DNA
<213> ORGANISM: Artificial Sequence
<220> FEATURE:
<223> OTHER INFORMATION: Oligonucleotides

<400> SEQUENCE: 39
cccccccccc cccccccccc cccccccccc cccccccccc ccccccacc          50

<210> SEQ ID NO 40
<211> LENGTH: 58
<212> TYPE: DNA
<213> ORGANISM: Artificial Sequence
<220> FEATURE:
<223> OTHER INFORMATION: Oligonucleotides

<400> SEQUENCE: 40
cccccccccc cccccccccc cccccccccc cccccccccc cccccccccc ccccccc  58

<210> SEQ ID NO 41
<211> LENGTH: 20
<212> TYPE: DNA
<213> ORGANISM: Artificial Sequence
<220> FEATURE:
<223> OTHER INFORMATION: Oligonucleotides

<400> SEQUENCE: 41
cgaccagcac ggcatacatc                                          20

```
<210> SEQ ID NO 42
<211> LENGTH: 20
<212> TYPE: DNA
<213> ORGANISM: Artificial Sequence
<220> FEATURE:
<223> OTHER INFORMATION: Oligonucleotides

<400> SEQUENCE: 42
cgttctcggc tcgatgatcc                                             20

<210> SEQ ID NO 43
<211> LENGTH: 27
<212> TYPE: DNA
<213> ORGANISM: Artificial Sequence
<220> FEATURE:
<223> OTHER INFORMATION: Oligonucleotides

<400> SEQUENCE: 43
cctgatcaac aacggtaaca tcaccgc                                     27

<210> SEQ ID NO 44
<211> LENGTH: 21
<212> TYPE: DNA
<213> ORGANISM: Artificial Sequence
<220> FEATURE:
<223> OTHER INFORMATION: Oligonucleotides

<400> SEQUENCE: 44
ctgggcacgc ctgggcaacg g                                           21

<210> SEQ ID NO 45
<211> LENGTH: 21
<212> TYPE: DNA
<213> ORGANISM: Artificial Sequence
<220> FEATURE:
<223> OTHER INFORMATION: Oligonucleotides

<400> SEQUENCE: 45
tccggcgccc gcggtggcgt g                                           21

<210> SEQ ID NO 46
<211> LENGTH: 19
<212> TYPE: DNA
<213> ORGANISM: Artificial Sequence
<220> FEATURE:
<223> OTHER INFORMATION: Oligonucleotides

<400> SEQUENCE: 46
ggcgccaagg gtggcgtgg                                              19

<210> SEQ ID NO 47
<211> LENGTH: 20
<212> TYPE: DNA
<213> ORGANISM: Artificial Sequence
<220> FEATURE:
<223> OTHER INFORMATION: Oligonucleotides

<400> SEQUENCE: 47
cgttctcggt ccgcgtctcc                                             20

<210> SEQ ID NO 48
<211> LENGTH: 50
<212> TYPE: DNA
<213> ORGANISM: Artificial Sequence
<220> FEATURE:
<223> OTHER INFORMATION: Oligonucleotides
```

<400> SEQUENCE: 48
cccccccccc cccccccccc cccccccccc cccccccccc cccccccccc         50

<210> SEQ ID NO 49
<211> LENGTH: 50
<212> TYPE: DNA
<213> ORGANISM: Artificial Sequence
<220> FEATURE:
<223> OTHER INFORMATION: Oligonucleotides

<400> SEQUENCE: 49
aaaaaaaaaa aaaaaaaaaa aaaaaaaaaa aaaaaaaaaa aaaaaaaaaa         50

<210> SEQ ID NO 50
<211> LENGTH: 52
<212> TYPE: DNA
<213> ORGANISM: Artificial Sequence
<220> FEATURE:
<223> OTHER INFORMATION: Oligonucleotides

<400> SEQUENCE: 50
aacccaaaaa aaaaaaaaaa aaaaaaaaaa aaaaaaaaaa aaaaaaaaaa aa      52

<210> SEQ ID NO 51
<211> LENGTH: 47
<212> TYPE: DNA
<213> ORGANISM: Artificial Sequence
<220> FEATURE:
<223> OTHER INFORMATION: Oligonucleotides

<400> SEQUENCE: 51
tacgcataca tcctaagaac tcagactacc tcccaataaa tccacac            47

<210> SEQ ID NO 52
<211> LENGTH: 47
<212> TYPE: DNA
<213> ORGANISM: Artificial Sequence
<220> FEATURE:
<223> OTHER INFORMATION: Oligonucleotides

<400> SEQUENCE: 52
tcagactacc tcccaataaa tccgcagcaa tcctcacacc taataat            47

<210> SEQ ID NO 53
<211> LENGTH: 61
<212> TYPE: PRT
<213> ORGANISM: Artificial Sequence
<220> FEATURE:
<223> OTHER INFORMATION: Synthetic

<400> SEQUENCE: 53

Leu Glu Leu Gly Tyr Gln Ile Gly Phe Pro Trp Ser Leu Gly Val Gly
 1               5                  10                  15

Ile Asn Phe Ser Tyr Thr Thr Pro Asn Ile Leu Ile Asp Asp Gly Asp
            20                  25                  30

Ile Thr Ala Pro Pro Phe Gly Leu Asn Ser Val Ile Thr Pro Asn Leu
        35                  40                  45

Phe Pro Gly Val Ser Ile Ser Ala Asp Leu Gly Asn Gly
    50                  55                  60

<210> SEQ ID NO 54
<211> LENGTH: 61
<212> TYPE: PRT
<213> ORGANISM: Artificial Sequence
<220> FEATURE:
<223> OTHER INFORMATION: Synthetic

<400> SEQUENCE: 54

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Leu Ile Asp Asp Gly Asp
            20                  25                  30

Ile Thr Gly Pro Pro Phe Gly Leu Glu Ser Val Ile Thr Pro Asn Leu
        35                  40                  45

Phe Pro Gly Val Ser Ile Ser Ala Asp Leu Gly Asn Gly
    50                  55                  60

<210> SEQ ID NO 55
<211> LENGTH: 61
<212> TYPE: PRT
<213> ORGANISM: Artificial Sequence
<220> FEATURE:
<223> OTHER INFORMATION: Synthetic

<400> SEQUENCE: 55

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Leu Ile Asp Asp Gly Asp
            20                  25                  30

Ile Thr Gly Pro Pro Phe Gly Leu Glu Ser Val Ile Thr Pro Asn Leu
        35                  40                  45

Phe Pro Gly Val Ser Ile Ser Ala Asp Leu Gly Asn Gly
    50                  55                  60

<210> SEQ ID NO 56
<211> LENGTH: 61
<212> TYPE: PRT
<213> ORGANISM: Artificial Sequence
<220> FEATURE:
<223> OTHER INFORMATION: Synthetic

<400> SEQUENCE: 56

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Leu Ile Asp Asp Gly Asp
            20                  25                  30

Ile Thr Ala Pro Pro Phe Gly Leu Asn Ser Val Ile Thr Pro Asn Leu
        35                  40                  45

Phe Pro Gly Val Ser Ile Ser Ala Asp Leu Gly Asn Gly
    50                  55                  60

<210> SEQ ID NO 57
<211> LENGTH: 61
<212> TYPE: PRT
<213> ORGANISM: Artificial Sequence
<220> FEATURE:
<223> OTHER INFORMATION: Synthetic

<400> SEQUENCE: 57

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Leu Ile Asp Asp Gly Asp
            20                  25                  30

Ile Thr Gly Pro Pro Phe Gly Leu Glu Ser Val Ile Thr Pro Asn Leu
        35                  40                  45

```
Phe Pro Gly Val Ser Ile Ser Ala Asp Leu Gly Asn Gly
    50                  55                  60

<210> SEQ ID NO 58
<211> LENGTH: 61
<212> TYPE: PRT
<213> ORGANISM: Artificial Sequence
<220> FEATURE:
<223> OTHER INFORMATION: Synthetic

<400> SEQUENCE: 58

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Leu Ile Asp Asp Gly Asp
                20                  25                  30

Ile Thr Gly Pro Pro Phe Gly Leu Glu Ser Val Ile Thr Pro Asn Leu
            35                  40                  45

Phe Pro Gly Val Ser Ile Ser Ala Asp Leu Gly Asn Gly
    50                  55                  60

<210> SEQ ID NO 59
<211> LENGTH: 66
<212> TYPE: PRT
<213> ORGANISM: Artificial Sequence
<220> FEATURE:
<223> OTHER INFORMATION: Synthetic

<400> SEQUENCE: 59

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Ala Phe Asp Gly Glu Val
                20                  25                  30

Leu Asp Val Thr Gly Gly Val Gly Gly Ile Val Pro Leu Asp Ala Ile
            35                  40                  45

Val Thr Pro Pro Leu Phe Pro Gly Val Ser Ile Ser Ala Asp Leu Gly
        50                  55                  60

Asn Gly
65

<210> SEQ ID NO 60
<211> LENGTH: 66
<212> TYPE: PRT
<213> ORGANISM: Artificial Sequence
<220> FEATURE:
<223> OTHER INFORMATION: Synthetic

<400> SEQUENCE: 60

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Ala Phe Asp Gly Glu Val
                20                  25                  30

Leu Asp Val Thr Gly Gly Val Gly Gly Ile Val Pro Leu Asp Ala Ile
            35                  40                  45

Val Thr Pro Pro Leu Phe Pro Gly Val Ser Ile Ser Ala Asp Leu Gly
        50                  55                  60

Asn Gly
65

<210> SEQ ID NO 61
<211> LENGTH: 66
```

```
<212> TYPE: PRT
<213> ORGANISM: Artificial Sequence
<220> FEATURE:
<223> OTHER INFORMATION: Synthetic

<400> SEQUENCE: 61

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Ala Phe Asp Gly Glu Val
            20                  25                  30

Leu Asp Val Thr Gly Gly Val Gly Gly Ile Val Pro Leu Asp Ala Ile
        35                  40                  45

Val Thr Pro Pro Leu Phe Pro Gly Val Ser Ile Ser Ala Asp Leu Gly
    50                  55                  60

Asn Gly
65

<210> SEQ ID NO 62
<211> LENGTH: 66
<212> TYPE: PRT
<213> ORGANISM: Artificial Sequence
<220> FEATURE:
<223> OTHER INFORMATION: Synthetic

<400> SEQUENCE: 62

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Ala Phe Asp Gly Glu Val
            20                  25                  30

Leu Asp Val Thr Gly Gly Val Gly Gly Ile Val Pro Leu Asp Ala Ile
        35                  40                  45

Val Thr Pro Pro Leu Phe Pro Gly Val Ser Ile Ser Ala Asp Leu Gly
    50                  55                  60

Asn Gly
65

<210> SEQ ID NO 63
<211> LENGTH: 66
<212> TYPE: PRT
<213> ORGANISM: Artificial Sequence
<220> FEATURE:
<223> OTHER INFORMATION: Synthetic

<400> SEQUENCE: 63

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Ala Phe Asp Gly Leu Glu
            20                  25                  30

Gly Gly Ala Phe Val Asp Pro Val Leu Gly Asn Glu Phe Thr Gly Ile
        35                  40                  45

Val Thr Pro Pro Leu Phe Pro Gly Val Ser Ile Ser Ala Asp Leu Gly
    50                  55                  60

Asn Gly
65

<210> SEQ ID NO 64
<211> LENGTH: 66
<212> TYPE: PRT
<213> ORGANISM: Artificial Sequence
<220> FEATURE:
<223> OTHER INFORMATION: Synthetic
```

<400> SEQUENCE: 64

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Ala Phe Asp Gly Leu Glu
            20                  25                  30

Gly Gly Ala Phe Ile Asp Thr Thr Leu Gly Asn Glu Phe Thr Gly Ile
        35                  40                  45

Val Thr Pro Pro Leu Phe Pro Gly Val Ser Ile Ser Ala Asp Leu Gly
    50                  55                  60

Asn Gly
65

<210> SEQ ID NO 65
<211> LENGTH: 66
<212> TYPE: PRT
<213> ORGANISM: Artificial Sequence
<220> FEATURE:
<223> OTHER INFORMATION: Synthetic

<400> SEQUENCE: 65

Leu Glu Leu Gly Tyr Gln Ile Gly Phe Pro Trp Ser Leu Gly Val Gly
1               5                   10                  15

Ile Asn Phe Ser Tyr Thr Thr Pro Asn Ile Ala Phe Asp Gly Leu Glu
            20                  25                  30

Gly Ala Gly Phe Leu Asp Thr Ala Ile Gly Asn Glu Phe Thr Gly Ile
        35                  40                  45

Val Thr Pro Pro Leu Phe Pro Gly Val Ser Ile Ser Ala Asp Leu Gly
    50                  55                  60

Asn Gly
65

<210> SEQ ID NO 66
<211> LENGTH: 59
<212> TYPE: PRT
<213> ORGANISM: Artificial Sequence
<220> FEATURE:
<223> OTHER INFORMATION: Synthetic

<400> SEQUENCE: 66

Leu Glu Leu Gly Tyr Gln Val Gly Phe Pro Trp Ser Leu Gly Val Ser
1               5                   10                  15

Ile Asn Phe Ser Tyr Thr Thr Pro Asn Ile Ala Phe Asp Gly Trp Gly
            20                  25                  30

Leu Asp Asn Asn Val Val Asp Ser Ile Val Thr Pro Pro Leu Phe Pro
        35                  40                  45

Gly Val Ser Ile Ser Ala Asp Leu Gly Asn Gly
    50                  55

<210> SEQ ID NO 67
<211> LENGTH: 59
<212> TYPE: PRT
<213> ORGANISM: Artificial Sequence
<220> FEATURE:
<223> OTHER INFORMATION: Synthetic

<400> SEQUENCE: 67

Leu Glu Leu Gly Tyr Gln Val Gly Phe Pro Trp Ser Leu Gly Val Gly
1               5                   10                  15

Ile Asn Phe Ser Tyr Thr Thr Pro Asn Ile Ala Phe Asp Gly Trp Gly

```
                20                  25                  30
Leu Asp Asp Asn Leu Ala Asp Ser Ile Val Thr Pro Pro Leu Phe Pro
            35                  40                  45

Gly Val Ser Ile Ser Ala Asp Leu Gly Asn Gly
        50                  55
```

<210> SEQ ID NO 68
<211> LENGTH: 59
<212> TYPE: PRT
<213> ORGANISM: Artificial Sequence
<220> FEATURE:
<223> OTHER INFORMATION: Synthetic

<400> SEQUENCE: 68

```
Leu Glu Leu Gly Tyr Gln Val Gly Phe Pro Trp Ser Leu Gly Val Gly
1               5                   10                  15

Ile Asn Phe Ser Tyr Thr Thr Pro Asn Ile Ala Phe Asp Gly Trp Gly
                20                  25                  30

Leu Asp Asp Asn Leu Ala Asp Ser Ile Val Thr Pro Pro Leu Phe Pro
            35                  40                  45

Gly Val Ser Ile Ser Ala Asp Leu Gly Asn Gly
        50                  55
```

<210> SEQ ID NO 69
<211> LENGTH: 67
<212> TYPE: PRT
<213> ORGANISM: Artificial Sequence
<220> FEATURE:
<223> OTHER INFORMATION: Synthetic

<400> SEQUENCE: 69

```
Leu Glu Leu Gly Tyr Gln Val Gly Phe Pro Trp Ser Leu Gly Val Gly
1               5                   10                  15

Ile Asn Phe Ser Tyr Thr Thr Pro Asn Ile Ala Phe Asp Gly Tyr Gly
                20                  25                  30

Leu Asp Leu Ala Thr Pro Asp Asp Pro Phe Leu Gly Leu Ala Asp Ser
            35                  40                  45

Ile Val Thr Pro Pro Leu Phe Pro Gly Val Ser Ile Ser Ala Asp Leu
        50                  55                  60

Gly Asn Gly
65
```

<210> SEQ ID NO 70
<211> LENGTH: 61
<212> TYPE: PRT
<213> ORGANISM: Artificial Sequence
<220> FEATURE:
<223> OTHER INFORMATION: Synthetic

<400> SEQUENCE: 70

```
Leu Glu Leu Gly Tyr Gln Val Gly Phe Pro Trp Ser Leu Gly Val Gly
1               5                   10                  15

Ile Asn Phe Ser Tyr Thr Thr Pro Asn Ile Leu Ile Asp Gly Gly Asp
                20                  25                  30

Ile Thr Gln Pro Pro Phe Gly Leu Asp Thr Ile Thr Pro Asn Leu
            35                  40                  45

Phe Pro Gly Val Ser Ile Ser Ala Asp Leu Gly Asn Gly
        50                  55                  60
```

<210> SEQ ID NO 71

<211> LENGTH: 63
<212> TYPE: PRT
<213> ORGANISM: Artificial Sequence
<220> FEATURE:
<223> OTHER INFORMATION: Synthetic

<400> SEQUENCE: 71

Leu Glu Leu Gly Tyr Gln Val Gly Tyr Pro Trp Ser Leu Gly Val Gly
1               5                   10                  15

Leu Asn Phe Asn Tyr Thr Thr Pro Asn Thr Ser Ile Leu Tyr Gly Ile
            20                  25                  30

Pro Asn Ala Phe Gly Gly Asn Pro Glu Ala Ser Tyr Ile Gln Thr Thr
        35                  40                  45

Asn Leu Leu Pro Ser Ala Gly Ile Asn Val Asp Leu Gly Asn Gly
    50                  55                  60

<210> SEQ ID NO 72
<211> LENGTH: 63
<212> TYPE: PRT
<213> ORGANISM: Artificial Sequence
<220> FEATURE:
<223> OTHER INFORMATION: Synthetic

<400> SEQUENCE: 72

Leu Glu Leu Gly Tyr Gln Val Gly Tyr Pro Trp Ser Leu Gly Val Gly
1               5                   10                  15

Leu Asn Phe Asn Tyr Thr Thr Pro Asn Thr Ser Ile Leu Tyr Gly Ile
            20                  25                  30

Pro Asn Ala Phe Gly Gly Ser Pro Glu Ala Ser Tyr Val Gln Thr Thr
        35                  40                  45

Asn Leu Leu Pro Ser Ala Gly Ile Asn Val Asp Leu Gly Asn Gly
    50                  55                  60

<210> SEQ ID NO 73
<211> LENGTH: 63
<212> TYPE: PRT
<213> ORGANISM: Artificial Sequence
<220> FEATURE:
<223> OTHER INFORMATION: Synthetic

<400> SEQUENCE: 73

Leu Glu Leu Gly Tyr Gln Val Gly Tyr Pro Trp Ser Leu Gly Val Gly
1               5                   10                  15

Leu Asn Phe Asn Tyr Thr Thr Pro Asn Thr Ser Ile Leu Tyr Gly Ile
            20                  25                  30

Pro Asn Ala Phe Gly Gly Gly Pro Glu Ala Ser Tyr Ile Gln Thr Thr
        35                  40                  45

Asn Leu Leu Pro Ser Ala Gly Ile Asn Val Asp Leu Gly Asn Gly
    50                  55                  60

<210> SEQ ID NO 74
<211> LENGTH: 63
<212> TYPE: PRT
<213> ORGANISM: Artificial Sequence
<220> FEATURE:
<223> OTHER INFORMATION: Synthetic

<400> SEQUENCE: 74

Leu Glu Leu Gly Tyr Gln Val Gly Tyr Pro Trp Ser Leu Gly Val Gly
1               5                   10                  15

Leu Asn Phe Asn Tyr Thr Thr Pro Asn Thr Ser Ile Leu Tyr Gly Ile
            20                  25                  30

```
Pro Asn Ala Phe Gly Gly Pro Glu Ala Ser Tyr Ile Gln Thr Thr
            35                  40                  45

Asn Leu Leu Pro Ser Ala Gly Ile Asn Val Asp Leu Gly Asn Gly
    50                  55                  60
```

<210> SEQ ID NO 75
<211> LENGTH: 63
<212> TYPE: PRT
<213> ORGANISM: Artificial Sequence
<220> FEATURE:
<223> OTHER INFORMATION: Synthetic

<400> SEQUENCE: 75

```
Leu Glu Leu Gly Tyr Gln Val Gly Tyr Pro Trp Ser Leu Gly Val Gly
1               5                   10                  15

Leu Asn Phe Asn Tyr Thr Thr Pro Asn Thr Ser Ile Leu Tyr Gly Ile
            20                  25                  30

Pro Asn Ala Phe Gly Gly Thr Pro Glu Ala Ser Tyr Val Gln Thr Thr
            35                  40                  45

Asn Leu Leu Pro Ser Ala Gly Ile Asn Val Asp Leu Gly Asn Gly
    50                  55                  60
```

<210> SEQ ID NO 76
<211> LENGTH: 72
<212> TYPE: PRT
<213> ORGANISM: Artificial Sequence
<220> FEATURE:
<223> OTHER INFORMATION: Synthetic

<400> SEQUENCE: 76

```
Leu Thr Val Gly Tyr Gln Ile Gly Tyr Pro Ile Ala Leu Ser Gly Ala
1               5                   10                  15

Thr Ile Val Leu Asn Ser Pro Gly Leu Gly Phe Val Ile Gly Ser Ser
            20                  25                  30

Asn Gly Ile Asp Leu Gly Leu Val Pro Thr Pro Thr Leu Asp Leu His
            35                  40                  45

Ala Gly Ser Asn Val Gly Leu Ala Gly Asp Ile Ile Pro Ser Gln Glu
    50                  55                  60

Leu Asp Ile Asp Leu Ala Pro Gly
65                  70
```

<210> SEQ ID NO 77
<211> LENGTH: 71
<212> TYPE: PRT
<213> ORGANISM: Artificial Sequence
<220> FEATURE:
<223> OTHER INFORMATION: Synthetic

<400> SEQUENCE: 77

```
Leu Thr Val Gly Tyr Gln Ile Gly Tyr Pro Ile Ala Leu Ser Gly Ala
1               5                   10                  15

Thr Ile Val Leu Asn Ser Pro Gly Leu Gly Phe Val Ile Gly Ser Asn
            20                  25                  30

Gly Ile Asn Leu Gly Ile Leu Pro Asp Pro Ser Leu Ser Leu Asn Ala
            35                  40                  45

Gly Thr Asn Val Gly Leu Ala Gly Asp Ile Ile Pro Ser Gln Glu Leu
    50                  55                  60

Asp Ile Asp Leu Ala Pro Gly
65                  70
```

<210> SEQ ID NO 78
<211> LENGTH: 71
<212> TYPE: PRT
<213> ORGANISM: Artificial Sequence
<220> FEATURE:
<223> OTHER INFORMATION: Synthetic

<400> SEQUENCE: 78

```
Leu Thr Val Gly Tyr Gln Ile Gly Tyr Pro Val Ala Leu Ala Gly Ala
1               5                   10                  15

Thr Ile Val Leu Asn Thr Pro Gly Leu Gly Phe Ala Ile Gly Ser Asn
            20                  25                  30

Gly Ile Asp Leu Gly Leu Leu Pro Glu Leu Ser Leu Gly Leu Asn Ala
        35                  40                  45

Gly Thr Asn Val Glu Leu Ala Gly Asp Ile Ile Pro Ser Gln Glu Leu
    50                  55                  60

Asp Ile Asp Leu Glu Pro Gly
65                  70
```

<210> SEQ ID NO 79
<211> LENGTH: 71
<212> TYPE: PRT
<213> ORGANISM: Artificial Sequence
<220> FEATURE:
<223> OTHER INFORMATION: Synthetic

<400> SEQUENCE: 79

```
Leu Thr Val Gly Tyr Gln Ile Gly Tyr Pro Val Ala Leu Ala Gly Ala
1               5                   10                  15

Thr Ile Val Leu Asn Thr Pro Gly Leu Gly Phe Ala Ile Gly Ser Asn
            20                  25                  30

Gly Ile Asn Leu Gly Leu Val Pro Asp Phe Thr Leu Asp Leu Asn Ala
        35                  40                  45

Gly Thr Asn Ala Glu Leu Ala Gly Asp Ile Ile Pro Ser Gln Glu Leu
    50                  55                  60

Asp Ile Asp Leu Glu Pro Gly
65                  70
```

<210> SEQ ID NO 80
<211> LENGTH: 72
<212> TYPE: PRT
<213> ORGANISM: Artificial Sequence
<220> FEATURE:
<223> OTHER INFORMATION: Synthetic

<400> SEQUENCE: 80

```
Leu Thr Ile Gly Tyr Gln Ile Gly Tyr Pro Ile Ala Leu Thr Gly Ala
1               5                   10                  15

Thr Val Val Leu Asn Ser Pro Gly Leu Asp Trp Ala Val Glu Ser Gly
            20                  25                  30

Thr Asn Leu Gly Ile Gly Leu Val Pro Asp Phe Glu Leu Gly Leu Asp
        35                  40                  45

Ile Ser Asn Gly Phe Ala Ile Gly Gly Asp Ile Ile Pro Ser Gln Glu
    50                  55                  60

Leu Asp Val Asp Leu Ala Pro Gly
65                  70
```

<210> SEQ ID NO 81
<211> LENGTH: 65
<212> TYPE: PRT

<213> ORGANISM: Artificial Sequence
<220> FEATURE:
<223> OTHER INFORMATION: Synthetic

<400> SEQUENCE: 81

| Leu | Glu | Val | Gly | Tyr | Glu | Ile | Gly | Cys | Gly | Ile | Asp | Met | Ser | Thr | Ser |
|---|---|---|---|---|---|---|---|---|---|---|---|---|---|---|---|
| 1 | | | | 5 | | | | | 10 | | | | | 15 | |

| Asn | Gly | Val | Ser | Leu | Thr | Gly | Thr | Ala | Gly | Leu | Asn | Pro | Ser | Leu | Gly |
|---|---|---|---|---|---|---|---|---|---|---|---|---|---|---|---|
| | | | 20 | | | | | 25 | | | | | 30 | | |

| Val | Ile | Gly | Thr | Asp | Val | Ile | Ser | Pro | Ile | Pro | Asp | Gly | Ile | Leu | Pro |
|---|---|---|---|---|---|---|---|---|---|---|---|---|---|---|---|
| | | | 35 | | | | | 40 | | | | | 45 | | |

| Gly | Ile | Gly | Gly | Asn | Ile | Gly | Gly | Val | Thr | Val | Gly | Leu | Lys | Pro |
|---|---|---|---|---|---|---|---|---|---|---|---|---|---|---|
| 50 | | | | | 55 | | | | | 60 | | | | |

Gly
65

<210> SEQ ID NO 82
<211> LENGTH: 65
<212> TYPE: PRT
<213> ORGANISM: Artificial Sequence
<220> FEATURE:
<223> OTHER INFORMATION: Synthetic

<400> SEQUENCE: 82

| Leu | Glu | Val | Gly | Tyr | Glu | Ile | Gly | Cys | Gly | Ile | Asp | Met | Ser | Thr | Ser |
|---|---|---|---|---|---|---|---|---|---|---|---|---|---|---|---|
| 1 | | | | 5 | | | | | 10 | | | | | 15 | |

| Asn | Gly | Val | Ser | Leu | Thr | Gly | Thr | Ala | Gly | Leu | Asn | Pro | Ser | Leu | Gly |
|---|---|---|---|---|---|---|---|---|---|---|---|---|---|---|---|
| | | | 20 | | | | | 25 | | | | | 30 | | |

| Val | Ile | Gly | Thr | Asp | Val | Ile | Ser | Pro | Ile | Pro | Asp | Gly | Ile | Leu | Pro |
|---|---|---|---|---|---|---|---|---|---|---|---|---|---|---|---|
| | | | 35 | | | | | 40 | | | | | 45 | | |

| Gly | Ile | Gly | Gly | Asn | Ile | Gly | Gly | Val | Thr | Val | Gly | Leu | Lys | Pro |
|---|---|---|---|---|---|---|---|---|---|---|---|---|---|---|
| 50 | | | | | 55 | | | | | 60 | | | | |

Gly
65

<210> SEQ ID NO 83
<211> LENGTH: 65
<212> TYPE: PRT
<213> ORGANISM: Artificial Sequence
<220> FEATURE:
<223> OTHER INFORMATION: Synthetic

<400> SEQUENCE: 83

| Leu | Glu | Val | Gly | Tyr | Glu | Ile | Gly | Cys | Gly | Ile | Asp | Met | Ser | Thr | Ser |
|---|---|---|---|---|---|---|---|---|---|---|---|---|---|---|---|
| 1 | | | | 5 | | | | | 10 | | | | | 15 | |

| Asn | Gly | Val | Ser | Leu | Thr | Gly | Thr | Ala | Gly | Leu | Asn | Pro | Ser | Leu | Gly |
|---|---|---|---|---|---|---|---|---|---|---|---|---|---|---|---|
| | | | 20 | | | | | 25 | | | | | 30 | | |

| Val | Ile | Gly | Thr | Asp | Val | Ile | Ser | Pro | Ile | Pro | Asp | Gly | Ile | Leu | Pro |
|---|---|---|---|---|---|---|---|---|---|---|---|---|---|---|---|
| | | | 35 | | | | | 40 | | | | | 45 | | |

| Gly | Ile | Gly | Gly | Asn | Ile | Gly | Gly | Val | Thr | Val | Gly | Leu | Lys | Pro |
|---|---|---|---|---|---|---|---|---|---|---|---|---|---|---|
| 50 | | | | | 55 | | | | | 60 | | | | |

Gly
65

<210> SEQ ID NO 84
<211> LENGTH: 65
<212> TYPE: PRT
<213> ORGANISM: Artificial Sequence
<220> FEATURE:
<223> OTHER INFORMATION: Synthetic

```
<400> SEQUENCE: 84

Leu Glu Val Gly Tyr Glu Ile Gly Cys Gly Ile Asp Met Ser Thr Ser
1               5                   10                  15

Asn Gly Val Ser Leu Thr Gly Thr Ala Gly Leu Asn Pro Ser Leu Gly
            20                  25                  30

Val Ile Gly Thr Asp Val Ile Ser Pro Ile Pro Asp Gly Ile Leu Pro
        35                  40                  45

Gly Ile Gly Gly Asn Ile Gly Gly Val Thr Val Gly Leu Lys Pro
    50                  55                  60

Gly
65

<210> SEQ ID NO 85
<211> LENGTH: 65
<212> TYPE: PRT
<213> ORGANISM: Artificial Sequence
<220> FEATURE:
<223> OTHER INFORMATION: Synthetic

<400> SEQUENCE: 85

Leu Glu Val Gly Tyr Gln Ile Gly Cys Gly Ile Asp Met Ser Thr Ser
1               5                   10                  15

Asn Gly Val Ser Leu Thr Gly Thr Ala Gly Ile Thr Pro Ser Ile Gly
            20                  25                  30

Ile Leu Gly Thr Asp Val Ile Ser Pro Phe Pro Glu Gly Val Leu Pro
        35                  40                  45

Gly Val Ala Gly Asn Leu Gly Gly Ile Thr Ile Gly Leu Lys Pro
    50                  55                  60

Gly
65

<210> SEQ ID NO 86
<211> LENGTH: 64
<212> TYPE: PRT
<213> ORGANISM: Artificial Sequence
<220> FEATURE:
<223> OTHER INFORMATION: Synthetic

<400> SEQUENCE: 86

Leu Glu Val Gly Tyr Gln Ile Gly Cys Gly Ile Asp Met Gly Ala Asn
1               5                   10                  15

Gly Val Thr Ile Thr Gly Ser Ala Gly Val Thr Pro Ser Leu Gly Leu
            20                  25                  30

Val Gly Leu Asp Gly Glu Gly Glu Phe Ile Asp Gly Ile Ala Pro Val
        35                  40                  45

Leu Ser Thr Pro Phe Val Gly Val Ala Ile Gly Leu Arg Pro Gly
    50                  55                  60

<210> SEQ ID NO 87
<211> LENGTH: 61
<212> TYPE: PRT
<213> ORGANISM: Artificial Sequence
<220> FEATURE:
<223> OTHER INFORMATION: Synthetic

<400> SEQUENCE: 87

Leu Glu Val Gly Tyr Glu Ile Gly Cys Gly Ile Asp Met Ser Thr Ser
1               5                   10                  15

Asp Gly Val Thr Ile Gly Gly Thr Ala Gly Ile Thr Pro Gly Val Thr
            20                  25                  30
```

```
Gly Pro Val Thr Gly Val Pro Gly Asp Val Leu Pro Leu Val Val Ala
        35                  40                  45

Pro Ile Ala Gly Val Leu Asn Val Gly Leu Lys Pro Gly
    50                  55                  60

<210> SEQ ID NO 88
<211> LENGTH: 61
<212> TYPE: PRT
<213> ORGANISM: Artificial Sequence
<220> FEATURE:
<223> OTHER INFORMATION: Synthetic

<400> SEQUENCE: 88

Leu Glu Val Gly Tyr Glu Ile Gly Cys Gly Ile Asp Met Ser Thr Ser
1               5                   10                  15

Asp Gly Val Thr Ile Gly Gly Thr Ala Gly Ile Thr Pro Gly Val Thr
            20                  25                  30

Gly Pro Val Thr Gly Val Pro Gly Asp Val Leu Pro Leu Val Val Ala
        35                  40                  45

Pro Ile Ala Gly Val Leu Asn Val Gly Leu Lys Pro Gly
    50                  55                  60

<210> SEQ ID NO 89
<211> LENGTH: 64
<212> TYPE: PRT
<213> ORGANISM: Artificial Sequence
<220> FEATURE:
<223> OTHER INFORMATION: Synthetic

<400> SEQUENCE: 89

Leu Glu Val Gly Tyr Glu Ile Gly Cys Gly Ile Asp Met Ser Thr Ser
1               5                   10                  15

Asn Gly Phe Val Met Ala Asn Ser Gly Val Ala Pro Ser Ile Gly
            20                  25                  30

Ala Glu Leu Pro Leu Gly Pro Gly Gln Pro Pro Ile Leu Ile Pro Leu
        35                  40                  45

Ile Thr Gly Gln Tyr Asn Asn Val Val Ser Val Gly Leu Lys Pro Gly
    50                  55                  60

<210> SEQ ID NO 90
<211> LENGTH: 51
<212> TYPE: PRT
<213> ORGANISM: Artificial Sequence
<220> FEATURE:
<223> OTHER INFORMATION: Synthetic

<400> SEQUENCE: 90

Leu Glu Val Gly Tyr Gln Ile Gly Cys Gly Ile Ser Leu Asn Val Val
1               5                   10                  15

Lys Leu Asn Gly Ser Val Gly Ile Thr Pro Ser Val Thr Pro Thr Gly
            20                  25                  30

Leu Gly Asn Thr Arg Ile Pro Val Thr Ala Gln Ile Glu Val Phe Pro
        35                  40                  45

Gln Pro Gly
    50

<210> SEQ ID NO 91
<211> LENGTH: 51
<212> TYPE: PRT
<213> ORGANISM: Artificial Sequence
<220> FEATURE:
```

<223> OTHER INFORMATION: Synthetic

<400> SEQUENCE: 91

Leu Glu Val Gly Tyr Gln Ile Gly Cys Gly Ile Ser Leu Asn Val Val
1               5                   10                  15

Lys Leu Asn Gly Ser Ala Gly Phe Thr Pro Ser Ile Asn Asp Gln Arg
            20                  25                  30

Arg Leu Gly Val Ala Phe Pro Val Ser Ala Gln Ile Glu Val Phe Pro
        35                  40                  45

Gln Pro Gly
    50

<210> SEQ ID NO 92
<211> LENGTH: 51
<212> TYPE: PRT
<213> ORGANISM: Artificial Sequence
<220> FEATURE:
<223> OTHER INFORMATION: Synthetic

<400> SEQUENCE: 92

Leu Glu Ala Gly Tyr Gln Ile Gly Cys Gly Ile Ser Leu Ala Trp Val
1               5                   10                  15

Lys Leu Asn Gly Gly Ala Asn Ile Thr Pro Ala Ile Ser Ala Ala Gly
            20                  25                  30

Val Pro Thr Val Ser Ala Gly Ile Thr Gly Ser Ile Glu Val His Pro
        35                  40                  45

Gln Pro Gly
    50

<210> SEQ ID NO 93
<211> LENGTH: 52
<212> TYPE: PRT
<213> ORGANISM: Artificial Sequence
<220> FEATURE:
<223> OTHER INFORMATION: Synthetic

<400> SEQUENCE: 93

Leu Val Val Gly Tyr Arg Ile Gly Cys Gly Ile Val Gly Gly Pro Val
1               5                   10                  15

Glu Leu Phe Ala Thr Val Gly Ala Asn Pro Asn Ile Gly Pro Asn Ala
            20                  25                  30

Val Leu Gly Ala Val Glu Phe Pro Val Asn Gly Gln Ala Lys Val Asn
        35                  40                  45

Leu Arg Pro Gly
    50

<210> SEQ ID NO 94
<211> LENGTH: 60
<212> TYPE: PRT
<213> ORGANISM: Artificial Sequence
<220> FEATURE:
<223> OTHER INFORMATION: Synthetic

<400> SEQUENCE: 94

Phe Ile Leu Gly Tyr Gln Leu Gly Cys Gln Ser Asp Val Ser Ala Gly
1               5                   10                  15

Leu Gln Tyr Gly Gly Thr Ala Gly Leu Gly Pro Val Gly Ser Leu Gly
            20                  25                  30

Leu Gly Gly Gly Ile Leu Pro Ser Ala Ala Val Gly Val Asn Gly Gly
        35                  40                  45

```
Ala Ala Gly Phe Val Gln Thr Val Leu Gln Pro Gly
 50                  55                  60
```